(12) United States Patent
Alanine et al.

(10) Patent No.: US 6,610,723 B2
(45) Date of Patent: Aug. 26, 2003

(54) IMIDAZOLE DERIVATIVES

(75) Inventors: Alexander Alanine, Riedisheim (FR); Bernd Buettelmann, Schopfheim (DE); Marie-Paule Heitz Neidhart, Hagenthal le Bas (FR); Georg Jaeschke, Basel (CH); Emmanuel Pinard, Linsdorf (FR); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/029,342

(22) Filed: Dec. 20, 2001

(65) Prior Publication Data

US 2002/0151715 A1 Oct. 17, 2002

(30) Foreign Application Priority Data

Jan. 29, 2001 (EP) .............................. 01101947

(51) Int. Cl.$^7$ ................ A61K 31/4155; A61K 31/4196; A61K 31/4178; C07D 249/08; C07D 239/20
(52) U.S. Cl. ................ 514/397; 514/341; 514/383; 514/385; 546/272.4; 546/272.7; 546/274.1; 548/255; 548/262.2; 548/269.4; 548/300.1
(58) Field of Search ............ 546/272.4, 272.7, 546/274.1; 544/180, 238; 548/255, 262.2, 269.4, 300.1; 540/484, 553; 514/341, 383, 385, 397

(56) References Cited

U.S. PATENT DOCUMENTS 6,255,327 B1   7/2001   Brenner et al.

FOREIGN PATENT DOCUMENTS

| DE | 3627155 | 8/1986 |
|---|---|---|
| EP | 1 070 708 | 1/2001 |
| WO | WO 99/54314 | 10/1999 |

OTHER PUBLICATIONS

Alcalde et al, Accession # 1996:722793, CAPLUS. "Heterocyclic Betaines," Tetrahedron (1996), 52(48), 15171–15188.*

Gomez–Sanchez, A., et al., J. Heterocycl. Chem. 1987 vol. 24(6) pp. 1757–1763.

Lam, P., et al., Tetrahedron Lett. 1998, vol. 39(19), pp. 2941–2944.

Menozzi, G., et al. J. Heterocycl. Chem. 1993, vol. 30(4), pp. 997–1002.

Abstract corresponding to DE 3627155.

\* cited by examiner

Primary Examiner—Alan L. Rotman
Assistant Examiner—Janet L Coppins
(74) Attorney, Agent, or Firm—George W. Johnston; Patricia S. Rocha-Tramaloni

(57) ABSTRACT

Novel imidazole derivatives are disclosed. These compounds have a good affinity to the NMDA (N-methyl-D-aspartate)-receptor subtype selective blockers, which have a key function in modulating neuronal activity and plasticity which makes them key players in mediating processes underlying development of CNS as well as learning and memory formation. These compounds are useful in the control or treatment of diseases mediated by this receptor.

25 Claims, No Drawings

IMIDAZOLE DERIVATIVES

SUMMARY OF THE INVENTION

The present invention relates to compounds of formula

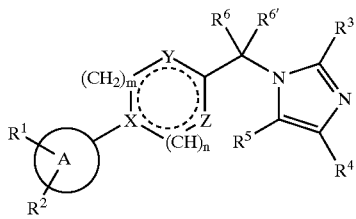

I having valuable CNS, learning and memory forming pharmacological properties.

BACKGROUND OF THE INVENTION

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Therapeutic indications for NMDA NR-2B receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections, and, in addition, depression and chronic and acute pain.

DETAILED DESCRIPTION OF THE INVENTION

The present invention is directed to novel imidazole derivatives of formula

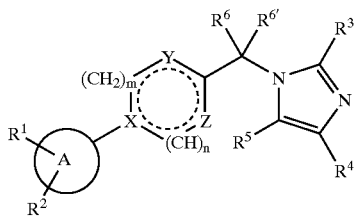

I wherein
A is phenyl, pyridin-2-yl, pyridin-3-yl, or piperidin-1-yl;
$R^1$ and $R^2$ are each independently selected from the group consisting of hydrogen, halogen, lower alkyl, cycloalkyl, lower alkenyl, trifluoromethyl, —O-trifluoromethyl, —S-trifluoromethyl, S-lower alkyl, lower alkoxy, —CHF$_2$, —C(lower alkyl)F$_2$, —OCHF$_2$, phenyl, nitro, benzyloxy, hydroxy and amino, or alternatively, $R^1$ and $R^2$ together with the carbon atoms to which they are attached in any adjacent positions, form a group selected from —CH=CH—CH=CH—, —CH=CH—CH=N—, —(CH$_2$)$_3$—, —O—CH$_2$—O—, —O—CF$_2$—O—, —CH$_2$—O—CH$_2$— and —CH$_2$CH$_2$—O—;
$R^3$ is selected from the group consisting of hydrogen, lower alkyl, cycloalkyl, phenyl, S-lower alkyl, amino, lower alkyl-amino, —NHC(O)-lower alkyl and hydroxy-lower alkyl;
$R^4$ and $R^5$ are each independently selected from hydrogen and lower alkyl, or alternatively, $R^4$ and $R^5$ together with the carbon atoms to which they are attached form the group —(CH$_2$)$_4$—;
$R^{6'}$ and $R^6$ are each independently selected from hydrogen and lower alkyl;
X is —N< or

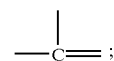

Y is =N—, —NH—, —N=CH— or —CH=;
Z is —CR$^7$, —N=, —NR$^7$—, —N=CR$^7$—, =CH—N=C(R$^7$)— or =N—CH=CH—;
$R^7$ is hydrogen, —CH$_2$OH or lower alkyl;
n is 0, 1 or 2;
m is 0 or 1; and
the dotted line may be 1, 2 or 3 bonds;
and to pharmaceutically acceptable acid addition salts thereof.

The heterocyclic aromatic group

B

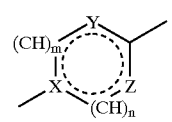

in formula I may have the following structure:

a)

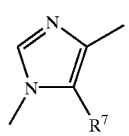

b)

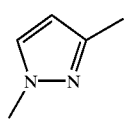

c)

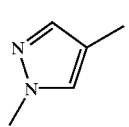

d)

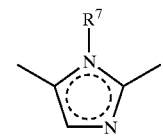

e)

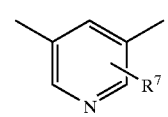

f) 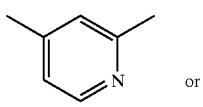 or g) 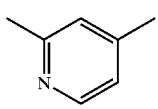

Thus, by way of example, the following type of compounds are encompassed by formula I:

Ia
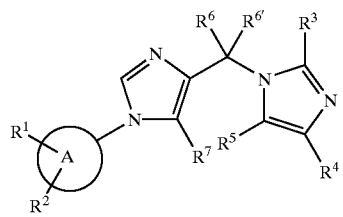

Ib
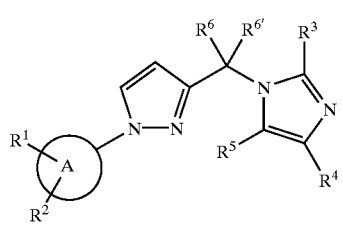

Ic
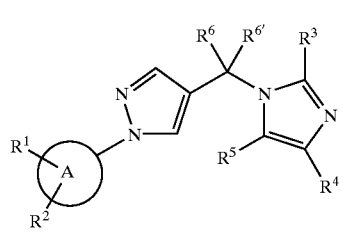

Id
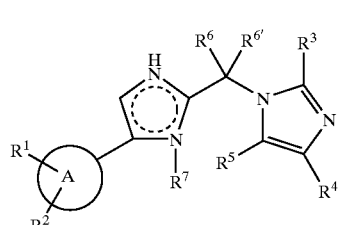

Ie
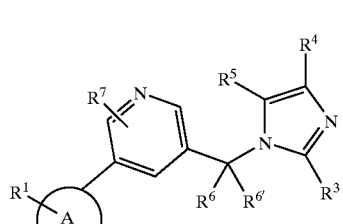

If
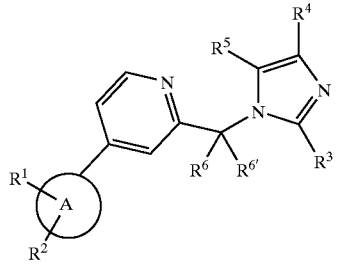

Ig
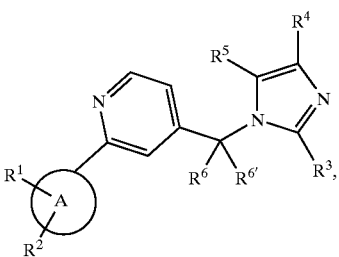

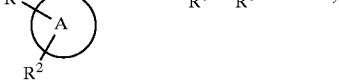

wherein substituents are as described above.

The novel compounds of the invention and their salts have valuable therapeutic properties. Compounds of the present invention are NMDA(N-methyl-D-aspartate)-receptor subtype selective blockers, which have a key function in modulating neuronal activity and plasticity which makes them key players in mediating processes underlying development of CNS as well as learning and memory formation.

Objects of the invention are the compounds of formula I and pharmaceutically acceptable acid addition salts thereof, the preparation of the compounds of formula I and salts thereof, pharmaceutical compositions containing a compound of formula I or a pharmaceutically acceptable acid addition salt thereof, and the use of the compounds of formula I and their pharmaceutically acceptable salts in the control or prevention of NMDA-mediated disorders.

The present invention embraces racemic mixtures and all their corresponding enantiomers.

The following definitions of the general terms used in the present description apply irrespective of whether the terms in question appear alone or in combination.

As used herein, the term "lower alkyl" denotes a straight- or branched-chain alkyl group containing from 1 to 7 carbon atoms, for example, methyl, ethyl, propyl, isopropyl, butyl and the like. Preferred lower alkyl groups contain from 1 to 4 carbon atoms.

As used herein, the term "lower alkenyl" denotes a $C_2$–$C_7$ carbon group, having at least one double bond in the chain.

The term "halogen" denotes chlorine, iodine, fluorine and bromine.

The term "lower alkoxy" denotes a group wherein the alkyl residue is as defined above and the alkyl group is connected to the remainder of the molecule via an oxygen atom.

The term "cycloalkyl" denotes a carbon ring with 3 to 6 carbon atoms, preperred is cyclopropyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of formula I are those wherein A is phenyl, for example the following group of compounds:

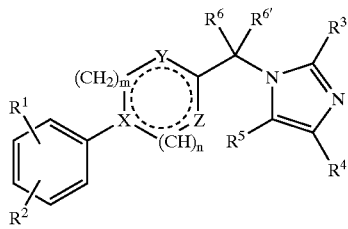

I-1 wherein
R¹ and R² are each independently selected from the group consisting of hydrogen, halogen, lower alkyl, trifluoromethyl, S-lower alkyl, lower alkoxy, —OCHF₂, phenyl, nitro, benzyloxy, hydroxy and amino, or alternatively, R¹ and R² together with the carbon atoms to which they are attached form a group selected from —(CH₂)₃—, —O—CH₂—O—, —CH₂—O—CH₂— and —CH₂CH₂—O—;
R³ is selected from the group consisting of hydrogen, lower alkyl, phenyl, S-lower alkyl, amino, lower alkyl-amino, —NHC(O)-lower alkyl and hydroxy-lower alkyl;
R⁴ and R⁵ are each independently selected from hydrogen and lower alkyl, or alternatively, R⁴ and R⁵ together with the carbon atoms to which they are attached form the group —(CH₂)₄—;
R⁶ and R⁶' are each independently selected from hydrogen and lower alkyl;
X is —N< or

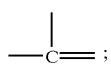

Y is =N—, —NH—, —N=CH— or —CH=;
Z is —CR=, —N=, —NH—, —N=CR⁷—, =CH—N=C(R⁷)— or =N—CH=CH—;
R⁷ is hydrogen or lower alkyl;
n is 0, 1 or 2;
m is 0 or 1; and
the dotted line may be 1, 2, or 3 bonds;
and pharmaceutically acceptable acid addition salts thereof.
Especially preferred compounds of formula

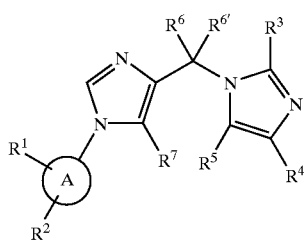

Ia in the scope of the present formula I are those, wherein A is phenyl, R¹ and R² are each independently selected from lower alkyl, —CHF₂, —C(lower alkyl)F₂, CF₃ and halogen, or alternatively, R¹ and R² together with the corresponding carbon atoms to which they are attached form the group —(CH₂)₃—; R³ is lower alkyl or amino; and R⁴, R⁵ R⁶, and R⁶' are hydrogen. Examples of such compounds are:
1H-imidazole, 1-[[1-(4-chloro-3-methylphenyl)-1H-imidazol-4-yl]methyl]-2-ethyl-;
1H-imidazole, 1-[[1-(4-chloro-3-methylphenyl)-1H-imidazol-4-yl]methyl]-2-methyl-;
1H-imidazole, 1-[[1-(2,3-dihydro-1H-inden-5-yl)-1H-imidazol-4-yl]methyl]-2-methyl-;
1H-imidazole, 1-[[1-[4-fluoro-3-(trifluoromethyl)phenyl]-1H-imidazol-4-yl]methyl]-2-methyl;
1-[1-(4-chloro-3-methyl-phenyl)-1H-imidazol-4-yl-methyl]-1H-imidazol-2-yl-amine;
1H-imidazole, 1-[[1-[3-(1,1-difluoroethyl)phenyl]-1H-imidazol-4-yl]methyl]-2-methyl-;
1H-imidazole, 1-[[1-(3-difluoromethyl-4-fluorophenyl)-1H-imidazol-4-yl]methyl]-2-methyl-; and
1H-imidazole, 1-[[1-[3-(1,1-difluoroethyl)-4-fluorophenyl]-1H-imidazol-4-yl]methyl]-2-methyl-.
Further preferred are compounds of formula

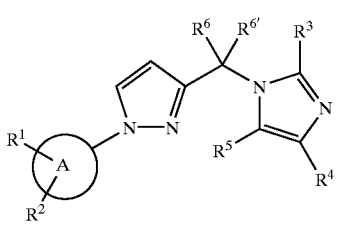

Ib in the scope of the present formula I, wherein A is phenyl, R¹ and R² are each independently selected from halogen; R³ is lower alkyl or hydrogen; and R⁴, R⁵, R⁶, and R⁶' are hydrogen. An Example of such a compound is:
1-(3,4-dichloro-phenyl)-3-(2-methyl-imidazol-1-yl-methyl)-1H-pyrazole.
Further preferred are compounds of formula

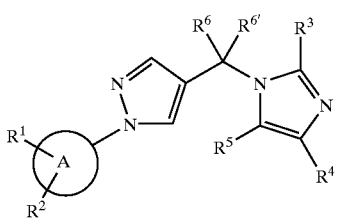

Ic in the scope of the present formula I, wherein A is phenyl, R¹ and R² are independently selected from halogen; R³ is lower alkyl or hydrogen; and R⁴, R⁵, R⁶, and R⁶' are hydrogen. Examples of such compounds are:
1-(3,4-dichloro-phenyl)-4-imidazol-1-yl-methyl-1H-pyrazole; and
1-(3,4-dichloro-phenyl)-4-(2-methyl-imidazol-1-yl-methyl)-1H-pyrazole.
Further preferred are compounds of formula

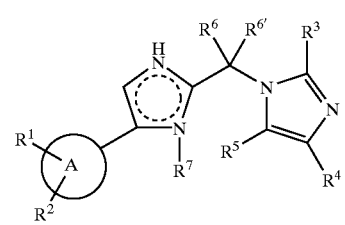

Id in the scope of the present formula 1) wherein A is phenyl, R¹ and R² are independently selected from halogen, hydrogen, CF₃ or lower alkyl; R³ is lower alkyl or hydrogen;

and $R^4$, $R^5$, $R^6$, $R^{6'}$ and $R^7$ are hydrogen. Examples of such compounds are:

1H-imidazole, 2-methyl-1-[[4-[3-(trifluoromethyl)phenyl]-1H-imidazol-2-yl]methyl]-;
1H-imidazole, 1-[[4-(4-fluoro-3-methylphenyl)-1H-imidazol-2-yl]methyl]-2-methyl-;
1H-imidazole, 1-[[4-(3,4-difluorophenyl)-1H-imidazol-2-yl]methyl]-2-methyl-; and
1H-imidazole, 4-(4-fluoro-3-methylphenyl)-2-(1H-imidazol-1-yl-methyl)-.

Further preferred are compounds of formula

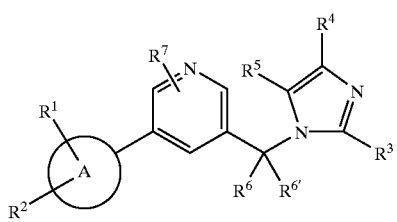

Ie in the scope of the present formula I, wherein A is phenyl, $R^1$ and $R^2$ are each independently selected from lower alkyl, halogen and $CF_3$; $R^3$ is lower alkyl or hydrogen; and $R^4$, $R^5$ $R^6$, and $R^{6'}$ are hydrogen. Examples of such compounds include:

3-(3,4-dimethyl-phenyl)-5-(2-methyl-imidazol-1-yl-methyl)-pyridine;
3-(4-fluoro-3-methyl-phenyl)-5-(2-methyl-imidazol-1-yl-methyl)-pyridine;
3-(4-chloro-3-methyl-phenyl)-5-(2-methyl-imidazol-1-yl-methyl)-pyridine;
3-(3-chloro-4-fluoro-phenyl)-5-(2-methyl-imidazol-1-yl-methyl)-pyridine; and
3-(4-chloro-3-trifluoromethyl-phenyl)-5-(2-methyl-imidazol-1-yl-methyl)-pyridine.

Further preferred are compounds of formula

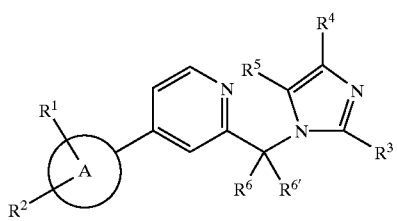

If in the scope of the present formula I, wherein A is phenyl, $R^1$ and $R^2$ are each independently selected from halogen; $R^3$ is lower alkyl; and $R^4$, $R^5$, $R^6$, and $R^{6'}$ are hydrogen. An example of such compound is:

4-(3,4-dichloro-phenyl)-2-(2-methyl-imidazol-1-yl-methyl)-pyridine.

Further preferred are compounds of formula

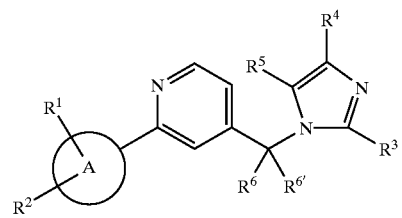

Ig in the scope of the present formula I, wherein A is phenyl, $R^1$ and $R^2$ are each independently selected from halogen; $R^3$ is lower alkyl; and $R^4$, $R^5$, $R^6$, and $R^{6'}$ are hydrogen. An example of such compound is:

2-(3,4-dichloro-phenyl)-4-(2-methyl-imidazol-1-yl-methyl)-pyridine.

Further preferred compounds of formula I are those wherein A is pyridin-2- or 3-yl or piperidin-1-yl.

The afore-mentioned compounds of formula I can be manufactured in accordance with the invention by
a) reacting a compound of formula

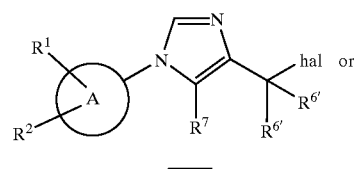

II

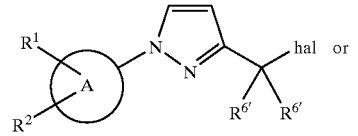

III

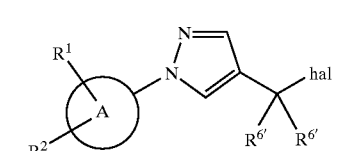

IV with a compound of formula

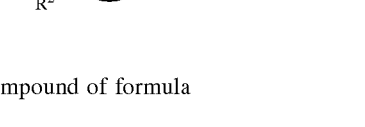

V to give a compound of formula

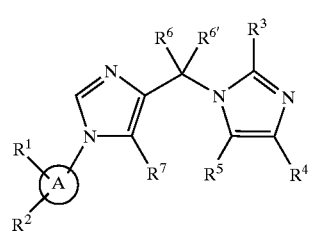

Ia

-continued

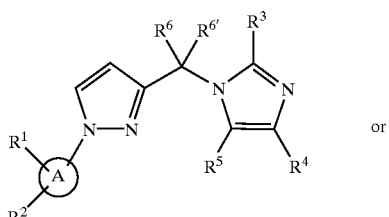

Ib

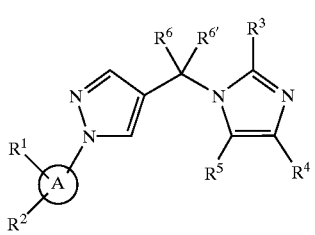

Ic wherein A is phenyl or pyridin-2 or 3-yl, $R^1$–$R^7$ have the meanings given above and hal is Br or Cl, or b) cleaving off a N-protecting group from a compound of formula

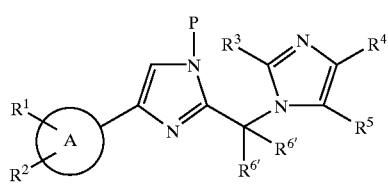

VI to obtain a compound of formula

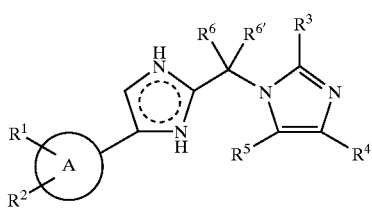

Id wherein A and $R^1$–$R^6$ have the meanings given above and P is a N-protecting group such as a 2-(trimethylsilyl)-ethoxymethyl group, or c) reacting a compound of formula

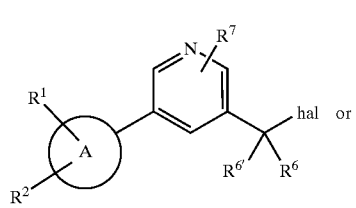

VIII

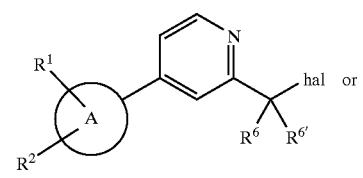

IX

-continued

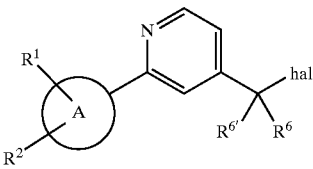

X with a compound of formula

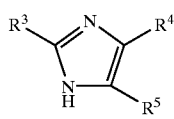

V to give a compound of formula

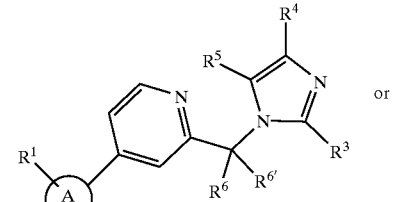

Ie
or
If

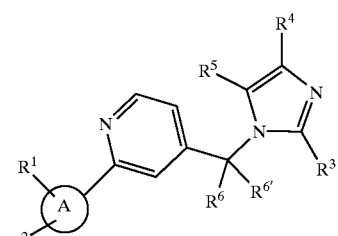

or
Ig wherein A is phenyl or pyridin-2 or 3-yl, $R^1$–$R^6$ have the meanings given above and hal is Cl or Br, and if desired, converting the compound of formula I thus obtained into a pharmaceutically acceptable salt by conventional methods known to one skilled in the art.

In the following the preparation of compounds of formula I are described in more detail:

In accordance with the process variants, described above, and with schemes 1–10, described below, compounds of formula I may be prepared by known procedures, for example the following:

In accordance with process step a), sodium hydride is added to a solution of an imidazole compound of formula V, for example 2-propylimidazole, 2-methylimidazole, imidazole, 4-methylimidazole or 4,5,6,7-tetrahydrobenzimidazole, in DMF. After 30 min. at room temperature the mixture is cooled in an ice bath and a compound of formulas II, III or IV, for example 4-chloromethyl-1-(3,4-dichloro-phenyl)-1H-imidazole, 4-chloromethyl-1-(3,4-dichloro-phenyl)-1H-pyrazole or 4-chloromethyl-1-(3,4-dichloro-phenyl)-3-methyl-1H-imidazole is added. The resulted mixture is stirred for 30 min. at room temperature and after evaporation of the solvent the compounds of formulas Ia, Ib and Ic are obtained in conventional manner.

Compounds of formulas Id may be prepared in accordance with reaction variant b). A compound of formula VI, for example 1H-imidazole, 2-[(2-methyl-1H-imidazol-1-yl)methyl]-4-[3-(trifluoromethyl)phenyl]-1-[[2-(trimethylsilyl)ethoxy]methyl] or 1H-imidazole, 4-(4-fluoro-3-methylphenyl)-[(2-methyl-1H-imidazol-1-yl)methyl]-1-[[2-(trimethylsilyl)ethoxy]methyl] is dissolved in EtOH and treated with HCl. Then the reaction mixture is refluxed overnight, cooled to room temperature, concentrated and purified.

Compounds of formulas If, Ig or Ih are prepared in accordance with reaction variant c) as follows: To a suspension of sodium hydride in mineral oil and DMF is added a compound of formula V, for example 2-propylimidazole, 2-methylimidazole, imidazole or 4-methylimidazole. This mixture is stirred for 1.5 hours at room temperature. Then a compound of formulas VIII, IX or X and triethylamine are added and the mixture is heated to about 100° C. for 4 hours. After cooling the DMF is evaporated and the residue is directly chromatographed.

Pharmaceutically acceptable salts can be manufactured according to methods which are known per se and familiar to any person skilled in the art. The acid addition salts of compounds of formula I are especially well suited for pharmaceutical use.

In the following schemes 1–10 are described processes for preparation of compounds of formula I, starting from known compounds, from commercial products or from compounds, which can be prepared in conventional manner.

The preparation of compounds of formula I are described in more detail in working examples 1–233 below.

Scheme 1

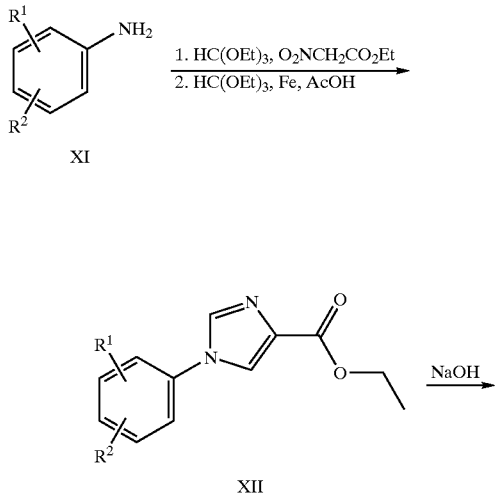

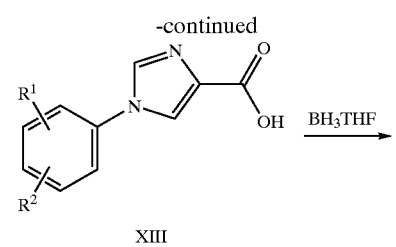

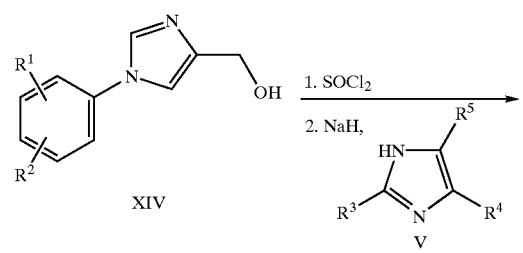

The substituents $R^1$ to $R^5$ are described above and THF is tetrahydrofuran. In the compounds of formula XI the phenyl group may be replaced by the pyridin 2- or 3-yl groups to obtain the corresponding compounds of formula Ia.

Or, alternatively, compounds of formula XIV may be prepared

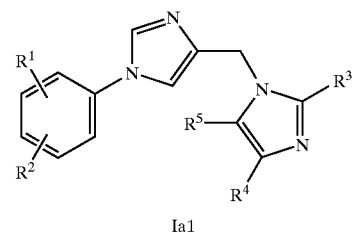

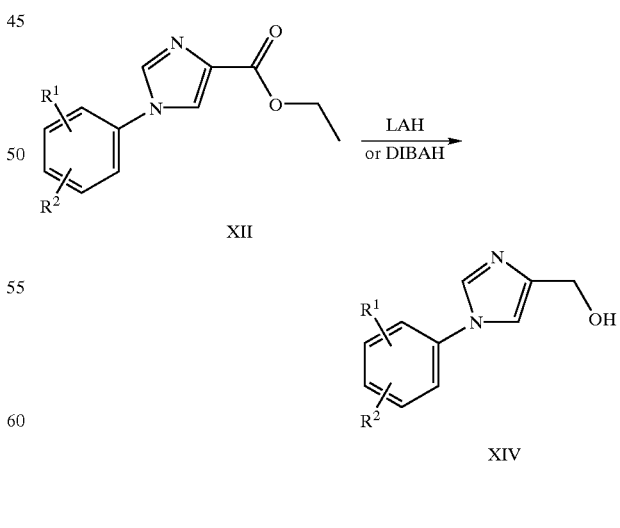

wherein $R^1$ and $R^2$ are described above and DIBAH is diisobutylaluminium hydride and LAH is lithium aluminium hydride.

Scheme 2
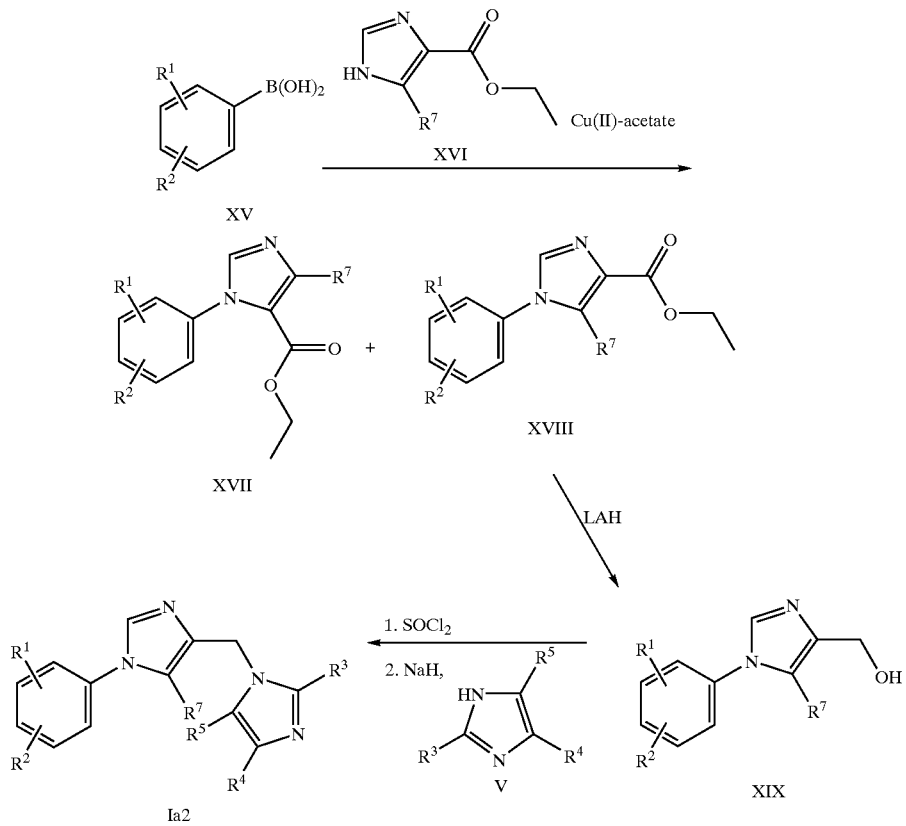
The substituents $R^1$ to $R^5$ and $R^7$ are described above and LAH is lithium aluminium hydride.
In the compounds of formula XV the phenyl group may be replaced by the pyridin 2- or 3-yl groups to obtain the corresponding compounds of formula Ia.
Scheme 3
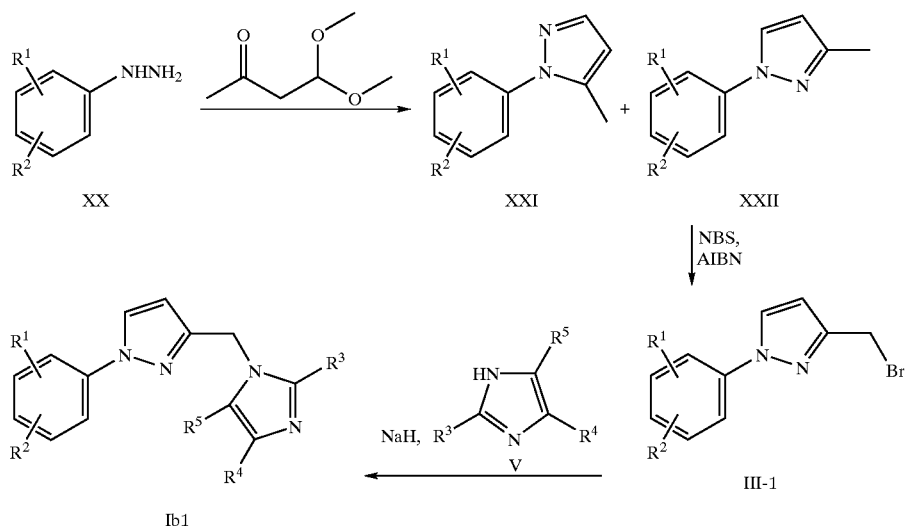

The substituents $R^1$ to $R^5$ are described above and NBS is N-bromosuccinimide and AIBN is azo-bis-isobutyronitrile.

In the compounds of formula XX the phenyl group may be replaced by the pyridin 2- or 3-yl groups to obtain the corresponding compounds of formula Ib.

Scheme 4

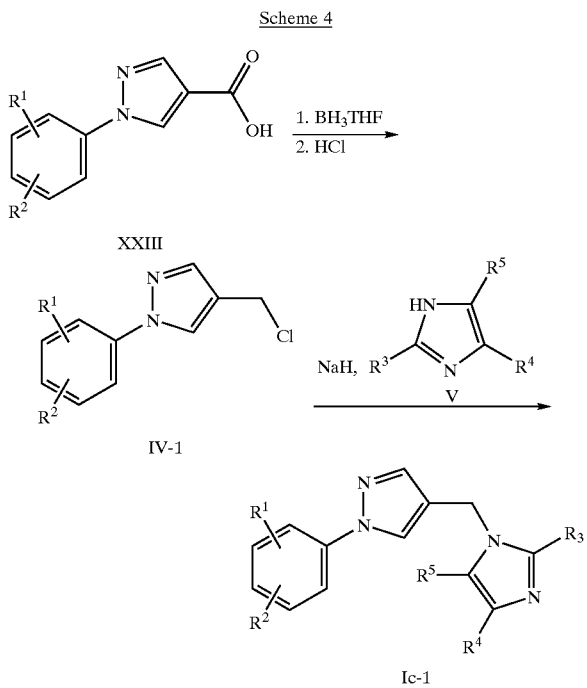

The substituents $R^1$ to $R^5$ are described above and THF is tetrahydrofuran.

In the compounds of formula XXIII the phenyl group maybe replaced by the pyridin 2- or 3-yl groups to obtain the corresponding compounds of formula Ic.

Scheme 5

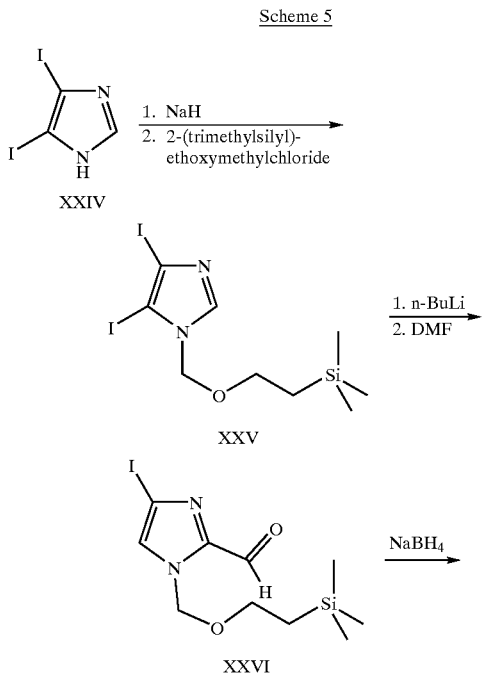

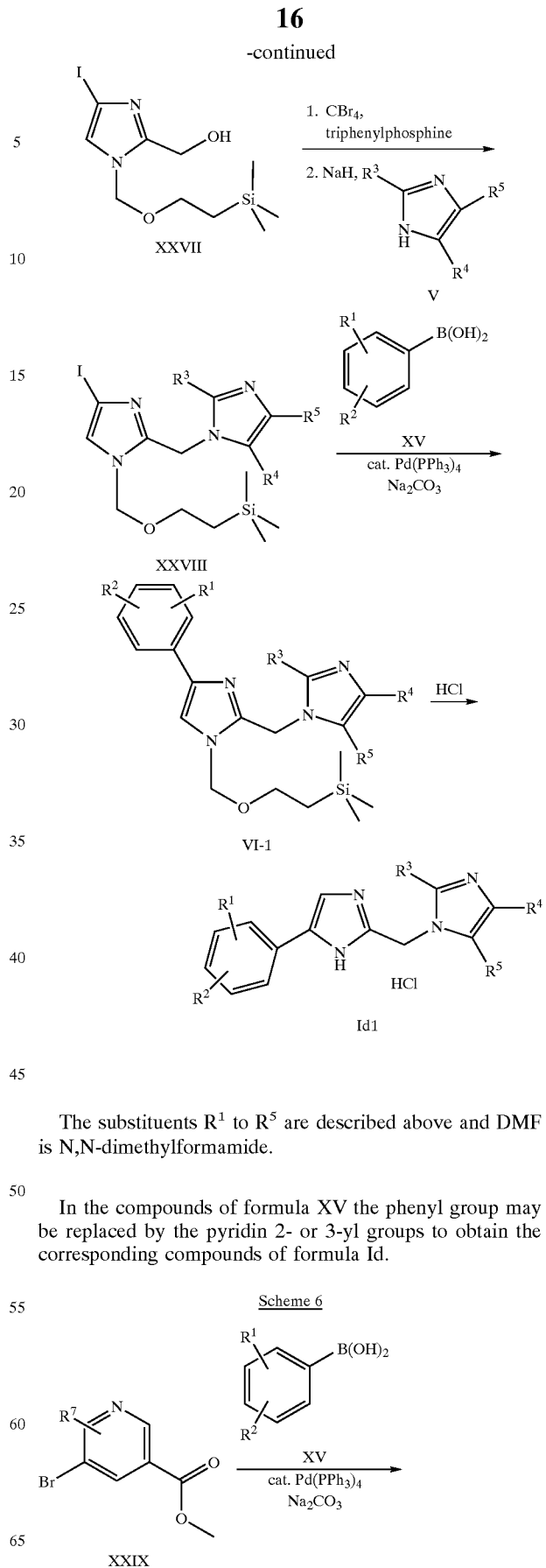

The substituents $R^1$ to $R^5$ are described above and DMF is N,N-dimethylformamide.

In the compounds of formula XV the phenyl group may be replaced by the pyridin 2- or 3-yl groups to obtain the corresponding compounds of formula Id.

Scheme 6

-continued

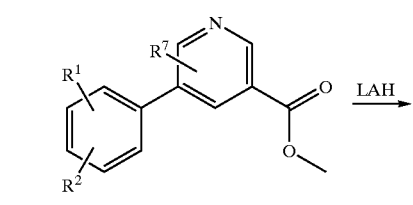

XXX

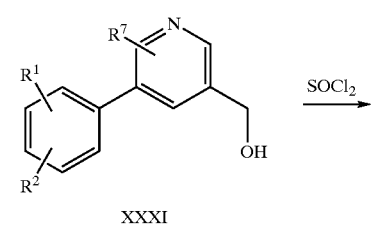

XXXI

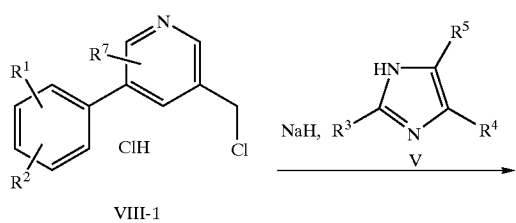

VIII-1

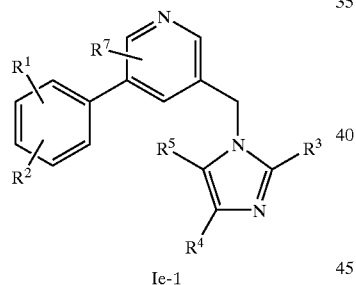

Ie-1

The substituents $R^1$ to $R^5$ and $R^7$ are described above and LAH is lithium aluminium hydride. Alternatively, the compound of formula XV may be replaced by the compound

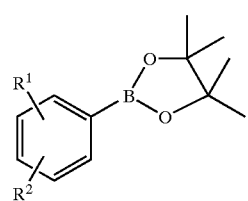

In the compounds of formula XV the phenyl group may be replaced by the pyridin 2- or 3-yl groups to obtain the corresponding compounds of formula Ie.

Scheme 7

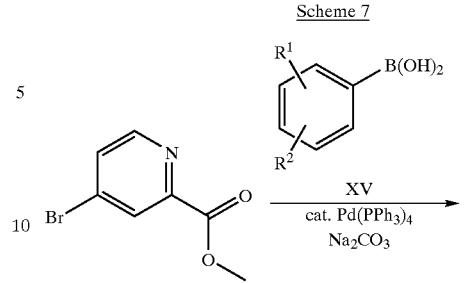

XXXII

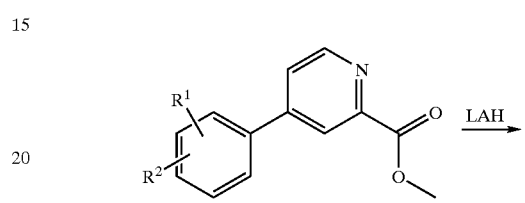

XXXIII

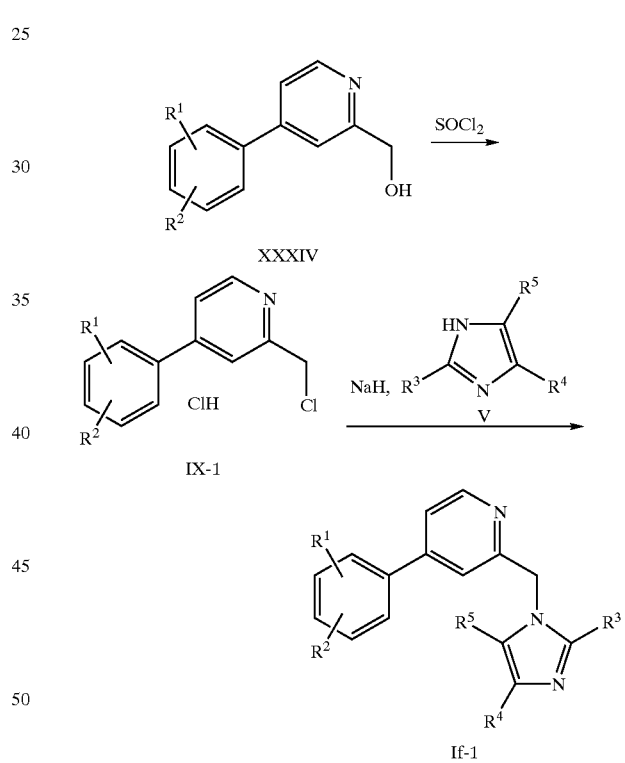

XXXIV

IX-1

If-1

The substituents $R^1$ to $R^5$ are described above.

In the compounds of formula XV the phenyl group may be replaced by the pyridin 2- or 3-yl groups to obtain the corresponding compounds of formula If.

Scheme 8

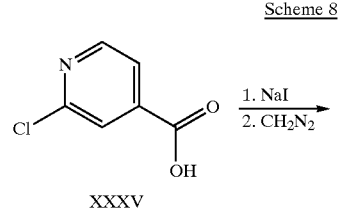

XXXV

-continued

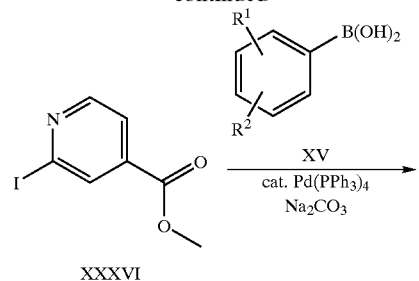

XXXVI

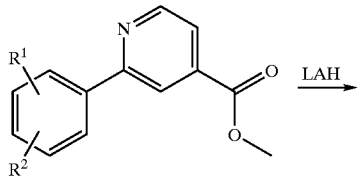

XXXVII

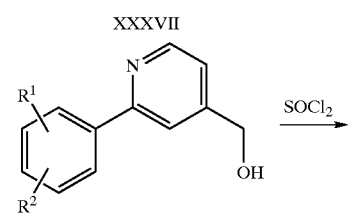

XXXVIII

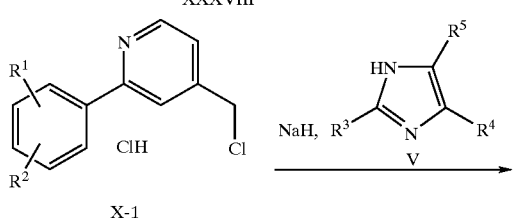

Ig-1

The substituents $R^1$ to $R^5$ are described above and LAH is lithium aluminium hydride.

In the compounds of formula XV the phenyl group may be replaced by the pyridin 2- or 3-yl groups to obtain the corresponding compounds of formula Ig.

Scheme 9

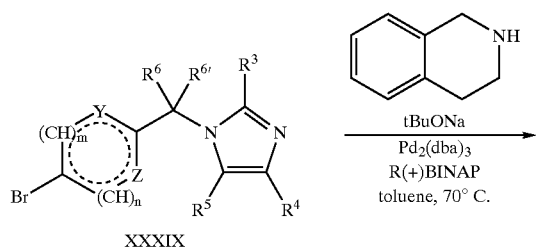

XXXIX

-continued

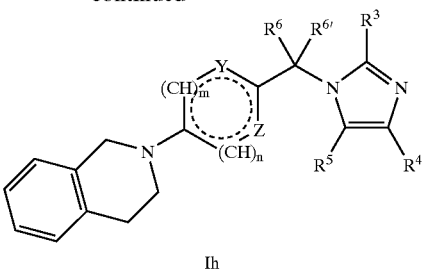

Ih

The substituents are described above and BINAP is 2,2'-bis(diphenylphosphino)-1,1'-binaphthyl.

Scheme 10

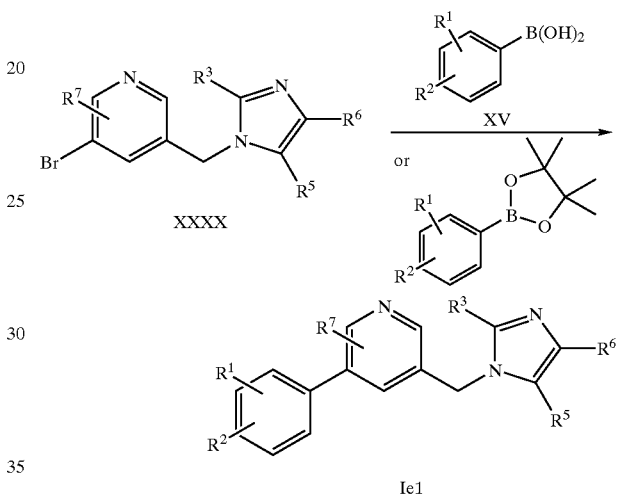

In the compounds of formula XV or of the alternative compound the phenyl group may be replaced by the pyridin 2- or 3-yl groups.

As mentioned earlier, the compounds of formula I and their pharmaceutically usable acid addition salts possess valuable pharmacodynamic properties. They are NMDA-receptor subtype 2B selective blockers, which have a key function in modulating neuronal activity and plasticity which makes them key players in mediating processes underlying development of CNS as well as learning and memory formation.

The compounds were investigated in accordance with the test given hereinafter.

Test Method $^3$H[R—(R*,S*)]-α-(4-Hydroxy-phenyl)-β-methyl-4-(phenyl-methyl)-1-piperidine Propanol ($^3$H—Ro 25-6981) Binding Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48,000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

$^3$H—Ro 25-6981 binding experiments were performed using a Tris-HCl 50 mM, pH 7.4 buffer. For displacement experiments 5 nM of $^3$H—Ro 25-6981 were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S. A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits.

The $IC_{50}$ ($\mu$M) of preferred compounds of formula I, tested in accordance with the above mentioned methods, is <0.1 $\mu$M. In the table below are shown some data for binding activity:

| Example No. | $IC_{50}$ ($\mu$M) |
|---|---|
| 1 | 0.007 |
| 2 | 0.01 |
| 3 | 0.012 |
| 4 | 0.017 |
| 6 | 0.045 |
| 10 | 0.004 |
| 11 | 0.005 |
| 12 | 0.008 |
| 13 | 0.095 |
| 16 | 0.009 |
| 17 | 0.012 |
| 21 | 0.043 |
| 24 | 0.016 |
| 27 | 0.027 |
| 39 | 0.043 |
| 48 | 0.061 |
| 52 | 0.078 |
| 58 | 0.093 |
| 87 | 0.017 |
| 89 | 0.048 |
| 93 | 0.02 |
| 94 | 0.021 |
| 103 | 0.043 |
| 105 | 0.001 |
| 109 | 0.085 |
| 111 | 0.011 |
| 119 | 0.046 |
| 130 | 0.065 |
| 136 | 0.08 |
| 139 | 0.065 |
| 140 | 0.04 |
| 141 | 0.039 |
| 143 | 0.0073 |
| 144 | 0.038 |
| 145 | 0.054 |
| 146 | 0.008 |
| 147 | 0.0092 |
| 149 | 0.0082 |
| 150 | 0.0135 |
| 151 | 0.014 |
| 152 | 0.01 |
| 153 | 0.02 |
| 154 | 0.048 |
| 155 | 0.01 |

-continued

| Example No. | $IC_{50}$ ($\mu$M) |
|---|---|
| 156 | 0.014 |
| 157 | 0.014 |
| 158 | 0.041 |
| 159 | 0.014 |
| 160 | 0.016 |
| 161 | 0.05 |
| 162 | 0.016 |
| 163 | 0.017 |
| 164 | 0.03 |
| 165 | 0.046 |
| 166 | 0.02 |
| 168 | 0.038 |
| 170 | 0.039 |
| 172 | 0.024 |
| 173 | 0.028 |
| 174 | 0.063 |
| 176 | 0.032 |
| 177 | 0.0375 |
| 178 | 0.074 |
| 180 | 0.05 |
| 181 | 0.053 |
| 183 | 0.052 |
| 186 | 0.052 |
| 189 | 0.053 |
| 192 | 0.055 |
| 194 | 0.079 |
| 199 | 0.098 |
| 224 | 0.01 |
| 225 | 0.01 |
| 226 | 0.02 |
| 227 | 0.03 |
| 229 | 0.012 |
| 230 | 0.084 |
| 232 | 0.04 |

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives stabilizers, wetting or emulsifying agents, salts to change the osmotic pressure or to act as buffers. The pharmaceutical preparations can also contain other therapeutically active substances.

The dosage can vary within wide limits and will, of course, be fitted to the individual requirements in each particular case. In the case of oral administration the dosage lies in the range of about 0.1 mg per dosage to about 1000 mg per day of a compound of formula I although the upper limit can also be exceeded when this is shown to be indicated.

The following examples illustrate the present invention in more detail. However, they are not intended to limit its scope in any manner. All temperatures are given in degree Celsius.

EXAMPLE 1

1H-Imidazole, 1-[[1-(3,4-dichlorophenyl)-1H-imidazol-4-yl]methyl]-2-propyl-, Hydrochloride (1:2)

Sodium hydride (0.44 g of a 55 O/o dispersion in mineral oil, 10 mmol) was slowly added to a solution of 2-propylimidazole (0.55 g, 5 mmol) in DMF. After 30 min at 20° C. the mixture was cooled in an ice bath and 4-chloromethyl-1-(3,4-dichloro-phenyl)-1H-imidazole (1.0 g, 4 mmol) was added in one portion. The resulting mixture was stirred for 30 min at 20° C. After evaporation of the solvent, the residue was dissolved in AcOEt, washed with H$_2$O, dried (Na$_2$SO$_4$) and chromatographed [silica, elution with gradient CH$_2$Cl$_2$ to 50% (CH$_2$Cl$_2$/MeOH/aq. NH$_4$OH= 90:10:1)]. The free base of the title compound was obtained as a brownish oil (1.12 g, 84%). After treatment with a solution of HCl in MeOH followed by addition of Et$_2$O the title compound was isolated as a white crystalline material. Mp. 241–243° C. (MeOH/Et$_2$O), MS: m/e=334(M$^+$).

Examples 2 to 9 were prepared according to the general procedure described in example 1.

EXAMPLE 2

1H-Imidazole, 1-[[1-(3,4-dichlorophenyl)-1H-imidazol-4-yl]methyl]-2-methyl-, Hydrochloride (1:2)

Reaction of 2-methylimidazole with sodium hydride followed by treatment with 4-chloromethyl-1-(3,4-dichlorophenyl)-1H-imidazole led after extractive workup and chromatography to the free base of the title compound, which was converted into its white hydrochloride salt. Mp.>250° C. (MeOH/Et$_2$O), MS: m/e=306(M$^+$).

EXAMPLE 3

1H-Imidazole, 1-[[1-(3,4-dichlorophenyl)-1H-imidazol-4-yl]methyl]-2-ethyl-, Hydrochloride (1:2)

Reaction of 2-ethylimidazole with sodium hydride followed by treatment with 4-chloromethyl-1-(3,4-dichlorophenyl)-1H-imidazole led after extractive workup and chromatography to the free base of the title compound which was converted into its white hydrochloride salt. Mp.>250° C. (MeOH/Et$_2$O), MS: m/e=320 (M$^+$).

EXAMPLE 4

1H-Imidazole, 1-[[1-(3,4-dichlorophenyl)-1H-imidazol-4-yl]methyl]-2-(1-methylethyl)-, Hydrochloride (1:2)

Reaction of 2-isopropylimidazole with sodium hydride followed by treatment with 4-chloromethyl-1-(3,4-dichlorophenyl)-1H-imidazole led after extractive workup and chromatography to the free base of the title compound which was converted into its white hydrochloride salt. Mp. 236–238° C. dec. (MeOH/Et$_2$O), MS: m/e=335 (M+H$^+$).

EXAMPLE 5

1H-Imidazole, 1-(3,4-dichlorophenyl)-4-(1H-imidazol-1-yl-methyl)-, Hydrochloride (1:2)

Reaction of imidazole with sodium hydride followed by treatment with 4-chloromethyl-1-(3,4-dichloro-phenyl)-1H-imidazole led after extractive workup and chromatography to the free base of the title compound which was converted into its white hydrochloride salt. Mp.>250° C. (MeOH/Et$_2$O), MS: m/e=292 (M$^+$).

EXAMPLE 6

1H-Imidazole, 1-(3,4-dichlorophenyl)-4-[(4-methyl-1H-imidazol-1-yl)methyl]-, Hydrochloride (1:2) and 1H-Imidazole, 1-(3,4-dichlorophenyl)-4-[(5-methyl-1H-imidazol-1-yl)methyl]-, Hydrochloride (1:2) (ratio 3:2)

Reaction of 4-methylimidazole with sodium hydride followed by treatment with 4-chloromethyl-1-(3,4-dichlorophenyl)-1H-imidazole led after extractive workup and chromatography to the mixture of the title compounds as free bases which was converted into its white hydrochloride salts. MS: m/e=306 (M$^+$).

EXAMPLE 7

1-[1-(3,4-Dichloro-phenyl)-1H-imidazol-4-yl-methyl]-4,5,6,7-tetrahydro-1H-benzoimidazole-, Hydrochloride (1:2)

Reaction of 4,5,6,7-tetrahydrobenzimidazole with sodium hydride followed by treatment with 4-chloromethyl-1-(3,4-dichloro-phenyl)-1H-imidazole led after extractive workup and chromatography to the free base of the title compound which was converted into its white hydrochloride salt. Mp.>250° C. (MeOH/Et$_2$O), MS: m/e=346 (M$^+$).

EXAMPLE 8

1H-Imidazole, 1-[[1-(3,4-dichlorophenyl)-1H-imidazol-4-yl]methyl]-4,5-dimethyl-, Hydrochloride (1:2)

Reaction of 4,5-dimethylimidazole with sodium hydride followed by treatment with 4-chloromethyl-1-(3,4-dichlorophenyl)-1H-imidazole led after extractive workup and chromatography to the free base of the title compound which was converted into its white hydrochloride salt. Mp.>250° C. (MeOH/Et$_2$O), MS: m/e=320 (Me).

EXAMPLE 9

1H-Imidazole, 1-[[1-(3,4-dichlorophenyl)-1H-imidazol-4-yl]methyl]-2-phenyl-, Hydrochloride (1:2)

Reaction of 2-phenylimidazole with sodium hydride followed by treatment with 4-chloromethyl-1-(3,4-dichlorophenyl)-1H-imidazole led after extractive workup and chromatography to the free base of the title compound which was converted into its white hydrochloride salt. Mp. 197–198° C. (MeOH/Et$_2$O), MS: m/e=369 (M+H$^+$).

EXAMPLE 10

1H-Imidazole, 1-[[1-(4-chloro-3-methylphenyl)-1H-imidazol-4-yl]methyl]-2-ethyl-, Hydrochloride (1:2)

[1-(4-Chloro-3-methyl-phenyl)-1H-imidazol-4-yl]-methanol was treated with thionylchloride and the obtained 4-chloromethyl-1-(4-chloro-3-methyl-phenyl)-1H-imidazole directly used for a further reaction as its hydrochloric salt.

As described for example 1, reaction of 2-ethylimidazole with sodium hydride followed by treatment with 4-chloromethyl-1-(4-chloro-3-methyl-phenyl)-1H-imidazole HCl salt led after extractive workup and chromatography to the free base of the title compound which was converted into its white hydrochloride salt. Mp. 186–187° C. (MeOH/Et$_2$O), MS: m/e=300 (M$^+$).

Examples 11 to 103 were prepared according to the general procedure described in example 10.

EXAMPLE 11

1H-Imidazole, 1-[[1-(4-chloro-3-methylphenyl)-1H-imidazol-4-yl]methyl]-2-methyl-, Hydrochloride (1:2)

[1-(4-Chloro-3-methyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 218–220° C. (MeOH/Et$_2$O), MS: m/e=286 (M$^+$).

EXAMPLE 12

1H-Imidazole, 1-(4-chloro-3-methylphenyl)-4-(1H-imidazol-1-yl-methyl)-, Hydrochloride (1:2)

[1-(4-Chloro-3-methyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 206–207° C. (MeOH/Et$_2$O), MS: m/e=272 (M$^+$).

EXAMPLE 13

1H-Imidazole, 1-[[1-(4-chloro-3-methylphenyl)-1H-imidazol-4-yl]methyl]-4,5-dimethyl-, Hydrochloride (1:2)

[1-(4-Chloro-3-methyl-phenyl)-1H-imidazol-4-yl]-methanol was treated first with thionylchloride, then with the reaction mixture of sodium hydride and 4,5-dimethylimidazole. After extractive workup and chromatography the title compound was obtained as the free base. It was converted into its white hydrochloride salt. Mp.>250° C. (MeOH/Et$_2$O), MS: m/e=300 (M$^+$).

EXAMPLE 14
1-[1-(4-Chloro-3-methyl-phenyl)-1H-imidazol-4-yl-methyl]-4,5,6,7-tetrahydro-1H-benzoimidazole-, Hydrochloride (1:2)

[1-(4-Chloro-3-methyl-phenyl)-1H-imidazol-4-yl]-methanol was treated first with thionylchloride, then with the reaction mixture of sodium hydride and 4,5,6,7-tetrahydro-benzimidazole. After extractive workup and chromatography the title compound was obtained as the free base. It was converted into its white hydrochloride salt. Mp.>250° C. (MeOH/Et$_2$O), MS: m/e=326 (M$^+$).

EXAMPLE 15
1H-Imidazole, 1-[[1-(4-chloro-3-methylphenyl)-1H-imidazol-4-yl]methyl]-2-(methylthio)-, Hydrochloride (1:2)

[1-(4-Chloro-3-methyl-phenyl)-1H-imidazol-4-yl]-methanol was treated first with thionylchloride, then with the reaction mixture of sodium hydride and 2-methylthioimidazole. After extractive workup and chromatography the title compound was obtained as the free base. It was converted into its white hydrochloride salt. Mp. 202–204° C. dec. (MeOH/Et$_2$O), MS: m/e=319 (M+H$^+$).

EXAMPLE 16
1H-Imidazole, 1-[[1-(2,3-dihydro-1H-inden-5-yl)-1H-imidazol-4-yl]methyl]-2-methyl-, Hydrochloride (1:2)

[(1-Indan-5-yl-1H-imidazol-4-yl)-methanol was treated first with thionylchloride, then with the reaction mixture of sodium hydride and 2-methylimidazole. After extractive workup and chromatography the title compound was obtained as the free base. It was converted into its white hydrochloride salt. Mp. 242–243° C. (MeOH/Et$_2$O), MS: m/e=278 (M$^+$).

EXAMPLE 17
1H-Imidazole, 1-[[1[-(2,3-dihydro-1H-inden-5-yl)-1H-imidazol-4-yl]methyl]-2-ethyl-, Hydrochloride (1:2)

(1-Indan-5-yl-1H-imidazol-4-yl)-methanol was treated first with thionylchloride, then with the reaction mixture of sodium hydride and 2-ethylimidazole. After extractive workup and chromatography the title compound was obtained as the free base. It was converted into its white hydrochloride salt. Mp. 240–241° C. (MeOH/Et$_2$O), MS: m/e=292 (M$^+$).

EXAMPLE 18
1H-Imidazole, 1-(2,3-dihydro-1H-inden-5-yl)-4-(1H-imidazol-1-yl-methyl)-, Hydrochloride (1:2)

[(1-Indan-5-yl-1H-imidazol-4-yl)-methanol was treated first with thionylchloride, then with the reaction mixture of sodium hydride and imidazole. After extractive workup and chromatography the title compound was obtained as the free base. It was converted into its white hydrochloride salt. Mp. 214–216° C. (MeOH/Et$_2$O), MS: m/e=264 (Me).

EXAMPLE 19
1H-Imidazole, 1-[[1-(3,4-dimethylphenyl)-1H-imidazol-4-yl]methyl]-2-ethyl-, Hydrochloride (1:2)

[1-(3,4-Dimethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp.>250° C. (MeOH/Et$_2$O), MS: m/e=280 (M$^+$).

EXAMPLE 20
1H-Imidazole, 1-[[1-(3,4-dimethylphenyl)-1H-imidazol-4-yl]methyl]-2-methyl-, Hydrochloride (1:2)

[1-(3,4-Dimethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 249–251° C. (MeOH/Et$_2$O), MS: m/e=266 (M$^+$).

EXAMPLE 21
1H-Imidazole, 1-(3,4-dimethylphenyl)-4-(1H-imidazol-1-yl-methyl)-, Hydrochloride (1:2)

[1-(3,4-Dimethyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 218–219° C. (MeOH/Et$_2$O), MS: m/e=252 (M$^+$).

EXAMPLE 22
1H-Imidazole, 2-methyl-1-[1-(4-methylphenyl)-1H-imidazol-4-yl]methyl]-, Hydrochloride (1:2)

(1-p-Tolyl-1H-imidazol-4-yl)-methanol was treated first with thionylchloride, then with the reaction mixture of sodium hydride and 2-methylimidazole. After extractive workup and chromatography the title compound was obtained as the free base. It was converted into its white hydrochloride salt. Mp.>250° C. (MeOH/Et$_2$O), MS: m/e=252 (M$^+$).

EXAMPLE 23
1H-Imidazole, 4-(1H-imidazol-1-yl-methyl)-1-(4-methylphenyl)-, Hydrochloride (1:2)

(1-p-Tolyl-1H-imidazol-4-yl)-methanol was treated first with thionylchloride, then with the reaction mixture of sodium hydride and imidazole. After extractive workup and chromatography the title compound was obtained as the free base. It was converted into its white hydrochloride salt. Mp. 228–229° C. (MeOH/Et$_2$O), MS: m/e=238 (M$^+$).

EXAMPLE 24
1H-Imidazole, 1-[[1-(4-fluoro-3-methylphenyl)-1H-imidazol-4-yl]methyl]-2-methyl-, Hydrochloride (1:2)

[1-(4-Fluoro-3-methyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 210–212° C. (MeOH/Et$_2$O), MS: m/e=270 (M$^+$).

EXAMPLE 25
1H-Imidazole, 2-ethyl-1-[[1-(4-fluoro-3-methylphenyl)-1H-imidazol-4-yl]methyl]-. Hydrochloride (1:2)

[1-(4-Fluoro-3-methyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 210–212° C. (MeOH/Et$_2$O), MS: m/e=284 (M$^+$).

EXAMPLE 26
1H-Imidazole, 1-(4-fluoro-3-methylphenyl)-4-(1H-imidazol-1-yl-methyl)-, Hydrochloride (1:2)

[1-(4-Fluoro-3-methyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 242–243° C. (MeOH/Et$_2$O), MS: m/e=256 (M$^+$).

EXAMPLE 27
1H-Imidazole, 2-methyl-1-[[1-[4-(methylthio)phenyl]-1H-imidazol-4-yl]methyl]-, Hydrochloride (1:2)

[1-(4-Methylsulfanyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 242–243° C. (MeOH/Et$_2$O), MS: m/e=284 (M$^+$).

EXAMPLE 28
1H-Imidazole, 2-ethyl-1-[[1-[4-(methylthio)phenyl]-1H-imidazol-4-yl]methyl]-, Hydrochloride (1:2)

[1-(4-Methylsulfanyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its light yellow hydrochloride salt. Mp. 161–162° C. (MeOH/Et$_2$O), MS: m/e=298 (M$^+$).

EXAMPLE 29
1H-Imidazole, 4-(1H-imidazol-1-yl-methyl)-1-[4-(methylthio)phenyl]-, Hydrochloride (1:2)

[1-(4-Methylsulfanyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its light yellow hydrochloride salt. Mp. 233–234° C. (MeOH/Et$_2$O), MS: m/e=270 (M$^+$).

EXAMPLE 30
1H-Imidazole, 2-methyl-1-[[1-[3-(trifluoromethyl)phenyl]-1H-imidazol-4-yl]methyl]-, Hydrochloride (1:2)

[1-(3-Trifluoromethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 218–220° C. (MeOH/Et$_2$O), MS: m/e=306 (M$^+$).

EXAMPLE 31
1H-Imidazole, 2-ethyl-1-[[1-[3-(trifluoromethyl)phenyl]-1H-imidazol-4-yl]methyl]-, Hydrochloride (1:2)

[1-(3-Trifluoromethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 216–218° C. (MeOH/Et$_2$O), MS: m/e=320 (M$^+$).

EXAMPLE 32
1H-Imidazole, 4-(1H-imidazol-1-yl-methyl)-1-[3-(trifluoromethyl)phenyl]-, Hydrochloride (1:2)

[1-(3-Trifluoromethyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 224–226° C. (MeOH/Et$_2$O), MS: m/e=292 (M$^+$).

EXAMPLE 33
1H-Imidazole, 2-ethyl-1-[[1-[4-fluoro-3-(trifluoromethyl)phenyl]-1H-imidazol-4-yl methyl]-, Hydrochloride (1:2)

[1-(4-Fluoro-3-trifluoromethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its light yellow hydrochloride salt. Mp.>238° C. dec. (MeOH/Et$_2$O), MS: m/e=338 (M$^+$).

EXAMPLE 34
1H-Imidazole, 1-[[1-[4-fluoro-3-(trifluoromethyl)phenyl]-1H-imidazol-4-yl]methyl]-2-methyl-, Hydrochloride (1:2)

[1-(4-Fluoro-3-trifluoromethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its light yellow hydrochloride salt. Mp.>231° C. dec. (MeOH/Et$_2$O), MS: m/e=324 (M$^+$).

EXAMPLE 35
1H-Imidazole, 1-[4-fluoro-3-(trifluoromethyl)phenyl]-4-(1H-imidazol-1-yl-methyl)-, Hydrochloride (1:2)

1-(4-Fluoro-3-trifluoromethyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its light yellow hydrochloride salt. Mp.>246° C. dec. (MeOH/Et$_2$O), MS: m/e=310 (M$^+$).

EXAMPLE 36
1H-Imidazole, 1-[3-fluoro-4-(trifluoromethyl)phenyl]-4-(1H-imidazol-1-yl-methyl)-, Hydrochloride (1:2)

[1-(3-Fluoro-4-trifluoromethyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 232–234° C. (MeOH/Et$_2$O), MS: m/e=311 (M+H$^+$).

EXAMPLE 37
1H-Imidazole, 1-[[1-[3-fluoro-4-(trifluoromethyl)phenyl]-1H-imidazol-4-yl]methyl]-2-methyl-, Hydrochloride (1:2)

[1-(3-Fluoro-4-trifluoromethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 238–239° C. (MeOH/Et$_2$O), MS: m/e=325 (M+H$^+$).

EXAMPLE 38
1H-Imidazole, 2-ethyl-1-[[1-3-fluoro-4-(trifluoromethyl)phenyl]-1H-imidazol-4-yl methyl]-, Hydrochloride (1:2)

[1-(3-Fluoro-4-trifluoromethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 222–224° C. dec. (MeOH/Et$_2$O), MS: m/e=339 (M+H$^+$).

EXAMPLE 39

1H-Imidazole, 2-methyl-1-[[1-[4-methyl-3-(trifluoromethyl)phenyl]-1H-imidazol-4-yl]methyl]-, Hydrochloride (1:2)

[1-(4-Methyl-3-trifluoromethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its off-white hydrochloride salt. Mp.>235° C. dec. (MeOH/Et$_2$O), MS: m/e=320 (M$^+$).

EXAMPLE 40

1H-Imidazole, 2-ethyl-1-[[1-[4-methyl-3-(trifluoromethyl)phenyl]-1H-imidazol-4-yl]methyl]-, Hydrochloride (1:2)

[1-(4-Methyl-3-trifluoromethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its off-white hydrochloride salt. Mp.>250° C. (MeOH/Et$_2$O), MS: m/e=334 (M$^+$).

EXAMPLE 41

1H-Imidazole, 4-(1H-imidazol-1-yl-methyl)-1-[4-methyl-3-(trifluoromethyl)phenyl]-, Hydrochloride (1:2)

[1-(4-Methyl-3-trifluoromethyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its off-white hydrochloride salt. Mp.>250° C. (MeOH/Et$_2$O), MS: m/e=306 (M$^+$).

EXAMPLE 42

1H-Imidazole, 1-[[1-(4-chloro-3-methoxyphenyl)-1H-imidazol-4-yl]methyl]-2-ethyl-, Hydrochloride (1:2)

[1-(4-Chloro-3-methoxy-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its off-white hydrochloride salt. Mp. 244–246° C. dec.(MeOH/Et$_2$O), MS: m/e=316 (M$^+$).

EXAMPLE 43

1H-Imidazole, 1-[[1-(4-chloro-3-methoxyphenyl)-1H-imidazol-4-yl]methyl]-2-methyl-, Hydrochloride (1:2)

[1-(4-Chloro-3-methoxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its off-white hydrochloride salt. Mp.>250° C. (MeOH/Et$_2$O), MS: m/e=302 (M$^+$).

EXAMPLE 44

1H-Imidazole, 1-(4-chloro-3-methoxyphenyl)-4-(1H-imidazol-1-yl-methyl)-, Hydrochloride (1:2)

[1-(4-Chloro-3-methoxy-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 221–222° C. (MeOH/Et$_2$O), MS: m/e=288 (M$^+$).

EXAMPLE 45

1H-Imidazole, 2-ethyl-1-[1-(4-fluoro-3-methoxyphenyl)-1H-imidazol-4-yl]methyl],-Hydrochloride (1:2)

[[1-(4-Fluoro-3-methoxy-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its off-white hydrochloride salt. Mp.>250° C. dec. (MeOH/Et$_2$O), MS: m/e=300 (M$^+$).

EXAMPLE 46

1H-Imidazole, 1-[[1-(4-fluoro-3-methoxyphenyl)-1H-imidazol-4-yl]methyl]-2-methyl-, Hydrochloride (1:2)

[[1-(4-Fluoro-3-methoxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its off-white hydrochloride salt. Mp.>220° C. dec. (MeOH/Et$_2$O), MS: m/e=286 (M$^+$).

EXAMPLE 47

1H-Imidazole, 1-(4-fluoro-3-methoxyphenyl)-4-(1H-imidazol-1-yl-methyl)-, Hydrochloride (1:2)

[[1-(4-Fluoro-3-methoxy-phenyl)-1H-imidazol-4-yl]-methanol was treated first with thionylchloride, then with the reaction mixture of sodium hydride and imidazole. After extractive workup and chromatography the title compound was obtained as the free base. It was converted into its off-white hydrochloride salt. Mp. 174–178° C. (MeOH/Et$_2$O), MS: m/e=272 (M$^+$).

EXAMPLE 48

1H-Imidazole, 1-[[1-(4-chlorophenyl)-1H-imidazol-4-yl]methyl]-2-methyl-, Hydrochloride (1:2)

[1-(4-Chloro-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its light yellow hydrochloride salt. Mp. 243–244° C. (MeOH/Et$_2$O), MS: m/e=272 (M$^+$).

EXAMPLE 49

1H-Imidazole, 1-[[1-(4-chlorophenyl)-1H-imidazol-4-yl]methyl]-2-ethyl-, Hydrochloride 1-(4-Chloro-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 200–201° C. (MeOH/Et$_2$O), MS: m/e=286 (M$^+$).

EXAMPLE 50

1H-Imidazole, 1-(4-chlorophenyl)-4-(1H-imidazol-1-yl-methyl)-, Hydrochloride (1:2)

[1-(4-Chloro-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 228–229° C. (MeOH/Et$_2$O), MS: m/e=258 (M$^+$).

EXAMPLE 51

1H-Imidazole, 1-[[1-(1,3-benzodioxol-5-yl)-1H-imidazol-4-yl]methyl]-2-ethyl-, Hydrochloride (1:2)

(1-Benzo [1,3]dioxol-5-yl-1H-imidazol-4-yl)-methanol was treated first with thionylchloride, then with the reaction mixture of sodium hydride and 2-ethylimidazole. After extractive workup and chromatography the title compound was obtained as the free base. It was converted into its white hydrochloride salt. Mp.>250° C. (MeOH/Et$_2$O), MS: m/e=296 (M$^+$).

EXAMPLE 52

1H-Imidazole, 1-[[1-(1,3-benzodioxol-5-yl)-1H-imidazol-4-yl]methyl]-2-methyl-, Hydrochloride (1:2)

(1-Benzo[1,3]dioxol-5-yl-1H-imidazol-4-yl)-methanol was treated first with thionylchloride, then with the reaction mixture of sodium hydride and 2-methylimidazole. After extractive workup and chromatography the title compound was obtained as the free base. It was converted into its white hydrochloride salt. Mp.>250° C. (MeOH/Et$_2$O), MS: m/e=282 (M$^+$).

EXAMPLE 53

1H-Imidazole, 1-(1,3-benzodioxol-5-yl)-4-(1H-imidazol-1-yl-methyl)-, Hydrochloride (1:2)

(1-Benzo[1,3]dioxol-5-yl-1H-imidazol-4-yl)-methanol was treated first with thionylchloride, then with the reaction mixture of sodium hydride and imidazole. After extractive workup and chromatography the title compound was obtained as the free base. It was converted into its white hydrochloride salt. Mp. 197–198° C. (MeOH/Et$_2$O), MS: m/e=268 (M$^+$).

EXAMPLE 54

1H-Imidazole, 1-[[-(3-fluoro-4-methylphenyl)-1H-imidazol-4-yl]methyl]-2-methyl-, Hydrochloride (1:2)

[1-(3-Fluoro-4-methyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp.>250° C. (MeOH/Et$_2$O), MS: m/e=270 (M$^+$).

EXAMPLE 55

1H-Imidazole, 2-ethyl-1-[[1-(3-fluoro-4-methylphenyl)-1H-imidazol-4-yl]methyl]-, Hydrochloride (1:2)

[1-(3-Fluoro-4-methyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp.>250° C. (MeOH/Et$_2$O), MS: m/e=284 (M$^+$).

EXAMPLE 56

1H-Imidazole, 1-(3-fluoro-4-methylphenyl)-4-(1H-imidazol-1-ylmethyl)-, Hydrochloride (1:2)

[1-(3-Fluoro-4-methyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 223–224° C. (MeOH/Et$_2$O), MS: m/e=256 (M$^+$).

EXAMPLE 57

1H-Imidazole, 1-[[1-(3-chloro-4-methoxyphenyl)-1H-imidazol-4-yl]methyl]-2-methyl-, Hydrochloride (1:2)

[1-(3-Chloro-4-methoxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 240–241° C. (MeOH/Et$_2$O), MS: m/e=302 (M$^+$).

EXAMPLE 58

1H-Imidazole, 1-[[1-(3-chloro-4-methoxyphenyl)-1H-imidazol-4-yl]methyl]-2-ethyl-. Hydrochloride (1:2)

[1-(3-Chloro-4-methoxy-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 220–221° C. (MeOH/Et$_2$O), MS: m/e=316 (M$^+$).

EXAMPLE 59

1H-Imidazole, 1-(3-chloro-4-methoxyphenyl)-4-(1H-imidazol-1-yl-methyl)-, Hydrochloride (1:2)

[1-(3-Chloro-4-methoxy-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 245–246° C. (MeOH/Et$_2$O), MS: m/e=288 (M$^+$).

EXAMPLE 60

1H-Imidazole, 1-[[1-(4-chloro-2-fluorophenyl)-1H-imidazol-4-yl]methyl]-2-methyl-, Hydrochloride (1:2)

[1-(4-Chloro-2-fluoro-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 235–236° C. (MeOH/Et$_2$O), MS: m/e=290 (M$^+$).

EXAMPLE 61

1H-Imidazole, 1-[[1-(4-chloro-2-fluorophenyl)-1H-imidazol-4-yl]methyl]-2-ethyl-, Hydrochloride (1:2)

[1-(4-Chloro-2-fluoro-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 248–249° C. (MeOH/Et$_2$O), MS: m/e=304 (M$^+$).

EXAMPLE 62

1H-Imidazole, 1-(4-chloro-2-fluorophenyl)-4-(1H-imidazol-1-yl-methyl)-, Hydrochloride (1:2)

[1-(4-Chloro-2-fluoro-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp.>212° C. dec. (MeOH/Et$_2$O), MS: m/e=276 (M$^+$).

EXAMPLE 63
1H-Imidazole, 1-[[1-(4-bromophenyl)-1H-imidazol-4-yl]methyl]-2-ethyl-, Hydrochloride (1:2)

1-1(4-Bromo-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp.>250° C. (MeOH/Et$_2$O), MS: m/e=330 (M$^+$).

EXAMPLE 64
1H-Imidazole, 1-[[1-(4-bromophenyl)-1H-imidazol-4-yl]methyl]-2-methyl-, Hydrochloride

[1-(4-Bromo-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp.>250° C. (MeOH/Et$_2$O), MS: m/e=316 (M$^+$).

EXAMPLE 65
1H-Imidazole, 1-(4-bromophenyl)-4-(1H-imidazol-1-yl-methyl)-, Hydrochloride (1:2)

[1-(4-Bromo-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 237–239° C. (MeOH/Et$_2$O), MS: m/e=302 (M$^+$).

EXAMPLE 66
1H-Imidazole, 1-[[1-[4-(difluoromethoxy)phenyl]-1H-imidazol-4-yl]methyl]-2-ethyl-, Hydrochloride (1:2)

[[1-(4-Difluoromethoxy-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 199–200° C. (MeOH/Et$_2$O), MS: m/e=318 (M$^+$).

EXAMPLE 67
1H-Imidazole, 1-[[1-[4-(difluoromethoxy)phenyl]-1H-imidazol-4-yl]methyl]-2-methyl-, Hydrochloride (1:2)

[[1-(4-Difluoromethoxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 228–229° C. (MeOH/Et$_2$O), MS: m/e=304 (M$^+$).

EXAMPLE 68
1H-Imidazole, 2-methyl-1-[[1-[4-(phenylmethoxy)phenyl]-1H-imidazol-4-yl]methyl]-, Hydrochloride (1:2)

[1-(4-Benzyloxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 225–226° C. (MeOH/Et$_2$O), MS: m/e=344 (M$^+$).

EXAMPLE 69
1H-Imidazole, 2-ethyl-1-[-[4-(phenylmethoxy)phenyl]-1H-imidazol-4-yl]methyl]-, Hydrochloride (1:2)

[1-(4-Benzyloxy-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 222–223° C. (MeOH/Et$_2$O), MS: m/e=358 (M$^+$).

EXAMPLE 70
1H-Imidazole, 4-(1H-imidazol-1-yl-methyl)-1-[4-(phenylmethoxy)phenyl]-, Hydrochloride

[1-(4-Benzyloxy-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 224–225° C. (MeOH/Et$_2$O), MS: m/e=330 (M$^+$).

EXAMPLE 71
1H-Imidazole, 2-ethyl-1-[[1-(3-methoxy-4-methylphenyl)-1H-imidazol-4-yl]methyl]-. Hydrochloride (1:2)

[1-(3-Methoxy-4-methyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp.>250° C. (MeOH/Et$_2$O), MS: m/e=296 (M$^+$).

EXAMPLE 72
1H-Imidazole, 1-[[1-(3-methoxy-4-methylphenyl)-1H-imidazol-4-yl]methyl]-2-methyl-, Hydrochloride (1:2)

[1-(3-Methoxy-4-methyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 232–235° C. (MeOH/Et$_2$O), MS: m/e=282 (M$^+$).

EXAMPLE 73
1H-Imidazole, 4-(1H-imidazol-1-yl-methyl)-1-(3-methoxy-4-methylphenyl)-, Hydrochloride (1:2)

[1-(3-Methoxy-4-methyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 249–251° C. (MeOH/Et$_2$O), MS: m/e=268 (M$^+$).

EXAMPLE 74
1H-Imidazole, 2-ethyl-1-[[1-[4-(trifluoromethyl)phenyl]-1H-imidazol-4-yl]methyl]-, Hydrochloride (1:2)

[1-(4-Trifluoromethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 240–242° C. (MeOH/Et$_2$O), MS: m/e=320 (M$^+$).

EXAMPLE 75
1H-Imidazole, 2-methyl-1-[[1-[4-(trifluoromethyl)phenyl]-1H-imidazol-4-yl]methyl]-, Hydrochloride (1:2)

[1-(4-Trifluoromethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 246–248° C. (MeOH/Et$_2$O), MS: m/e=306 (M$^+$).

EXAMPLE 76

1H-Imidazole, 4-(1H-imidazol-1-yl-methyl)-1-[4-(trifluoromethyl)phenyl]-, Hydrochloride (1:2)

[1-(4-Trifluoromethyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 220–222° C. (MeOH/Et$_2$O), MS: m/e=292 (M$^+$).

EXAMPLE 77

1H-Imidazole, 1-[[1-(1,3-dihydro-5-isobenzofuranyl)-1H-imidazol-4-yl]methyl]-2-ethyl-, Hydrochloride (1:2)

[1-(1,3-Dihydro-isobenzofuran-5-yl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its off-white hydrochloride salt. Mp.>108° C. dec. (MeOH/Et$_2$O), MS: m/e=294 (M$^+$).

EXAMPLE 78

1H-Imidazole, 1-[[1-(1,3-dihydro-5-isobenzofuranyl)-1H-imidazol-4-yl]methyl]-2-methyl-, Hydrochloride (1:2)

[1-(1,3-Dihydro-isobenzofuran-5-yl)-1H-imidazol-4-yl]-methanol was treated first with thionylchloride, then with the reaction mixture of sodium hydride and 2-methylimidazole. After extractive workup and chromatography the title compound was obtained as the free base. It was converted into its off-white hydrochloride salt. Mp.>250° C. (MeOH/Et$_2$O), MS: m/e=280 (M$^+$).

EXAMPLE 79

1H-Imidazole, 1-[[1-(3-fluoro-4-methoxyphenyl)-1H-imidazol-4-yl]methyl]-2-methyl-, Hydrochloride (1:2)

[1-(3-Fluoro-4-methoxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 238–240° C. (MeOH/Et$_2$O), MS: m/e=286 (M$^+$).

EXAMPLE 80

1H-Imidazole, 2-ethyl-1-[[1-(3-fluoro-4-methoxyphenyl)-1H-imidazol-4-yl]methyl]-, Hydrochloride (1:2)

[1-(3-Fluoro-4-methoxy-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 218–220° C. (MeOH/Et$_2$O), MS: m/e=300 (M$^+$).

EXAMPLE 81

1H-Imidazole, 1-[[1-(4-methoxyphenyl)-1H-imidazol-4-yl]methyl]-2-methyl-, Hydrochloride (1:2)

[1-(4-Methoxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp.>250° C. (MeOH/Et$_2$O), MS: m/e=268 (M$^+$).

EXAMPLE 82

1H-Imidazole, 2-ethyl-1-[1-(3-methoxyphenyl)-1H-imidazol-4-yl methyl]-, Hydrochloride (1:2)

1-(3-Methoxy-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 246–248° C. (MeOH/Et$_2$O), MS: m/e=282 (M$^+$).

EXAMPLE 83

1H-Imidazole, 1-[[1-(3-methoxyphenyl)-1H-imidazol-4-yl]methyl]-2-methyl-, Hydrochloride (1:2)

[1-(3-Methoxy-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 242–243° C. (MeOH/Et$_2$O), MS: m/e=268 (M$^+$).

EXAMPLE 84

1H-Imidazole, 4-(1H-imidazol-1-yl-methyl)-1-(3-methoxyphenyl)-, Hydrochloride (1:2)

[1-(3-Methoxy-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 219–220° C. (MeOH/Et$_2$O), MS: m/e=254 (M$^+$).

EXAMPLE 85

1H-Imidazole, 1-[[1-[4-methoxy-3-(trifluoromethyl)phenyl]-1H-imidazol-4-yl]methyl]-2-methyl-, Hydrochloride (1:2)

[1-(4-Methoxy-3-trifluoromethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its light brown hydrochloride salt. Mp.>222° C. dec. (MeOH/Et$_2$O), MS: m/e=337 (M+H$^+$).

EXAMPLE 86

1H-Imidazole, 2-ethyl-1-[-[4-methoxy-3-(trifluoromethyl)phenyl]-1H-imidazol-4-yl]methyl]-, Hydrochloride (1:2)

[1-(4-Methoxy-3-trifluoromethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its light brown hydrochloride salt. Mp.>226° C. dec. (MeOH/Et$_2$O), MS: m/e=351 (M+H$^+$).

EXAMPLE 87

1H-Imidazole, 1-[[1-(3-chloro-4-methylphenyl)-1H-imidazol-4-yl]methyl]-2-methyl-, Hydrochloride (1:2)

[1-(3-Chloro-4-methyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 242–243° C. (MeOH/Et$_2$O), MS: m/e=286 (M$^+$).

EXAMPLE 88
1H-Imidazole, 1-[[1-(3-chloro-4-methylphenyl)-1H-imidazol-4-yl]methyl]-2-ethyl-, Hydrochloride (1:2)

[1-(3-Chloro-4-methyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 178–179° C. (MeOH/Et$_2$O), MS: m/e=300 (M$^+$).

EXAMPLE 89
1H-Imidazole, 1-(3-chloro-4-methylphenyl)-4-(1H-imidazol-1-yl-methyl)-, Hydrochloride (1:2)

[1-(3-Chloro-4-methyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 218–220° C. (MeOH/Et$_2$O), MS: m/e=272 (M$^+$).

EXAMPLE 90
1H-Imidazole, 1-[[1-[4-chloro-3-(trifluoromethyl)phenyl]-1H-imidazol-4-yl]methyl]-2-ethyl-, Hydrochloride (1:2)

[1-(4-Chloro-3-trifluoromethyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 179–180° C. (MeOH/Et$_2$O), MS: m/e=354 (M$^+$).

EXAMPLE 91
1H-Imidazole, 1-[[1-[4-chloro-3-(trifluoromethyl)phenyl]-1H-imidazol-4-yl]methyl]-2-methyl-, Hydrochloride (1:2)

[1-(4-Chloro-3-trifluoromethyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp.>250° C. (MeOH/Et$_2$O), MS: m/e=340 (M$^+$).

EXAMPLE 92
1H-Imidazole, 1-[4-chloro-3-(trifluoromethyl)phenyl]-4-(1H-imidazol-1-ylmethyl)-, Hydrochloride (1:2)

[1-(4-Chloro-3-trifluoromethyl-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp.>250° C. (MeOH/Et$_2$O), MS: m/e=326 (M$^+$).

EXAMPLE 93
1H-Imidazole, 1-[[1-(3-chloro-4-fluorophenyl)-1H-imidazol-4-yl]methyl]-2-methyl-, Hydrochloride (1:2)

[1-(3-Chloro-4-fluoro-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp. 224–225° C. (MeOH/Et$_2$O), MS: m/e=290 (M$^+$).

EXAMPLE 94
1H-Imidazole, 1-[[1-(3-chloro-4-fluorophenyl)-1H-imidazol-4-yl]methyl]-2-ethyl-, Hydrochloride (1:2)

[1-(3-Chloro-4-fluoro-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp. 248–250° C. (MeOH/Et$_2$O), MS: m/e=304 (M$^+$).

EXAMPLE 95
1H-Imidazole, 1-(3-chloro-4-fluorophenyl)-4-(1H-imidazol-1-yl-methyl)-, Hydrochloride (1:2)

[1-(3-Chloro-4-fluoro-phenyl)-1H-imidazol-4-yl]-methanol was treated first with thionylchloride, then with the reaction mixture of sodium hydride and imidazole. After extractive workup and chromatography the title compound was obtained as the free base. It was converted into its white hydrochloride salt. Mp. 210–212° C. (MeOH/Et$_2$O), MS: m/e=276 (M$^+$).

EXAMPLE 96
1H-Imidazole, 1-[(1-[1,1'-biphenyl]-4-yl-1H-imidazol-4-yl)methyl]-2-ethyl-, Hydrochloride (1:2)

(1-Biphenyl-4-yl-1H-imidazol-4-yl)-methanol was treated first with thionylchloride, then with the reaction mixture of sodium hydride and 2-ethylimidazole. After extractive workup and chromatography the title compound was obtained as the free base. It was converted into its white hydrochloride salt. Mp. 248–253° C. (MeOH/Et$_2$O), MS: m/e=328 (M$^+$).

EXAMPLE 97
1H-Imidazole, 1-[(1-[1,1'-biphenyl]-4-yl-1H-imidazol-4-yl)methyl]-2-methyl-, Hydrochloride (1:2)

(1-Biphenyl-4-yl-1H-imidazol-4-yl)-methanol was treated first with thionylchloride, then with the reaction mixture of sodium hydride and 2-methylimidazole. After extractive workup and chromatography the title compound was obtained as the free base. It was converted into its light yellow hydrochloride salt. Mp. 169–175° C. (MeOH/Et$_2$O), MS: m/e=314 (M$^+$).

EXAMPLE 98
1H-Imidazole, 2-ethyl-1-[[1-[3-methyl-4-(1-methylethyl)phenyl]-1H-imidazol-4-yl]methyl]-, Hydrochloride (1:2)

[1-(4-Isopropyl-3-methyl-phenyl)-1H-imidazol-4-yl]-methanol was treated first with thionylchloride, then with the reaction mixture of sodium hydride and 2-ethylimidazole. After extractive workup and chromatography the title compound was obtained as the free base. It was converted into its white hydrochloride salt. Mp.>180° C. dec. (MeOH/Et$_2$O), MS: m/e=308 (M$^+$).

EXAMPLE 99
1H-Imidazole, 2-methyl-1-[[1-[3-methyl-4-(1-methylethyl)phenyl]-1H-imidazol-4-yl]methyl]-, Hydrochloride (1:2)

[1-(4-Isopropyl-3-methyl-phenyl)-1H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp.>250° C. (MeOH/Et$_2$O), MS: m/e=294 (M$^+$).

EXAMPLE 100
1H-Imidazole, 2-methyl-1-[[1-(4-nitrophenyl)-1H-imidazol-4-yl]methyl]-, Hydrochloride (1:2)

1-(4-Nitrophenyl)-1H-imidazole-4-methanol (prepared according to I. Antonini et al., *Synthesis*, 1983, 1, 47–49) was treated first with thionylchloride, then with the reaction mixture of sodium hydride and 2-methylimidazole. After extractive workup and chromatography the title compound was obtained as the free base. It was converted into its yellow hydrochloride salt. Mp.>250° C. (MeOH/Et$_2$O), MS: m/e=283 (M$^+$).

EXAMPLE 101
1H-Imidazole, 2-ethyl-1-[[1-(4-nitrophenyl)-1H-imidazol-4-yl]methyl]-, Hydrochloride (1:2)

1-(4-Nitrophenyl)-1H-imidazole-4-methanol (prepared according to I. Antonini et al., *Synthesis*, 1983, 1, 47–49) was treated first with thionylchloride, then with the reaction mixture of sodium hydride and 2-ethylimidazole. After extractive workup and chromatography the title compound was obtained as the free base. It was converted into its yellow hydrochloride salt. Mp. 196–197° C. (MeOH/Et$_2$O), MS: m/e=297 (M$^+$).

EXAMPLE 102
1H-Imidazole, 4-(1H-imidazol-1-yl-methyl)-1-(4-nitrophenyl)-, Hydrochloride (1:2)

1-(4-Nitrophenyl)-1H-imidazole-4-methanol (prepared according to I. Antonini et al., *Synthesis*, 1983, 1, 47–49) was treated first with thionylchloride, then with the reaction mixture of sodium hydride and imidazole. After extractive workup and chromatography the title compound was obtained as the free base. It was converted into its yellow hydrochloride salt. Mp. 245–246° C. (MeOH/Et$_2$O), MS: m/e 269 (M$^+$).

EXAMPLE 103
1H-Imidazole, 1-(3,4-dichlorophenyl)-5-methyl-4-(2-methyl-1 H-imidazol-1-yl) methyl]-, Hydrochloride (1:2)

[1-(3,4-Dichloro-phenyl)-5-methyl-1 H-imidazol-4-yl]-methanol was treated first with thionylchloride, then with the reaction mixture of sodium hydride and 2-methylimidazole. After extractive workup and chromatography the title compound was obtained as the free base. It was converted into its white hydrochloride salt. Mp.>240° C. dec. (MeOH/Et$_2$O), MS: m/e=320 (M$^+$).

EXAMPLE 104
1-[1-(3,4-Dichloro-phenyl)-1H-imidazol-4-yl-methyl]-1H-imidazol-2-yl-amine-, Hydrochloride (1:2)

1H-Imidazole, 1-[[1-(3,4-dichlorophenyl)-1H-imidazol-4-yl]methyl]-2-nitro-(2.1 g, 6.2 mmol) was dissolved in acetic acid (50 ml), iron powder (3.5 g, 62 mmol) was added and the resulting mixture was stirred at 60° C. for 2 h. After addition of AcOEt (200 ml), the hot mixture was again brought to reflux and filtered. All volatiles were removed in vacuo and residual acid was removed by co-evaporation with toluene. The semi-solid obtained was purified by chromatography [silica, elution with gradient CH$_2$Cl$_2$ to 100% (CH$_2$Cl$_2$/MeOH/aq. NH$_4$OH=90:10:1)] and the free base of the title compound (1.9 g, 100%) was isolated as an off-white solid. After treatment with a solution of HCl in MeOH followed by addition of Et$_2$O the title compound was isolated as a white crystalline solid. Mp. 164–165° C. (MeOH/Et$_2$O), MS: m/e=308(M+H$^+$).

Examples 105 to 107 were prepared according to the general procedure described in example 104.

EXAMPLE 105
1[-1-(4-Chloro-3-methyl-phenyl)-1H-imidazol-4-yl-methyl]-1H-imidazol-2-yl-amine-, Hydrochloride (1:2)

1H-Imidazole, 1-[[1-(4-chloro-3-methylphenyl)-1H-imidazol-4-yl]methyl]-2-nitro, was reacted with iron in acetic acid. After filtration, evaporation and chromatography the free base of the title compound was isolated. It was converted into its white hydrochloride salt. Mp. 230–233° C. (MeOH/Et$_2$O), MS: m/e=288(M+H$^+$).

EXAMPLE 106
1-(1-p-Tolyl-1H-imidazol-4-yl-methyl)-1H-imidazol-2-yl-amine-, Hydrochloride (1:2)

1H-Imidazole, 1-[[1-(4-methylphenyl)-1H-imidazol-4-yl]methyl]-2-nitro was reacted with iron in acetic acid. After filtration, evaporation and chromatography the free base of the title compound was isolated. It was converted into its white hydrochloride salt. Mp. 232–233° C. (MeOH/Et$_2$O), MS: m/e=253(M$^+$).

EXAMPLE 107
1-(1-Phenyl-1H-imidazol-4-yl-methyl)-1H-imidazol-2-yl-amine-, Hydrochloride (1:2)

1H-Imidazole, 2-nitro-1-[(1-phenyl-1H-imidazol-4-yl) methyl]-, was reacted with iron in acetic acid. After filtration, evaporation and chromatography the free base of the title compound was isolated. It was converted into its white hydrochloride salt. Mp. 153–155° C. (MeOH/Et$_2$O), MS: m/e=239(M$^+$).

EXAMPLE 108
1H-Imidazole, 1-[[1-(3,4-dichlorophenyl)-1H-imidazol-4-yl]methyl]-2,5-dimethyl-, Hydrochloride (1:2)

A suspension of N-[-(3,4-dichloro-phenyl)-1H-imidazol-4-ylmethyl]-thioacetamide (0.60 g, 2.0 mmol) in acetone (10 ml) was treated with K$_2$CO$_3$ (0.28 g, 2.0 mmol) and iodomethane (0.26 g, 1.8 mmol). The mixture was refluxed for 1 h, evaporated and suspended in EtOH (3 ml). After addition of propargylamine (1.1 g, 20 mmol) it was refluxed for 9 h. After filtration and evaporation the residue was purified by chromatography [silica, elution with gradient CH$_2$Cl$_2$ to 30% (CH$_2$Cl$_2$/MeOH/aq. NH$_4$OH=90:10:1)] and the free base of the title compound (0.20 g, 28%) was isolated as a light brown oil. After treatment with a solution of HCl in MeOH followed by addition of Et$_2$O the title compound was isolated as a white crystalline material. Mp.>250° C. (MeOH/Et$_2$O), MS: m/e=321 (M+H$^+$).

EXAMPLE 109
{1-[1-(3,4-Dichloro-phenyl)-1H-imidazol-4-yl-methyl]-1H-imidazol-2-yl}-methanol A solution of 1-[1-(3,4-dichloro-phenyl)-1H-imidazol-4-ylmethyl]-1H-imidazole-2-carbaldehyde (0.52 g, 1.6 mmol) in MeOH (16 ml) was treated with sodium borohydride (0.12 g, 3.2 mmol). The mixture was stirred at rt for 2 h. Then all volatiles were evaporated and the residue was partitioned (AcOEt/H$_2$O). The organic phase was dried (Na$_2$SO$_4$) and concentrated to approximately 30 ml. The title compound was obtained as a white crystalline material (0.21 g, 41%). Mp. 202–203° C. (AcOEt), MS: m/e=322 (M$^+$).

EXAMPLE 110
N-{1-[1-(3,4-Dichloro-phenyl)-1H-imidazol-4-yl-methyl]-1H-imidazol-2-yl}-acetamide A solution of 1-[1-(3,4-dichloro-phenyl)-1H-imidazol-4-yl-methyl]-1H-imidazol-2-ylamine (1.0 g, 3.2 mmol) in THF (32 ml) was treated at rt with triethylamine (0.33 g, 3.2 mmol) and acetyl chloride (0.25 g, 3.2 mmol). The mixture was stirred at rt for 2 h, filtered and the organic phase was evaporated to dryness. After chromatography [silica, elution with gradient $CH_2Cl_2$ to 50% ($CH_2Cl_2$/MeOH/aq. $NH_4OH$=90:10:1)] the title compound (0.19 g, 17%) was isolated as a light brown solid. Mp.>236° C. dec.(AcOEt), MS: m/e= 350 (M+H$^+$).

EXAMPLE 111
{1-[1-(3,4-Dichloro-phenyl)-1H-imidazol-4-yl-methyl]-1H-imidazol-2-yl}-ethyl-amine Hydrochloride (1:2)

N-{1-[1-(3,4-Dichloro-phenyl)-1H-imidazol-4-ylmethyl]-1H-imidazol-2-yl}-acetamide (0.30 g, 0.86 mmol) was treated with 1M $BH_3$ THF complex (1.6 ml) and refluxed for 2 h. The mixture was cooled to 5° C. and MeOH (5 ml) was added slowly. After evaporation of all volatiles the residue was taken up in 2N HCl solution (3 ml) and refluxed for 20 min. The mixture was cooled and 2N NaOH solution (3 ml) was added. After extraction with AcOEt (50 ml), the organic phase was dried ($Na_2SO_4$) and evaporated to dryness. Purification by chromatography [silica, elution with gradient $CH_2Cl_2$ to 50% ($CH_2Cl_2$/MeOH/aq. $NH_4OH$=90:10:1)] gave the free base of the title compound. After treatment with a solution of HCl in MeOH followed by addition of $Et_2O$ the title compound was isolated as an off-white crystalline material (0.062 g, 22%). Mp.>250° C. (MeOH/$Et_2O$), MS: m/e=336 (M+H').

EXAMPLE 112
1-(3,4-Dichloro-phenyl)-3-(2-methyl-imidazol-1-yl-methyl)-1H-pyrazole Hydrochloride (1:1)

A solution of 1-(3,4-dichloro-phenyl)-3-methyl-1H-pyrazole (1.4 g, 6.1 mmol) in carbon tetrachloride was treated with N-bromosuccinimide (1.2 g, 6.8 mmol) and a catalytic amount of 2,2'azobis-(isobutyronitrile). The mixture was refluxed for 2 h, cooled, filtered and evaporated. The oily residue was dissolved in DMF (10 ml) and added to a solution of sodium hydride (0.32 g, 7.3 mmol, cf example 1) deprotonated 2-metylimidazole (0.60 g, 7.3 mmol) in DMF (10 ml). After stirring for 12 h at rt all volatiles were removed in vacuo and the residue obtained was dissolved in AcOEt. The organic phase was washed with $H_2O$ (3×), dried ($Na_2SO_4$) and concentrated. Purification by chromatography [silica, elution with gradient $CH_2Cl_2$ to 60% ($CH_2Cl_2$/MeOH/aq. $NH_4OH$=90:10:1)] gave the free base of the title compound (0.98 g, 52%) as a light brown oil. After treatment with a solution of HCl in MeOH followed by addition of $Et_2O$ the title compound was isolated as a white crystalline material. Mp. 204–205° C. (MeOH/$Et_2O$), MS: m/e=306 (M$^+$).

EXAMPLE 113
1-(3,4-Dichloro-phenyl)-4-imidazol-1-yl-methyl-1H-pyrazole

Sodium hydride (0.24 g of a 55% dispersion in mineral oil, 5.5 mmol) was slowly added to a solution of imidazole (0.19 g, 2.8 mmol) in DMF (15 ml). After 30 min at 60° C. the mixture was cooled in an ice bath and 4-chloromethyl-1-(3,4-dichloro-phenyl)-1H-pyrazole (0.50 g, 1.9 mmol) was added in one portion. The resulting mixture was stirred for 1 h at 20° C. After evaporation of the solvent the residue was dissolved in AcOEt, washed with $H_2O$, dried ($Na_2SO_4$) and chromatographed [silica, elution with gradient $CH_2Cl_2$ to 30% ($CH_2Cl_2$/MeOH/aq. $NH_4OH$=90:10:1)] to obtain 0.23 g (41%) of the title compound. Mp. 103–104° C. ($iPr_2O$), MS: m/e=293(M+H$^+$)

Example 114 was prepared according to the general procedure described in example 113.

EXAMPLE 114
1-(3,4-Dichloro-phenyl)-4-(2-methyl-imidazol-1-yl-methyl)-1H-pyrazole 2-Methylimidazole was deprotonated with sodium hydride and then treated with 4-chloromethyl-1-(3,4-dichloro-phenyl)-1H-pyrazole. Extractive and chromatographic workup gave the title compound as a white crystalline solid. Mp. 176–177° C. (AcOEt), MS: m/e=307(M+H$^+$).

EXAMPLE 115
1H-Imidazole, 1-(3,4-dichlorophenyl)-4-[1-(1H-imidazol-1-yl)ethyl]-, and 1H-Imidazole, 1-(3,4-dichlorophenyl)-3-chloro-4-[1-(1H-imidazol-1-yl)ethyl]-

A mixture of 1-[1-(3,4-dichloro-phenyl)-1H-imidazol-4-yl]-ethanol (0.2 g, 0.78 mmol) and thionyl chloride (3 ml, excess) was stirred at rt for 1.5 h. The solvent was removed by a gentle air stream. Imidazole (3.5 g, excess) was then added to the residue and the mixture was stirred at 90° C. for 30 min. After the addition of $H_2O$ (10 ml), the mixture was extracted with $CH_2Cl_2$. The organic phase was dried ($Na_2SO_4$) and the solvent was evaporated. Purification of the residue by chromatography (silica, elution with $CH_2Cl_2$/MeOH/aq. $NH_4OH$=140:10:1) gave 1H-imidazole, 1-(3,4-dichlorophenyl)-4-[1-(1H-imidazol-1-yl)ethyl]-(82 mg, 34%) as a light brown solid [MS: m/e=306.1 (M$^+$)] together with a side product (1H-imidazole, 1-(3,4-dichlorophenyl)-3-chloro-4-[1-(1H-imidazol-1-yl)ethyl]-, 102 mg, 38%) as a light yellow oil. MS: m/e=341.1 (M+H$^+$).

Example 116 was prepared according to the general procedure described in example 115.

EXAMPLE 116
1H-Imidazole, 1-[1-[1-(3,4-dichlorophenyl)-1H-imidazol-4-yl]ethyl]-2-methyl- Reaction of 1-[1-(3,4-dichloro-phenyl)-1H-imidazol-4-yl]-ethanol with thionyl chloride followed by treatment with 2-methylmidazole led after extractive workup and chromatography to the title compound as a light brown solid. MS: m/e=320.1 (M$^+$).

EXAMPLE 117
1H-Imidazole, 1-(3,4-dichlorophenyl)-4-[1-(1H-imidazol-1-yl)-1-methylethyl]-

A mixture of 2-[1-(3,4-dichloro-phenyl)-1H-imidazol-4-yl]-propan-2-ol (150 mg, 0.55 mmol) and boron tribromide (I M in $CH_2Cl_2$, 3 ml) was stirred at rt for 2 h. After removal of the solvent in an air stream, the residue was dried overnight. Imidazole (226 mg, 33.2 mmol) was added, and the mixture was stirred at 100° C for 45 min. After the addition of $H_2O$, the mixture was extracted with $CH_2Cl_2$. The organic phase was dried ($Na_2SO_4$), evaporated and the residue was purified by chromatography (silica, elution first with AcOEt, then $CH_2Cl_2$/MeOH=95:5) to give the title compound (15 mg, 8%) as a light yellow solid. MS: m/e=320.0 (M$^+$).

EXAMPLE 118
1H-Imidazole, 2-methyl-1-[[4-[3-(trifluoromethyl)phenyl]-1H-imidazol-2-yl]methyl]-, Hydrochloride (1:2)

1H-Imidazole, 2-[(2-methyl-1H-imidazol-1-yl)methyl]-4-[3-(trifluoromethyl)phenyl]-1-[[2-(trimethylsilyl)ethoxy]methyl]-(0.034 g, 0.078 mmol) was dissolved in EtOH (0.8 ml) and treated with 2N HCl (0.86 ml). The reaction mixture was refluxed overnight, cooled to rt and concentrated. The crude residue was taken up in AcOEt and stirred at rt for 30 min. Filtration provided 1H-Imidazole, 2-methyl-1-[[4-[3-(trifluoromethyl)phenyl]-1H-imidazol-2-yl]methyl]-, Hydrochloride (24 mg, 81%) as a light yellow solid, MS: m/e=307.2 (M+H$^+$).

Examples 119 to 122 were prepared according to the general procedure described in example 118.

EXAMPLE 119

1H-Imidazole, 1-[[4-(4-fluoro-3-methylphenyl)-1H-imidazol-2-yl]methyl]-2-methyl-, Hydrochloride (1:2)

The title compound, MS: m/e=270.1 (M$^+$) was prepared from 1H-imidazole, 4-(4-fluoro-3-methylphenyl)-2-[(2-methyl-1H-imidazol-1-yl)methyl]-1-[[2-(trimethylsilyl)ethoxy]methyl].

EXAMPLE 120

1H-Imidazole, 1-[[4-(3,4-difluorophenyl)-1H-imidazol-2-yl]methyl]-2-methyl-, Hydrochloride (1:2)

The title compound, MS: m/e=275.2 (M+H$^+$) was prepared from 1H-imidazole, 4-(3,4-difluorophenyl)-2-[(2-methyl-1H-imidazol-1-yl)methyl]-1-[[2-(trimethyl silyl)ethoxy]methyl].

EXAMPLE 121

1H-Imidazole, 2-methyl-1-[[4-[4-(methylthio)phenyl]-1H-imidazol-2-yl]methyl)-, Hydrochloride (1:2)

The title compound, MS: m/e=285.2 (M+H$^+$) was prepared from 1H-imidazole, 2-[(2-methyl-1H-imidazol-1-yl)methyl)-4-[4-(methylthio)phenyl]-1-[[2-(trimethylsilyl)ethoxy]methyl].

EXAMPLE 122

1H-Imidazole, 4-(4-fluoro-3-methylphenyl)-2-(TH-imidazol-1-yl-methyl)-, Hydrochloride The title compound, MS: m/e=257.1 (M+H$^+$) was prepared from 1H-imidazole, 4-(4-fluoro-3-methylphenyl)-2-(1H-imidazol-1-yl-methyl)-1-[[2-(trimethylsilyl) ethoxy]methyl].

EXAMPLE 123

3-(3,4-Dichloro-phenyl)-5-(2-methyl-imidazol-1-yl-methyl)-pyridine Hydrochloride (1:1)

To a suspension of sodium hydride (17 mg of a 55% dispersion in mineral oil, 0.39 mmol) in DMF (5 ml) was added 2-methylimidazole (32 mg, 0.39 mmol). This mixture was stirred for 1.5 h at 20° C. Following this, 3-chloromethyl-5-(3,4-dichloro-phenyl)-pyridine hydrochloride (1:1) (100 mg, 0.32 mmol) and triethylamine (78 mg, 0.78 mmol) were added and the mixture heated to 100° C. for 4 h. After cooling, the DMF was evaporated and the residue was directly chromatographed [silica, elution with CH$_2$Cl$_2$/(2M NH$_3$ in MeOH)=85:15] to afford the free base of the title compound as a yellow oil. This material was dissolved in MeOH, cooled to 4° C. with stirring and treated with HCl/EtOH (1.46 M 1.1 eq) for 15 min. Evaporation of the solvent and drying under high vacuum at 50° C. for 2 h afforded the title compound (71 mg, 62%) as a light yellow solid. MS: m/e=317.1 (M$^+$)

Examples 124 to 127 were prepared according to the general procedure described in example 123.

EXAMPLE 124

4-(3,4-Dichloro-phenyl)-2-(2-methyl-imidazol-1-yl-methyl)-pyridine Hydrochloride (1:1)

The title compound, MS: m/e=317.0 (M$^+$) was obtained as a light brown solid (60% yield) by the reaction of 2-chloromethyl-3-(3,4-dichloro-phenyl)-pyridine hydrochloride (1:1) with 2-methylimidazole, using sodium hydride and triethylamine as base followed by formation of the hydrochloride salt.

EXAMPLE 125

2-(3,4-Dichloro-phenyl)-4-(2-methyl-imidazol-1-yl-methyl)-pyridine Hydrochloride (1:2)

The title compound, MS: m/e=317.0 (M$^+$) was obtained as a beige solid (51% yield) by the reaction of 4-chloromethyl-2-(3,4-dichloro-phenyl)-pyridine hydrochloride (1:1) with 2-methylimidazole, using sodium hydride and triethylamine as base followed by formation of the hydrochloride salt.

EXAMPLE 126

3-(3,4-Dichloro-phenyl)-5-imidazol-1-yl-methyl-pyridine Hydrochloride (1:1)

The title compound, MS: m/e=304.1 (M+H$^+$) was obtained as a solid (56% yield) by the reaction of 3-chloromethyl-5-(3,4-dichloro-phenyl)-pyridine hydrochloride (1:1) with imidazole, using sodium hydride and triethylamine as base followed by formation of the hydrochloride salt.

EXAMPLE 127

3-(3,4-Dichloro-phenyl)-5-(2-ethyl-imidazol-1-yl-methyl)-pyridine Hydrochloride (1:1)

The title compound, MS: m/e=332.2 (M+H$^+$) was obtained as an orange solid (49% yield) by the reaction of 3-chloromethyl-5-(3,4-dichloro-phenyl)-pyridine hydrochloride (1:1) with 2-ethylimidazole, using sodium hydride and triethylamine as base followed by formation of the hydrochloride salt.

EXAMPLE 128

5-(3,4-Dimethyl-phenyl)-2-methyl-3-(2-methyl-imidazol-1-yl-methyl)-pyridine Hydrochloride (1:1)

The title compound, MS: m/e=292.2 (M+H$^+$) was obtained as a beige solid (77% yield) by the reaction of 3-chloromethyl-5-(3,4-dimethyl-phenyl)-2-methyl-pyridine hydrochloride (1:1) with 2-methylimidazole (5 eq.), using sodium hydride (3 eq.) as base followed by formation of the hydrochloride salt.

EXAMPLE 129

3-(4-Chloro-phenyl)-5-(2-methyl-imidazol-1-yl-methyl)-pyridine Hydrochloride (1:1)

A mixture of 3-bromo-5-(2-methyl-imidazol-1-ylmethyl)-pyridine (120 mg, 0.48 mmol), bis(triphenylphosphine) palladium (II) choride (10 mg, 0.01 mmol) and KOAc (140 mg, 0.14 mmol) were stirred in dioxane (10 ml) for 1 h at 20° C. 4-Chlorophenyl boronic acid (78 mg, 0.05 mmol) and 2N Na$_2$CO$_3$ solution (1.2 ml) were then added and the mixture heated to 100° C. for 7–24 h under an argon atmosphere. After cooling, the solvent was evaporated and 2N NaOH (5 ml) and AcOEt were added. The mixture was shaken and the aqueous phase separated and further extracted with AcOEt, the combined organic extracts were washed with brine then dried over Na$_2$SO$_4$, filtered and evaporated. The residue was chromatographed [silica, elution with CH$_2$Cl$_2$/(2M NH$_3$ in MeOH) 97:3)]. The product was dissolved in MeOH, cooled to 4° C. with stirring and treated with HC/EtOH (1.46 M 1.1 eq) for 45 min. Evaporation of the solvent and drying under high vacuum at 50° C. for 2 h afforded the title compound (98 mg, 64%) as a light brown solid. MS: m/e=284.2 (M+H$^+$).

Examples 130 to 142 were prepared according to the general procedure described in example 129.

EXAMPLE 130
3-(3,4-Dimethyl-phenyl)-5-(2-methyl-imidazol-1-yl-methyl)-pyridine Hydrochloride (1:1)

The title compound, MS: m/e=277 (M$^+$) was obtained as a light yellow foam (54% yield) by the reaction of 3-bromo-5-(2-methyl-imidazol-1-ylmethyl)-pyridine with 3,4-dimethylphenyl boronic acid.

EXAMPLE 131
3-(4-Fluoro-3-methyl-phenyl)-5-(2-methyl-imidazol-1-yl-methyl)-pyridine Hydrochloride (1:1)

The title compound, MS: m/e=281.1 (M$^+$) was obtained as a light brown foam (63% yield) by the reaction of 3-bromo-5-(2-methyl-imidazol-1-ylmethyl)-pyridine with 4-fluoro-3-methyl-phenyl boronic acid.

EXAMPLE 132
3-(3,4-Difluoro-phenyl)-5-(2-methyl-imidazol-1-yl-methyl)-pyridine Hydrochloride (1:1)

The title compound, MS: m/e=286.2 (M+H') was obtained as a light yellow foam (85% yield) by the reaction of 3-bromo-5-(2-methyl-imidazol-1-ylmethyl)-pyridine with 3,4-difluoro-phenylboronic acid.

EXAMPLE 133
3-(4-Fluoro-phenyl)-5-(2-methyl-imidazol-1-yl-methyl)-pyridine Hydrochloride (1:1)

The title compound, MS: m/e=268.3 (M+H$^+$) was obtained as a light yellow solid (90% yield) by the reaction of 3-bromo-5-(2-methyl-imidazol-1-ylmethyl)-pyridine with 4-fluoro phenylboronic acid.

EXAMPLE 134
3-(2-Methyl-imidazol-1-yl-methyl)-5-(3-trifluoromethyl-phenyl)-pyridine Hydrochloride (1:1)

The title compound, MS: m/e=318.3 (M+H$^+$) was obtained as a beige foam (74% yield) by the reaction of 3-bromo-5-(2-methyl-imidazol-1-ylmethyl)-pyridine with 3-trifluoromethyl phenylboronic acid.

EXAMPLE 135
3-(2-Methyl-imidazol-1-yl-methyl)-5-(4-trifluoromethyl-phenyl)-pyridine Hydrochloride (1:1)

The title compound, MS: m/e=318.3 (M+H$^+$) was obtained as a beige solid (77% yield) by the reaction of 3-bromo-5-(2-methyl-imidazol-1-yl-methyl)-pyridine with 4-trifluoromethyl phenylboronic acid.

EXAMPLE 136
3-(3-Chloro-4-methyl-phenyl)-5-(2-methyl-imidazol-1-yl-methyl)-pyridine Hydrochloride (1:1)

The title compound, MS: m/e=298.3 (M+H$^+$) was obtained as a beige solid (78% yield) by the reaction of 3-bromo-5-(2-methyl-imidazol-1-yl-methyl)-pyridine with 2-(3-chloro-4-methyl-phenyl)-4,4,5,5-tetramethyl [1,3,2]-dioxaborolane.

EXAMPLE 137
3-(4-Chloro-3-methyl-phenyl)-5-(2-methyl-imidazol-1-yl-methyl)-pyridine Hydrochloride (1:1)

The title compound, MS: m/e=298.3 (M+H$^+$) was obtained as a white solid (73% yield) by the reaction of 3-bromo-5-(2-methyl-imidazol-1-yl-methyl)-pyridine with 2-(4-chloro-3-methyl-phenyl)-4,4,5,5-tetramethyl[1,3,2]-dioxaborolane.

EXAMPLE 138
3-(2,3-Dihydro-benzofuran-5-yl)-5-(2-methyl-imidazol-1-yl-methyl)-pyridine Hydrochloride (1:1)

The title compound, MS: m/e=292.2 (M+H$^+$) was obtained as a light yellow foam (18% yield) by the reaction of 3-bromo-5-(2-methyl-imidazol-1-yl-methyl)-pyridine with 5-(4,4,5,5-tetramethyl[1,3,2]-dioxaborolan-2-yl)-2,3-dihydro-benzofuran.

EXAMPLE 139
3-Indan-5-yl-5-(2-methyl-imidazol-1-yl-methyl)-pyridine Hydrochloride (1:1)

The title compound, MS: m/e=289.1 (M$^+$) was obtained as a white solid (91% yield) by the reaction of 3-bromo-5-(2-methyl-imidazol-1-ylmethyl)-pyridine with 2-indan-5-yl-4,4,5,5-tetramethyl[1,3,2]-dioxaborolane.

EXAMPLE 140
3-(3-Chloro-4-fluoro-phenyl)-5-(2-methyl-imidazol-1-yl-methyl)-pyridine Hydrochloride The title compound, MS: m/e=301.1 (M$^+$) was obtained as a yellow solid (53% yield) by the reaction of 3-bromo-5-(2-methyl-imidazol-1-yl-methyl)-pyridine with 3-chloro-4-fluoro-phenyl boronic acid.

EXAMPLE 141
3-(4-Chloro-3-trifluoromethyl-phenyl)-5-(2-methyl-imidazol-1-yl-methyl)-pyridine Hydrochloride (1:1)

The title compound, MS: m/e=352.3 (M+H$^+$) was obtained as a beige foam (49% yield) by the reaction of 3-bromo-5-(2-methyl-imidazol-1-yl-methyl)-pyridine with 2-(4-chloro-3-trifluoromethyl-phenyl)-4,4,5,5-tetramethyl-[1,3,2] dioxaborolane.

EXAMPLE 142
3-(4-Fluoro-3-trifluoromethyl-phenyl)-5-(2-methyl-imidazol-1-yl-methyl)-pyridine Hydrochloride (1:1)

The title compound, MS: m/e=336.3 (M+H$^+$) was obtained as a white solid (60% yield) by the reaction of 3-bromo-5-(2-methyl-imidazol-1-ylmethyl)-pyridine with 2-(4-fluoro-3-trifluoromethyl-phenyl)-4,4,5,5-tetramethyl-[1,3,2] dioxaborolane.

EXAMPLE 143
1H-Imidazole, 2-ethyl-1-[1-3-(trifluoromethylthio)phenyl]-1H-imidazol-4-yl]methyl]-, Hydrochloride (1:2)

Following the general method described in example 10, the title compound was obtained as a white crystalline material by reaction of [1-(3-trifluoromethylsulfanyl-phenyl)-1H-imidazol-4-yl]-methanol first with thionylchloride and then with 2-ethylimidazole and sodium hydride followed by chromatography and crystallization of the hydrochloride salt. Mp. 234–236° C. (MeOH/Et$_2$O), MS: m/e=353(M+H$^+$).

EXAMPLE 144
1H-Imidazole, 2-methyl-1-[[1-[3-(trifluoromethylthio)phenyl]-1H-imidazol-4-yl]methyl]-, Hydrochloride (1:2)

Following the general method described in example 10, the title compound was obtained as a white crystalline material by reaction of [1-(3-trifluoromethylsulfanyl-phenyl)-1H-imidazol-4-yl]-methanol first with thionylchloride and then with 2-methylimidazole and sodium hydride followed by chromatography and crystallization of the hydrochloride salt. Mp. 169–170° C. (MeOH/Et$_2$O), MS: m/e=339(M+H$^+$).

EXAMPLE 145
4-Imidazol-1-ylmethyl-1-(3-methylsulfanyl-phenyl)-1H-imidazole Hydrochloride (1:2)

Following the general method described in example 10, the title compound was obtained as a white crystalline material by reaction of [1-(3-trifluoromethylsulfanyl-phenyl)-1H-imidazol-4-yl]-methanol first with thionylchloride and then with imidazole and sodium hydride followed by chromatography and crystallization of the hydrochloride salt. Mp. 213–215° C. (MeOH/Et$_2$O), MS: m/e=325 (M+H$^+$).

EXAMPLE 146
1H-Imidazole, 1-[[1-[3-(1,1-difluoroethyl)phenyl]-1H-imidazol-4-yl]methyl]-2-ethyl-, Hydrochloride (1:2)

Following the general method described in example 10, the title compound was obtained as an off-white crystalline material by reaction of {1-[3-(1,1-difluoro-ethyl)-phenyl]-1H-imidazol-4-yl}-methanol first with thionylchloride and then with 2-ethylimidazole and sodium hydride followed by chromatography and crystallization of the hydrochloride salt. Mp. 130–134° C. dec.(MeOH/Et$_2$O), MS: m/e=317 (M+H$^+$).

EXAMPLE 147
1H-Imidazole, 1-[[1-[3-(1,1-difluoroethyl)phenyl]-1H-imidazol-4-yl]methyl]-2-methyl-, Hydrochloride (1:2)

Following the general method described in example 10, the title compound was obtained as an off-white crystalline material by reaction of {1-[3-(1,1-difluoro-ethyl)-phenyl]-1H-imidazol-4-yl}-methanol first with thionylchloride and then with 2-methylimidazole and sodium hydride followed by chromatography and crystallization of the hydrochloride salt. Mp.>200° C. dec. (MeOH/Et$_2$O), MS: m/e=303 (M+H$^+$).

EXAMPLE 148
1-[3-(1,1-Difluoroethyl)-phenyl]-4-imidazol-1-ylmethyl-1H-imidazole Hydrochloride (1:2)

Following the general method described in example 10, the title compound was obtained as an off-white crystalline material by reaction of {1-[3-(1,1-difluoro-ethyl)-phenyl]-1H-imidazol-4-yl}-methanol first with thionylchloride and then with imidazole and sodium hydride followed by chromatography and crystallization of the hydrochloride salt. Mp.>200° C. dec. (MeOH/Et$_2$O), MS: m/e=303 (M+H$^+$).

EXAMPLE 149
1H-Imidazole, 1-[[1-[3-(1,1-difluoroethyl)-4-fluorophenyl]-1H-imidazol-4-yl]methyl]-2-methyl-, Hydrochloride (1:2)

Following the general method described in example 10, the title compound was obtained as an off-white crystalline material by reaction of {1-[3-(1,1-difluoro-ethyl)-4-fluoro-phenyl]-1H-imidazol-4-yl}-methanol first with thionylchloride and then with 2-methylimidazole and sodium hydride followed by chromatography and crystallization of the hydrochloride salt. Mp.>200° C. dec. (MeOH/Et$_2$O), MS: m/e=321 (M+H$^+$).

EXAMPLE 150
1-[3-(1,1-Difluoro-ethyl)-4-fluoro-phenyl]-4-imidazol-1-ylmethyl-1H-imidazole Hydrochloride (1:2)

Following the general method described in example 10, the title compound was obtained as an off-white crystalline material by reaction of {1-[3-(1,1-difluoro-ethyl)-4-fluoro-phenyl]-1H-imidazol-4-yl}-methanol first with thionylchloride and then with imidazole and sodium hydride followed by chromatography and crystallization of the hydrochloride salt. Mp.>200° C. dec. (MeOH/Et$_2$O), MS: m/e=307 (M+H$^+$).

EXAMPLE 151
1H-Imidazole, 1-[[1-[3-(1,1-difluoroethyl)-4-fluorophenyl]-1H-imidazol-4-yl]methyl]-2-ethyl-, Hydrochloride (1:2)

Following the general method described in example 10, the title compound was obtained as an off-white crystalline material by reaction of {1-[3-(1,1-difluoro-ethyl)-4-fluoro-phenyl]-1H-imidazol-4-yl}-methanol first with thionylchloride and then with 2-ethylimidazole and sodium hydride followed by chromatography and crystallization of the hydrochloride salt. Mp.>200° C. dec. (MeOH/Et$_2$O), MS: m/e=335 (M+H$^+$).

EXAMPLE 152
1H-Imidazole, 1-[[1-(3-isopropylphenyl)-1H-imidazol-4-yl]methyl]-2-methyl-, Hydrochloride (1:2)

Following the general method described in example 10, the title compound was obtained as an off-white crystalline material by reaction of [1-(3-isopropyl-phenyl)-1H-imidazol-4-yl]-methanol first with thionylchloride and then with 2-methylimidazole and sodium hydride followed by chromatography and crystallization of the hydrochloride salt. Mp.>200° C. dec. (MeOH/Et$_2$O), MS: m/e=281 (M+H$^+$).

EXAMPLE 153
1H-Imidazole, 2-ethyl-1-[[1 (3-isopropyphenyl)-1H-imidazol-4-yl]methyl]-, Hydrochloride (1:2)

Following the general method described in example 10, the title compound was obtained as an off-white crystalline material by reaction of [1-(3-isopropyl-phenyl)-1H-imidazol-4-yl]-methanol first with thionylchloride and then with 2-ethylimidazole and sodium hydride followed by chromatography and crystallization of the hydrochloride salt. Mp.>200° C. dec. (MeOH/Et$_2$O), MS: m/e=295 (M+H$^+$).

EXAMPLE 154
4-Imidazol-1-ylmethyl-1-(3-isopropyl-phenyl)-1H-imidazole Hydrochloride (1:2)

Following the general method described in example 10, the title compound was obtained as an off-white crystalline material by reaction of [1-(3-isopropyl-phenyl)-1H-imidazol-4-yl]-methanol first with thionylchloride and then with imidazole and sodium hydride followed by chromatography and crystallization of the hydrochloride salt. Mp. 200–206° C. (MeOH/Et$_2$O), MS: m/e=267 (M+H$^+$).

EXAMPLE 155
1H-Imidazole, 2-methyl-1-[[1-(naphtalen-2-yl)-1H-imidazol-4-yl]methyl]-, Hydrochloride (1:2)

Following the general method described in example 10, the title compound was obtained as a white crystalline material by reaction of (1-naphthalen-2-yl-1H-imidazol-4-yl)-methanol first with thionylchloride and then with 2-methylimidazole and sodium hydride followed by chromatography and crystallization of the hydrochloride salt. Mp. 247–248° C. (MeOH/Et$_2$O), MS: m/e=288 (M$^+$).

EXAMPLE 156
1H-Imidazole, 1-[[1-(3-bromo-4-fluorophenyl)-1H-imidazol-4-yl]methyl]-2-ethyl-, Hydrochloride (1:2)

Following the general method described in example 10, the title compound was obtained as a white crystalline material by reaction of [1-(3-bromo-4-fluoro-phenyl)-1H-imidazol-4-yl]-methanol first with thionylchloride and then with 2-ethylimidazole and sodium hydride followed by chromatography and crystallization of the hydrochloride salt. Mp. 238–239 C (MeOH/Et$_2$O), MS: m/e=349 (M+H$^+$).

EXAMPLE 157

1H-Imidazole, 1-[[1-(3-bromo-4-fluorophenyl)-1H-imidazol-4-yl]methyl]-2-methyl-, Hydrochloride (1:2)

Following the general method described in example 10, the title compound was obtained as a white crystalline material by reaction of [1-(3-bromo-4-fluoro-phenyl)-1H-imidazol-4-yl]-methanol first with thionylchloride and then with 2-methylimidazole and sodium hydride followed by chromatography and crystallization of the hydrochloride salt. Mp. 232–233° C. (MeOH/Et$_2$O), MS: m/e=335 (M+H$^+$)

EXAMPLE 158

1-(3-Bromo-4-fluoro-phenyl)-4-imidazol-1-ylmethyl-1H-imidazole Hydrochloride (1:2)

Following the general method described in example 10, the title compound was obtained as a white crystalline material by reaction of [1-(3-bromo-4-fluoro-phenyl)-1H-imidazol-4-yl]-methanol first with thionylchloride and then with imidazole and sodium hydride followed by chromatography and crystallization of the hydrochloride salt. Mp. 229–230° C. (MeOH/Et$_2$O), MS: m/e=321 (M+H$^+$).

EXAMPLE 159

1H-Imidazole, 1-[[1-(3-ethylphenyl)-1H-imidazol-4-yl]methyl]-2-methyl-, Hydrochloride (1:2)

Following the general method described in example 10, the title compound was obtained as an off-white crystalline material by reaction of [1-(3-ethyl-phenyl)-1H-imidazol-4-yl]-methanol first with thionylchloride and then with 2-methylimidazole and sodium hydride followed by chromatography and crystallization of the hydrochloride salt. Mp.>200° C. dec. (MeOH/Et$_2$O), MS: m/e=267 (M+H$^+$).

EXAMPLE 160

1H-Imidazole, 2-ethyl-1-[[1-(3-ethylphenyl)-1H-imidazol-4-yl]methyl]-, Hydrochloride (1:2)

Following the general method described in example 10, the title compound was obtained as an off-white crystalline material by reaction of [1-(3-ethyl-phenyl)-1H-imidazol-4-yl]-methanol first with thionylchloride and then with 2-ethylimidazole and sodium hydride followed by chromatography and crystallization of the hydrochloride salt. Mp.>200° C. dec. (MeOH/Et$_2$O), MS: m/e=281 (M+H$^+$).

EXAMPLE 161

1-(3-Ethyl-phenyl)-4-imidazol-1-ylmethyl-1H-imidazole Hydrochloride (1:2)

Following the general method described in example 10, the title compound was obtained as an off-white crystalline material by reaction of [1-(3-ethyl-phenyl)-1H-imidazol-4-yl]-methanol first with thionylchloride and then with imidazole and sodium hydride followed by chromatography and crystallization of the hydrochloride salt. Mp.>190° C. dec. (MeOH/Et$_2$O), MS: m/e=253 (M+H$^+$).

EXAMPLE 162

1H-Imidazole, 1-[[1-(3-cyclopropylphenyl)-1H-imidazol-4-yl]methyl]-2-methyl-, Hydrochloride (1:2)

Following the general method described in example 10, the title compound was obtained as a light brown crystalline material by reaction of [1-(3-cyclopropyl-phenyl)-1H-imidazol-4-yl]-methanol first with thionylchloride and then with 2-methylimidazole and sodium hydride followed by chromatography and crystallization of the hydrochloride salt. Mp. 174–175° C. (MeOH/Et$_2$O), MS: m/e=279 (M+H$^+$).

EXAMPLE 163

1H-Imidazole, 1-[[1-(3-difluoromethyl-4-fluorophenyl)-1H-imidazol-4-yl]methyl]-2-methyl-, Hydrochloride (1:2)

Following the general method described in example 10, the title compound was obtained as a white crystalline material by reaction of [1-(3-difluoromethyl-4-fluorophenyl)-1H-imidazol-4-yl]-methanol first with thionylchloride and then with 2-methylimidazole and sodium hydride followed by chromatography and crystallization of the hydrochloride salt. Mp. 223–225° C. dec. (MeOH/Et$_2$O), MS: m/e=306 (M$^+$).

EXAMPLE 164

1H-Imidazole, 1-[[1-(3-difluoromethyl-4-fluorophenyl)-1H-imidazol-4-yl]methyl]-2-ethyl-, Hydrochloride (1:2)

Following the general method described in example 10, the title compound was obtained as a white crystalline material by reaction of [1-(3-difluoromethyl-4-fluorophenyl)-1H-imidazol-4-yl]-methanol first with thionylchloride and then with 2-ethylimidazole and sodium hydride followed by chromatography and crystallization of the hydrochloride salt. Mp. 229–232° C. (MeOH/Et$_2$O), MS: m/e=320 (M$^+$).

EXAMPLE 165

1-(3-Difluoromethyl-4-fluoro-phenyl)-4-imidazol-1-ylmethyl-1H-imidazole Hydrochloride (1:2)

Following the general method described in example 10, the title compound was obtained as a white crystalline material by reaction of [1-(3-difluoromethyl-4-fluoro-phenyl)-1H-imidazol-4-yl]-methanol first with thionylchloride and then with imidazole and sodium hydride followed by chromatography and crystallization of the hydrochloride salt. Mp. 239–241° C. (MeOH/Et$_2$O), MS: m/e=292 (M$^+$).

EXAMPLE 166

1H-Imidazole, 2-ethyl-1-[[1-[3-(methylthio)phenyl]-1H-imidazol-4-yl]methyl]-, Hydrochloride (1:2)

Following the general method described in example 10, the title compound was obtained as an off-white crystalline material by reaction of [-(3-methylsulfanyl-phenyl)-1H-imidazol-4-yl]-methanol first with thionylchloride and then with 2-ethylimidazole and sodium hydride followed by chromatography and crystallization of the hydrochloride salt. Mp.>200° C. dec. (MeOH/Et$_2$O), MS: m/e=299 (M+H$^+$).

EXAMPLE 167

1H-Imidazole, 2-methyl-1-[[1-[3-(methylthio)phenyl]-1H-imidazol-4-yl]methyl]-, Hydrochloride (1:2)

Following the general method described in example 10, the title compound was obtained as an off-white crystalline material by reaction of [1-(3-methylsulfanyl-phenyl)-1H-imidazol-4-yl]-methanol first with thionylchloride and then with 2-methylimidazole and sodium hydride followed by chromatography and crystallization of the hydrochloride salt. Mp.>200° C. dec. (MeOH/Et$_2$O), MS: m/e=285 (M+H$^+$).

EXAMPLE 168

4-Imidazol-1-ylmethyl-1-(3-methylsulfanyl-phenyl)-1H-imidazole Hydrochloride (1:2)

Following the general method described in example 10, the title compound was obtained as an off-white crystalline material by reaction of [1-(3-methylsulfanyl-phenyl)-1H-imidazol-4-yl]-methanol first with thionylchloride and then with imidazole and sodium hydride followed by chromatography and crystallization of the hydrochloride salt. Mp.>200° C. dec. (MeOH/Et$_2$O), MS: m/e=271 (M+H$^+$).

EXAMPLE 169

1H-Imidazole, 2-ethyl-1-[[1-[3-(trifluoromethoxy)phenyl]-1H-imidazol-4-yl]methyl]-, Hydrochloride (1:2)

Following the general method described in example 10, the title compound was obtained as a white crystalline material by reaction of [1-(3-trifluoromethoxy-phenyl)-1H-imidazol-4-yl]-methanol first with thionylchloride and then with 2-ethylimidazole and sodium hydride followed by chromatography and crystallization of the hydrochloride salt. Mp. 237–239° C. (MeOH/Et$_2$O), MS: m/e=336 (M$^+$).

EXAMPLE 170

1H-Imidazole, 2-methyl-1-[[-1[3-(trifluoromethoxy)phenyl]-1H-imidazol-4-yl]methyl]-, Hydrochloride (1:2)

Following the general method described in example 10, the title compound was obtained as a white crystalline material by reaction of [1-(3-trifluoromethoxy-phenyl)-1H-imidazol-4-yl]-methanol first with thionylchloride and then with 2-methylimidazole and sodium hydride followed by chromatography and crystallization of the hydrochloride salt. Mp. 221–223° C. (MeOH/Et$_2$O), MS: m/e=322 (M$^+$).

EXAMPLE 171

4-Imidazol-1-ylmethyl-1-(3-trifluoromethoxy-phenyl)-1H-imidazole Hydrochloride (1:2)

Following the general method described in example 10, the title compound was obtained as a white crystalline material by reaction of [1-(3-trifluoromethoxy-phenyl)-1H-imidazol-4-yl]-methanol first with thionylchloride and then with imidazole and sodium hydride followed by chromatography and crystallization of the hydrochloride salt. Mp. 233–234° C. (MeOH/Et$_2$O), MS: m/e=308 (M$^+$).

EXAMPLE 172

1H-Imidazole, 2-methyl-1-[[1-(3-vinylphenyl)-1H-imidazol-4-yl]methyl]-, Hydrochloride (1:2)

Following the general method described in example 10, the title compound was obtained as a white crystalline material by reaction of [1-(3-vinyl-phenyl)-1H-imidazol-4-yl]-methanol first with thionylchloride and then with 2-methylimidazole and sodium hydride followed by chromatography and crystallization of the hydrochloride salt. Mp. 207–208° C. (MeOH/Et$_2$O), MS: m/e=265 (M+H$^+$).

EXAMPLE 173

1H-Imidazole, 1-[[1-(3-chlorophenyl)-1H-imidazol-4-yl]methyl]-2-methyl-, Hydrochloride (1:2)

Following the general method described in example 10, the title compound was obtained as an off-white crystalline material by reaction of [1-(3-chloro-phenyl)-1H-imidazol-4-yl]-methanol first with thionylchloride and then with 2-methylimidazole and sodium hydride followed by chromatography and crystallization of the hydrochloride salt. Mp.>200° C. dec. (MeOH/Et$_2$O), MS: m/e=273 (M+H$^+$).

EXAMPLE 174

1H-Imidazole, 1-[[1-(3-chlorophenyl)-1H-imidazol-4-yl]methyl]-2-ethyl-, Hydrochloride Following the general method described in example 10, the title compound was obtained as an off-white crystalline material by reaction of [1-(3-chloro-phenyl)-1H-imidazol-4-yl]-methanol first with thionylchloride and then with 2-ethylimidazole and sodium hydride followed by chromatography and crystallization of the hydrochloride salt. Mp.>200° C. dec. (MeOH/Et$_2$O), MS: m/e=287 (M+H$^+$).

EXAMPLE 175

1-(3-Chloro-phenyl)-4-imidazol-1-ylmethyl-1H-imidazole Hydrochloride (1:2)

Following the general method described in example 10, the title compound was obtained as an off-white crystalline material by reaction of [f-(3-chloro-phenyl)-1H-imidazol-4-yl]-methanol first with thionylchloride and then with imidazole and sodium hydride followed by chromatography and crystallization of the hydrochloride salt. Mp.>200° C. dec. (MeOH/Et$_2$O), MS: m/e=259 (M+H$^+$).

EXAMPLE 176

1H-Imidazole, 1-[[1-(3-iodophenyl)-1H-imidazol-4-yl]methyl]-2-methyl-, Hydrochloride (1:2)

Following the general method described in example 10, the title compound was obtained as an off-white crystalline material by reaction of [1-(3-iodo-phenyl)-1H-imidazol-4-yl]-methanol first with thionylchloride and then with 2-methylimidazole and sodium hydride followed by chromatography and crystallization of the hydrochloride salt. Mp.>222° C. dec. (MeOH/Et$_2$O), MS: m/e=365 (M+H$^+$).

EXAMPLE 177

1H-Imidazole, 2-ethyl-1-[[1-[3-fluoro-5(trifluoromethyl)phenyl]-1H-imidazol-4-yl]methyl]-, Hydrochloride (1:2)

Following the general method described in example 10, the title compound was obtained as a white crystalline material by reaction of [1-(3-fluoro-5-trifluoromethyl-phenyl)-1H-imidazol-4-yl]-methanol first with thionylchloride and then with 2-ethylimidazole and sodium hydride followed by chromatography and crystallization of the hydrochloride salt. Mp. 243–244° C. (MeOH/Et$_2$O), MS: m/e=338 (M$^+$).

EXAMPLE 178

1H-Imidazole, 1-[[1-[3-fluoro-5(trifluoromethyl)phenyl]-1H-imidazol-4-yl]methyl]-2-methyl-, Hydrochloride (1:2)

Following the general method described in example 10, the title compound was obtained as a white crystalline material by reaction of [1-(3-fluoro-5-trifluoromethyl-phenyl)-1H-imidazol-4-yl]-methanol first with thionylchloride and then with 2-methylimidazole and sodium hydride followed by chromatography and crystallization of the hydrochloride salt. Mp.>250° C. (MeOH/Et$_2$O), MS: m/e=325 (M+H$^+$).

EXAMPLE 179

1-(3-Fluoro-5-trifluoromethyl-phenyl)-4-imidazol-1-ylmethyl-1H-imidazole Hydrochloride (1:2)

Following the general method described in example 10, the title compound was obtained as a white crystalline material by reaction of [1-(3-fluoro-5-trifluoromethyl-phenyl)-1H-imidazol-4-yl]-methanol first with thionylchloride and then with imidazole and sodium hydride followed by chromatography and crystallization of the hydrochloride salt. Mp. 233–234° C. (MeOH/Et$_2$O), MS: m/e=310 (M$^+$).

EXAMPLE 180

1H-Imidazole, 1-[[1-[3-methoxy-5(trifluoromethyl)phenyl]-1H-imidazol-4-yl]methyl]-2-methyl-, Hydrochloride (1:2)

Following the general method described in example 10, the title compound was obtained as a white crystalline material by reaction of [1-(3-methoxy-5-trifluoromethyl-phenyl)-1H-imidazol-4-yl]-methanol first with thionylchloride and then with 2-methylimidazole and sodium hydride followed by chromatography and crystallization of the hydrochloride salt. Mp. 246–247° C. (MeOH/Et$_2$O), MS: m/e=337 (M+H$^+$).

EXAMPLE 181
1H-Imidazole, 2-ethyl-1-[[1-[3-methoxy-5(trifluoromethyl)phenyl]-1H-imidazol-4-yl]methyl]-, Hydrochloride (1:2)

Following the general method described in example 10, the title compound was obtained as a white crystalline material by reaction of [1-(3-fluoro-5-trifluoromethyl-phenyl)-1H-imidazol-4-yl]-methanol first with thionylchloride and then with 2-ethylimidazole and sodium hydride followed by chromatography and crystallization of the hydrochloride salt. Mp. 245–246° C. (MeOH/Et$_2$O), MS: m/e=350 (M$^+$).

EXAMPLE 182
4-Imidazol-1-ylmethyl-1-(3-methoxy-5-trifluoromethyl-phenyl)-1H-imidazole Hydrochloride (1:2)

Following the general method described in example 10, the title compound was obtained as a white crystalline material by reaction of [1-(3-fluoro-5-trifluoromethyl-phenyl)-1H-imidazol-4-yl]-methanol first with thionylchloride and then with imidazole and sodium hydride followed by chromatography and crystallization of the hydrochloride salt. Mp. 244–246° C. (MeOH/Et$_2$O), MS: m/e=322 (M$^+$).

EXAMPLE 183
1H-Imidazole, 1-[[1-(3-tert-butylphenyl)-1H-imidazol-4-yl]methyl]-2-methyl-, Hydrochloride (1:2)

Following the general method described in example 10, the title compound was obtained as an off-white crystalline material by reaction of [1-(3-tert-butyl-phenyl)-1H-imidazol-4-yl]-methanol first with thionylchloride and then with 2-methylimidazole and sodium hydride followed by chromatography and crystallization of the hydrochloride salt. Mp.>200° C. dec. (MeOH/Et$_2$O), MS: m/e=295 (M+H$^+$).

EXAMPLE 184
1H-Imidazole, 1-[[1-(3-tert-butylphenyl)-1H-imidazol-4-yl]methyl]-2-ethyl-, Hydrochloride (1:2)

Following the general method described in example 10, the title compound was obtained as a light brown crystalline material by reaction of [1-(3-tert-butyl-phenyl)-1H-imidazol-4-yl]-methanol first with thionylchloride and then with 2-ethylimidazole and sodium hydride followed by chromatography and crystallization of the hydrochloride salt. Mp. 205° C. dec. (MeOH/Et$_2$O), MS: m/e=309 (M+H$^+$).

EXAMPLE 185
1-(3-tert-Butyl-phenyl)-4-imidazol-1-ylmethyl-1H-imidazole Hydrochloride (1:2)

Following the general method described in example 10, the title compound was obtained as an off-white crystalline material by reaction of [1-(3-tert-butyl-phenyl)-1H-imidazol-4-yl]-methanol first with thionylchloride and then with imidazole and sodium hydride followed by chromatography and crystallization of the hydrochloride salt. Mp.>200° C. dec. (MeOH/Et$_2$O), MS: m/e=281 (M+H$^+$).

EXAMPLE 186
1H-Imidazole, 1-[[1-[3-chloro-4(trifluoromethoxy)phenyl]-1H-imidazol-4-yl]methyl]-2-methyl-, Hydrochloride (1:2)

Following the general method described in example 10, the title compound was obtained as a white crystalline material by reaction of [1-(3-chloro-4-trifluoromethoxy-phenyl)-1H-imidazol-4-yl]-methanol first with thionylchloride and then with 2-methylimidazole and sodium hydride followed by chromatography and crystallization of the hydrochloride salt. Mp. 221–222° C. (MeOH/Et$_2$O), MS: m/e=357 (M+H$^+$).

EXAMPLE 187
1H-Imidazole, 1-[[1-[3-chloro-4(trifluoromethoxy)phenyl]-1H-imidazol-4-yl]methyl]-2-ethyl-, Hydrochloride (1:2)

Following the general method described in example 10, the title compound was obtained as a white crystalline material by reaction of [f-(3-chloro-4-trifluoromethoxy-phenyl)-1H-imidazol-4-yl]-methanol first with thionylchloride and then with 2-ethylimidazole and sodium hydride followed by chromatography and crystallization of the hydrochloride salt. Mp.>250° C. (MeOH/Et$_2$O), MS: m/e=370 (M$^+$).

EXAMPLE 188
1-(3-Chloro-4-trifluoromethoxy-phenyl)-4-imidazol-1-ylmethyl-1H-imidazole Hydrochloride (1:2)

Following the general method described in example 10, the title compound was obtained as a white crystalline material by reaction of [1-(3-chloro-4-trifluoromethoxy-phenyl)-1H-imidazol-4-yl]-methanol first with thionylchloride and then with imidazole and sodium hydride followed by chromatography and crystallization of the hydrochloride salt. Mp. 212–213° C. (MeOH/Et$_2$O), MS: m/e=342 (M$^+$).

EXAMPLE 189
1H-Imidazole, 1-[[1-[3-(difluoromethoxy)phenyl]-1H-imidazol-4-yl]methyl]-2-ethyl-, Hydrochloride (1:2)

Following the general method described in example 10, the title compound was obtained as a white crystalline material by reaction of [1-(3-difluoromethoxy-phenyl)-1H-imidazol-4-yl]-methanol first with thionylchloride and then with 2-ethylimidazole and sodium hydride followed by chromatography and crystallization of the hydrochloride salt. Mp. 216–217 C (MeOH/Et$_2$O), MS: m/e=319 (M+H$^+$).

EXAMPLE 190
1H-Imidazole, 1-[[1-[3-(difluoromethoxy)phenyl]-1H-imidazol-4-yl]methyl]-2-methyl-, Hydrochloride (1:2)

Following the general method described in example 10, the title compound was obtained as a white crystalline material by reaction of [1-(3-difluoromethoxy-phenyl)-1H-imidazol-4-yl]-methanol first with thionylchloride and then with 2-methylimidazole and sodium hydride followed by chromatography and crystallization of the hydrochloride salt. Mp. 220–222° C. (MeOH/Et$_2$O), MS: m/e=305 (M+H$^+$).

EXAMPLE 191
1-(3-Difluoromethoxy-phenyl)-4-imidazol-1-ylmethyl-1H-imidazole Hydrochloride (1:2)

Following the general method described in example 10, the title compound was obtained as a white crystalline material by reaction of [1-(3-difluoromethoxy-phenyl)-1H-imidazol-4-yl]-methanol first with thionylchloride and then with imidazole and sodium hydride followed by chromatography and crystallization of the hydrochloride salt. Mp. 205–206° C. (MeOH/Et$_2$O), MS: m/e=291 (M+H$^+$).

EXAMPLE 192
1H-Imidazole, 1-[[1-(3-bromophenyl)-1H-imidazol-4-yl]methyl]-2-methyl-, Hydrochloride (1:2)

Following the general method described in example 10, the title compound was obtained as a light brown crystalline material by reaction of [1-(3-bromo-phenyl)-1H-imidazol-4-yl]-methanol first with thionylchloride and then with 2-methylimidazole and sodium hydride followed by chromatography and crystallization of the hydrochloride salt. Mp. 205–207° C. (MeOH/Et$_2$O), MS: m/e=317 (M+H$^+$).

EXAMPLE 193
1H-Imidazole, 1-[[1-[3-(difluoromethyl)phenyl]-1H-imidazol-4-yl]methyl]-2-ethyl-, Hydrochloride (1:2)

Following the general method described in example 10, the title compound was obtained as a white crystalline material by reaction of [1-(3-difluoromethyl-phenyl)-1H-imidazol-4-yl]-methanol first with thionylchloride and then with 2-ethylimidazole and sodium hydride followed by chromatography and crystallization of the hydrochloride salt. Mp. 219–220° C. (MeOH/Et$_2$O), MS: m/e=303 (M+H$^+$).

EXAMPLE 194
1H-Imidazole, 1-[[1-[3-(difluoromethyl)phenyl]-1H-imidazol-4-yl]methyl]-2-methyl-, Hydrochloride (1:2)

Following the general method described in example 10, the title compound was obtained as a white crystalline material by reaction of [1-(3-difluoromethyl-phenyl)-1H-imidazol-4-yl]-methanol first with thionylchloride and then with 2-methylimidazole and sodium hydride followed by chromatography and crystallization of the hydrochloride salt. Mp. 195–196° C. (MeOH/Et$_2$O), MS: m/e=289 (M+H$^+$).

EXAMPLE 195
1-(3-Difluoromethyl-phenyl)-4-imidazol-1-ylmethyl-1H-imidazole Hydrochloride (1:2)

Following the general method described in example 10, the title compound was obtained as a white crystalline material by reaction of [1-(3-difluoromethyl-phenyl)-1H-imidazol-4-yl]-methanol first with thionylchloride and then with imidazole and sodium hydride followed by chromatography and crystallization of the hydrochloride salt. Mp. 216–217 C (MeOH/Et$_2$O), MS: m/e=275 (M+H$^+$).

EXAMPLE 196
{1-[1-(3,4-Dichloro-phenyl)-1H-imidazol-4-ylmethyl]-1H-imidazol-2-yl}-methyl-amine Hydrochloride (1:1)

A suspension of 1-[1-(3,4-dichloro-phenyl)-1H-imidazol-4-ylmethyl]-1H-imidazol-2-ylamine (0.7 g, 2.3 mmol) in triethyl orthoformate (10 ml) was stirred under reflux for 2 h. The reaction mixture was evaporated to dryness, dissolved in ethanol (10 ml) and cooled in an ice bath. Sodium borohydride (0.091 g, 2.4 mmol) was added and the mixture was allowed to slowly reach 20° C. After 18 h AcOEt and brine was added and the organic phase was separated, dried (Na$_2$SO$_4$) and concentrated. After chromatography [silica, elution with gradient CH$_2$Cl$_2$ to 100% (CH$_2$Cl$_2$/MeOH/aq. NH$_4$OH=90:10:1)] the free base of the title compound was obtained. It was crystallized as the off-white hydrochloride salt (0.25 g, 16%). Mp.>250° C. (MeOH/Et$_2$O), MS: m/e= 322 (M+H$^+$).

EXAMPLE 197
[3-(3,4-Dichloro-phenyl)-5-(2-methylamino-imidazol-1-ylmethyl)-3H-imidazol-4-yl]-methanol Hydrochloride (1:1)

A solution of {1-[1-(3,4-dichloro-phenyl)-1H-imidazol-4-ylmethyl]-1H-imidazol-2-yl}-methyl-amine (0.60 g, 1.7 mmol) in acetic acid (7 ml) and aqueous formaldehyde (2 ml of a 37% solution) was stirred at 20° C. for 96 h. The reaction mixture was evaporated to dryness and chromatographed [silica, elution with gradient CH$_2$Cl$_2$ to 50% (CH$_2$Cl$_2$/MeOH/aq. NH$_4$OH=90:10:1)] to obtain the free base of the title compound. It was crystallized as the off-white hydrochloride salt (0.030 g, 5%). Mp.>180° C. dec. (MeOH/Et$_2$O), MS: m/e=352 (M+H$^+$).

EXAMPLE 198
1H-Imidazole, 1-[[1-(3-bromo-5-fluorophenyl)-1H-imidazol-4-yl]methyl]-2-methyl-, Hydrochloride (1:2)

Following the general method described in example 10, the title compound was obtained as an off-white crystalline material by reaction of [1-(3-bromo-5-fluoro-phenyl)-1H-imidazol-4-yl]-methanol first with thionylchloride and then with 2-methylimidazole and sodium hydride followed by chromatography and crystallization of the hydrochloride salt. Mp.>200° C. dec. (MeOH/Et$_2$O), MS: m/e=335 (M+H$^+$).

EXAMPLE 199
1H-Imidazole, 1-[[1-(3-bromo-5-fluorophenyl)-1H-imidazol-4-yl]methyl]-2-ethyl-, Hydrochloride (1:2)

Following the general method described in example 10, the title compound was obtained as an off-white crystalline material by reaction of [1-(3-bromo-5-fluoro-phenyl)-1H-imidazol-4-yl]-methanol first with thionylchloride and then with 2-ethylimidazole and sodium hydride followed by chromatography and crystallization of the hydrochloride salt. Mp.>200° C. dec. (MeOH/Et$_2$O), MS: m/e=349 (M+H$^+$).

EXAMPLE 200
1-(3-Bromo-5-fluoro-phenyl)-4-imidazol-1-ylmethyl-1H-imidazole Hydrochloride (1:2)

Following the general method described in example 10, the title compound was obtained as an off-white crystalline material by reaction of [1-(3-bromo-5-fluoro-phenyl)-1H-imidazol-4-yl]-methanol first with thionylchloride and then with imidazole and sodium hydride followed by chromatography and crystallization of the hydrochloride salt. Mp.>200° C. dec. (MeOH/Et$_2$O), MS: m/e=321 (M+H$^+$).

EXAMPLE 201
1H-Imidazole, 1-[[1-(2,2-difluoro-1,3-benzodioxol-5-yl)-1H-imidazol-4-yl]methyl]-2-ethyl-, Hydrochloride (1:2)

Following the general method described in example 10, the title compound was obtained as a white crystalline material by reaction of [1-(2,2-difluoro-benzo[1,3]dioxol-5-yl)-1H-imidazol-4-yl]-methanol first with thionylchloride and then with 2-ethylimidazole and sodium hydride followed by chromatography and crystallization of the hydrochloride salt. Mp. 237–239° C. dec. (MeOH/Et$_2$O), MS: m/e=333 (M+H$^+$).

EXAMPLE 202
1H-Imidazole, 1-[[1-(2,2-difluoro-1,3-benzodioxol-5-yl)-1H-imidazol-4-yl]methyl]-2-methyl-, Hydrochloride (1:2)

Following the general method described in example 10, the title compound was obtained as a white crystalline material by reaction of [1-(2,2-difluoro-benzo[1,3]dioxol-5-yl)-1H-imidazol-4-yl]-methanol first with thionylchloride and then with 2-methylimidazole and sodium hydride followed by chromatography and crystallization of the hydrochloride salt. Mp.>250° C. (MeOH/Et$_2$O), MS: m/e=319 (M+H$^+$).

EXAMPLE 203
1-(2,2-Difluoro-benzo[1,3]dioxol-5-yl)-4-imidazol-1-ylmethyl-1H-imidazole Hydrochloride (1:2)

Following the general method described in example 10, the title compound was obtained as a white crystalline material by reaction of [1-(2,2-difluoro-benzo[1,3]dioxol-5-yl)-1H-imidazol-4-yl]-methanol first with thionylchloride and then with imidazole and sodium hydride followed by chromatography and crystallization of the hydrochloride salt. Mp. 245–246° C. (MeOH/Et$_2$O), MS: m/e=319 (M+H$^+$).

EXAMPLE 204
2-[4-(2-Methyl-imidazol-1-ylmethyl)-imidazol-1-yl]-quinoline

Following the general method described in example 10, the title compound was obtained as an off-white crystalline material by reaction of (1-quinolin-2-yl-1H-imidazol-4-yl)-methanol first with thionylchloride and then with 2-methylimidazole and sodium hydride followed by chromatography and crystallization of the free base. Mp. 160° C. (AcOEt/hexane), MS: m/e=290 (M+H$^+$).

EXAMPLE 205
2-[4-(2-Ethyl-imidazol-1-ylmethyl)-imidazol-1-yl]-quinoline

Following the general method described in example 10, the title compound was obtained as an off-white crystalline material by reaction of (1-quinolin-2-yl-1H-imidazol-4-yl)-methanol first with thionylchloride and then with 2-ethylimidazole and sodium hydride followed by chromatography and crystallization of the free base. Mp.>80° C. dec. (AcOEt/hexane), MS: m/e=304 (M+H$^+$).

EXAMPLE 206
2-(4-Imidazol-1-ylmethyl-imidazol-1-yl)-quinoline

Following the general method described in example 10, the title compound was obtained as an off-white crystalline material by reaction of (1-quinolin-2-yl-1H-imidazol-4-yl)-methanol first with thionylchloride and then with imidazole and sodium hydride followed by chromatography and crystallization of the free base. Mp.>150° C. dec. (AcOEt/hexane), MS: m/e=276 (M+H$^+$).

EXAMPLE 207
1H-Imidazole, 1-[[1-[3-chloro-4-(trifluoromethylthio)phenyl]-1H-imidazol-4-yl]methyl]-2-ethyl-, Hydrochloride (1:2)

Following the general method described in example 10, the title compound was obtained as a white crystalline material by reaction of [1-(3-chloro-4-trifluoromethylsulfanyl-phenyl)-1H-imidazol-4-yl]-methanol first with thionylchloride and then with 2-ethylimidazole and sodium hydride followed by chromatography and crystallization of the hydrochloride salt. Mp. 214–215° C. (MeOH/Et$_2$O), MS: m/e=387 (M+H$^+$).

EXAMPLE 208
1H-Imidazole, 1-[[1-[3-chloro-4-(trifluoromethylthio)phenyl]-1H-imidazol-4-yl]methyl]-2-methyl-, Hydrochloride (1:2)

Following the general method described in example 10, the title compound was obtained as a white crystalline material by reaction of [1-(3-chloro-4-trifluoromethylsulfanyl-phenyl)-1H-imidazol-4-yl]-methanol first with thionylchloride and then with 2-methylimidazole and sodium hydride followed by chromatography and crystallization of the hydrochloride salt. Mp. 195–198° C. (MeOH/Et$_2$O), MS: m/e=373 (M+H$^+$).

EXAMPLE 209
1-(3-Chloro-4-trifluoromethylsulfanyl-phenyl)-4-imidazol-1-ylmethyl-1H-imidazole Hydrochloride (1:2)

Following the general method described in example 10, the title compound was obtained as a white crystalline material by reaction of [1-(3-chloro-4-trifluoromethylsulfanyl-phenyl)-1H-imidazol-4-yl]-methanol first with thionylchloride and then with imidazole and sodium hydride followed by chromatography and crystallization of the hydrochloride salt. Mp. 244–245° C. (MeOH/Et$_2$O), MS: m/e=359 (M+H$^+$).

EXAMPLE 210
3-[4-(2-Ethyl-imidazol-1-ylmethyl)-imidazol-1-yl]-quinoline

Following the general method described in example 10, the title compound was obtained as an off-white crystalline material by reaction of (1-quinolin-3-yl-1H-imidazol-4-yl)-methanol first with thionylchloride and then with 2-ethylimidazole and sodium hydride followed by chromatography and crystallization of the free base. Mp. 132–136° C. (AcOEt/hexane), MS: m/e=304 (M+H$^+$).

EXAMPLE 211
3-[4-(2-Methyl-imidazol-1-ylmethyl)-imidazol-1-yl]-quinoline

Following the general method described in example 10, the title compound was obtained as an off-white crystalline material by reaction of (1-quinolin-3-yl-1H-imidazol-4-yl)-methanol first with thionylchloride and then with 2-methylimidazole and sodium hydride followed by chromatography and crystallization of the free base. Mp. 168–172° C. (AcOEt/hexane), MS: m/e=290 (M+H$^+$).

EXAMPLE 212
5-Chloro-2-[4-(2-methyl-imidazol-1-ylmethyl)-imidazol-1-yl]-pyridine Following the general method described in example 10, the title compound was obtained as an off-white crystalline material by reaction of [1-(5-chloro-pyridin-2-yl)-1H-imidazol-4-yl]-methanol first with thionylchloride and then with 2-methylimidazole and sodium hydride followed by chromatography and crystallization of the free base. Mp. 192–196° C. (AcOEt/hexane), MS: m/e=274 (M+H$^+$).

EXAMPLE 213
5-Chloro-2-[4-(2-ethyl-imidazol-1-ylmethyl)-imidazol-1-yl]-pyridine Following the general method described in example 10, the title compound was obtained as an off-white crystalline material by reaction of [1-(5-chloro-pyridin-2-yl)-1H-imidazol-4-yl]-methanol first with thionylchloride and then with 2-ethylimidazole and sodium hydride followed by chromatography and crystallization of the free base. Mp. 182–185° C. (AcOEt/hexane), MS: m/e=288 (M+H$^+$).

EXAMPLE 214
3-[4-(2-Methyl-imidazol-1-ylmethyl)-imidazol-1-yl]-isoquinoline Hydrochloride (1:2)

Following the general method described in example 10, the title compound was obtained as an off-white crystalline material by reaction of (1-isoquinolin-3-yl-1H-imidazol-4-yl)-methanol first with thionylchloride and then with 2-methylimidazole and sodium hydride followed by chromatography and crystallization of the hydrochloride salt. Mp.>250° C. (MeOH/Et$_2$O), MS: m/e=290 (M+H$^+$).

EXAMPLE 215
1H-Imidazole, 2-ethyl-1-[[1-[4-(trifluoromethoxy)phenyl]-1H-imidazol-4-yl]methyl]-, Hydrochloride (1:2)

Following the general method described in example 10, the title compound was obtained as a white crystalline material by reaction of [1-(4-trifluoromethoxy-phenyl)-1H-imidazol-4-yl]-methanol first with thionylchloride and then with 2-ethylimidazole and sodium hydride followed by chromatography and crystallization of the hydrochloride salt. Mp. 216–218° C. (MeOH/Et$_2$O), MS: m/e=337 (M+H$^+$).

EXAMPLE 216

1H-Imidazole, 2-methyl-1-[[1-[4-(trifluoromethoxy)phenyl]-1H-imidazol-4-yl]methyl]-, Hydrochloride (1:2)

Following the general method described in example 10, the title compound was obtained as a white crystalline material by reaction of [1-(4-trifluoromethoxy-phenyl)-1H-imidazol-4-yl]-methanol first with thionylchloride and then with 2-methylimidazole and sodium hydride followed by chromatography and crystallization of the hydrochloride salt. Mp. 231–233° C. (MeOH/Et$_2$O), MS: m/e=323 (M+H$^+$).

EXAMPLE 217

1H-Imidazole, 1-[[1-(1-biphenyl-3-yl)-1H-imidazol-4-yl]methyl]-2-methyl-, Hydrochloride (1:2)

A suspension of 1H-Imidazole, 1-[[1-(3-iodophenyl)-1H-imidazol-4-yl]methyl]-2-methyl-(0.20 g, 0.55 mmol) in toluene (10 ml) was treated (under an Ar-atmosphere) with tetrakis(triphenylphosphine)palladium (0.023 g, 0.02 mmol). After 30 min, phenylboronic acid (0.080 g, 0.66 mmol) and 2M aqueous K$_2$CO$_3$ solution (2.0 ml) was added. The reaction mixture was refluxed for 2 h and then extracted with AcOEt and H$_2$O. The organic phase was dried (Na$_2$SO$_4$), concentrated and chromatographed [silica, elution with gradient CH$_2$Cl$_2$ to 30% (CH$_2$Cl$_2$/MeOH/aq. NH$_4$OH=90:10:1)]. The free base of the title compound was obtained as a colorless oil (0.13 g, 75%). It was crystallized as the white hydrochloride salt. Mp. 241–243° C. (MeOH/Et$_2$O), MS: m/e=315 (M+H$^+$).

EXAMPLE 218

1H-Imidazole, 2-ethyl-1-[[1-[4-(trifluoromethylthio)phenyl]-1H-imidazol-4-yl]methyl]-, Hydrochloride (1:2)

Following the general method described in example 10, the title compound was obtained as a light yellow crystalline material by reaction of [i-(4-trifluoromethylsulfanyl-phenyl)-1H-imidazol-4-yl]-methanol first with thionylchloride and then with 2-ethylimidazole and sodium hydride followed by chromatography and crystallization of the hydrochloride salt. Mp. 183–185° C. (MeOH/Et$_2$O), MS: m/e=352(M$^+$).

EXAMPLE 219

1H-Imidazole, 2-methyl-1-[[1-[4-(trifluoromethylthio)phenyl]-1H-imidazol-4-yl]methyl]-, Hydrochloride (1:2)

Following the general method described in example 10, the title compound was obtained as a white crystalline material by reaction of [1-(4-trifluoromethylsulfanyl-phenyl)-1H-imidazol-4-yl]-methanol first with thionylchloride and then with 2-methylimidazole and sodium hydride followed by chromatography and crystallization of the hydrochloride salt. Mp. 249–250° C. (MeOH/Et$_2$O), MS: m/e=339(M+H$^+$).

EXAMPLE 220

6-[4-(2-Methyl-imidazol-1-ylmethyl)-imidazol-1-yl]-quinoline

Following the general method described in example 10, the title compound was obtained as an off-white crystalline material by reaction of (1-quinolin-6-yl-1H-imidazol-4-yl)-methanol first with thionylchloride and then with 2-methylimidazole and sodium hydride followed by chromatography and crystallization of the free base. Mp.>125° C. dec. (AcOEt/hexane), MS: m/e=290 (M+H$^+$).

EXAMPLE 221

6-[4-(2-Ethyl-imidazol-1-ylmethyl)-imidazol-1-yl]-quinoline

Following the general method described in example 10, the title compound was obtained as an off-white crystalline material by reaction of (1-quinolin-6-yl-1H-imidazol-4-yl)-methanol first with thionylchloride and then with 2-ethylimidazole and sodium hydride followed by chromatography and crystallization of the free base. Mp.>79° C. dec. (AcOEt/hexane), MS: m/e=304 (M+H$^+$).

EXAMPLE 222

8-[4-(2-Methyl-imidazol-1-ylmethyl)-imidazol-1-yl]-quinoline

Following the general method described in example 10, the title compound was obtained as an off-white crystalline material by reaction of (1-quinolin-8-yl-1H-imidazol-4-yl)-methanol first with thionylchloride and then with 2-methylimidazole and sodium hydride followed by chromatography and crystallization of the free base. Mp. 150–154° C. (AcOEt/hexane), MS: m/e=290 (M+H$^+$).

EXAMPLE 223

8-[4-(2-Ethyl-imidazol-1-ylmethyl)-imidazol-1-yl]-quinoline

Following the general method described in example 10, the title compound was obtained as an off-white crystalline material by reaction of (1-quinolin-8-yl-1H-imidazol-4-yl)-methanol first with thionylchloride and then with 2-ethylimidazole and sodium hydride followed by chromatography and crystallization of the free base. Mp. 78–81° C. (AcOEt/hexane), MS: m/e=304 (M+H$^+$).

EXAMPLE 224

1-(1-Benzo [1,3] dioxol-5-yl-1H-imidazol-4-ylmethyl)-1H-imidazol-2-ylamine Hydrochloride (1:2)

Following the general method described in example 104, 1H-imidazole, 1-[[1-(1,3-benzodioxol-5-yl)-1H-imidazol-4-yl]methyl]-2-nitro- was reacted with iron in acetic acid. After filtration, evaporation and chromatography, the free base of the title compound was isolated. It was converted into its light yellow hydrochloride salt. Mp.>245° C. dec. (MeOH/Et$_2$O), MS: m/e=284 (M+H$^+$).

EXAMPLE 225

3-(3-Difluoromethyl-4-fluoro-phenyl)-5-(2-methyl-imidazol-1-ylmethyl)-pyridine

The title compound was obtained according to example 129 (DMF instead of dioxane, 4 h, 100° C.) as a light brown solid (73% yield) by the reaction of 2-(3-difluoromethyl-4-fluoro-phenyl)-4,4,5,5-tetramethyl-[1,3,2]dioxaborolane with 3-bromo-5-(2-methyl-imidazol-1-ylmethyl)-pyridine. MS: m/e=318.3 (M+H$^+$).

EXAMPLE 226

3-[3-(1,1-Difluoro-ethyl)-phenyl]-5-(2-methyl-imidazol-1-ylmethyl)-pyridine

The title compound was obtained according to example 129 (DMF instead of dioxane, 4 h, 100° C.) as a light brown oil (70% yield) by the reaction of 2-[3-(1,1-difluoro-ethyl)-phenyl]-4,4,5,5-tetramethyl-[1,3,2]dioxaborolane with 3-bromo-5-(2-methyl-imidazol-1-ylmethyl)-pyridine. MS: m/e=314.3 (M+H$^+$).

EXAMPLE 227

3-(3-Fluoro-5-trifluoromethyl-phenyl)-5-(2-methyl-imidazol-1-ylmethyl)-pyridine

The title compound was obtained according to example 129 (DMF instead of dioxane, 4 h, 100° C.) as a light brown solid (67% yield) by the reaction of 2-(3-fluoro-5-trifluoromethyl-phenyl)-4,4,5,5-tetramethyl-[1,3,2] dioxaborolane with 3-bromo-5-(2-methyl-imidazol-1-ylmethyl)-pyridine. MS: m/e=336.3 (M+H$^+$).

EXAMPLE 228
3-[3-(1,1-Difluoro-ethyl)-4-fluoro-phenyl]-5-(2-methyl-imidazol-1-ylmethyl)-pyridine The title compound was obtained according to example 129 (DMF instead of dioxane, 4 hours, 100° C.) as a light brown oil (73% yield) by the reaction of 2-[3-(1,1-difluoro-ethyl)-4-fluoro-phenyl]-4,4,5,5-tetramethyl-[1,3,2] dioxaborolane with 3-bromo-5-(2-methyl-imidazol-1-ylmethyl)-pyridine. MS: m/e=332.3 (M+H$^+$).

EXAMPLE 229
1H-Imidazole, 2-cyclopropyl-1-[[1-(3,4-dichlorophenyl)-1H-imidazol-4-yl]methyl]-

Following the general method described in example 1, the title compound was obtained by reaction of 4-chloromethyl-1-(3,4-dichloro-phenyl)-1H-imidazole with 2-cyclopropyl-1H-imidazole and sodium hydride followed by chromatography to yield the title compound as a yellow oil. MS: m/e=334 (M+H$^+$).

EXAMPLE 230
5-(4-Fluoro-3-methyl-phenyl)-1-methyl-2-(2-methyl-imidazol-1-ylmethyl)-1-H-imidazole Hydrochloride (1:1)

5-Bromo-1-methyl-2-(2-methyl-imidazol-1-ylmethyl)-1H-imidazole (0.1 g, 0.392 mmol) was dissolved in toluene (4 ml) and MeOH (0.8 ml), treated with aqueous 2N Na$_2$CO$_3$ (0.2 ml), 4-fluoro-3-methylphenylboronic acid (0.078 g, 0.510 mmol) and tetrakis(triphenylphosphine)palladium (0.023 g, 0.020 mmol). The reaction mixture was refluxed under argon for 12 h, then cooled to room temperature and dried with Na$_2$SO$_4$. After filtration and evaporation of the solvent, the residue was chromatographed (silica, elution with CH$_2$Cl$_2$/MeOH=95:5). The product was dissolved in MeOH, cooled to 0° C. and treated with HCl/ether. Evaporation of the solvent and drying under high vacuum afforded the title compound (0.11 g, 88%) as a light yellow solid. MS: m/e=285.2 (M+H$^+$).

EXAMPLE 231
5-(4-Fluoro-3-trifluoromethyl-phenyl)-1-methyl-2-(2-methyl-imidazol-1-ylmethyl)-1-H-imidazole-hydrochloride (1:1)

5-Bromo-1-methyl-2-(2-methyl-imidazol-1-ylmethyl)-1H-imidazole (0.1 g, 0.392 mmol) was dissolved in DMF (1.5 ml), treated with K$_2$CO$_3$ (0.1 g, 0.784 mmol), 2-(4-fluoro-3-trifluoromethyl-phenyl)-4,4,5,5-tetramethyl-[1,3,2]-dioxaborolane (0.148 g, 0.510 mmol) and tetrakis(triphenylphosphine)palladium (0.047 g, 0.040 mmol). The reaction mixture was heated at 100° C. under argon for 12 h, then cooled to room temperature and dried with Na$_2$SO$_4$. After filtration and evaporation of the solvent, the residue was chromatographed (silica, elution with CH$_2$Cl$_2$/MeOH= 95:5). The product was dissolved in MeOH, cooled to 0° C. and treated with HCl/ether. Evaporation of the solvent and drying under high vacuum afforded the title compound (0.089 g, 88%) as a light brown solid. MS: m/e=339.2 (M+H$^+$).

EXAMPLE 232
5-(4-Chloro-3-methyl-phenyl)-1-methyl-2-(2-methyl-imidazol-1-ylmethyl)-1-H-imidazole-hydrochloride Hydrochloride (1:1)

Following the general method described in example 231, the title compound was obtained from 5-bromo-1-methyl-2-(2-methyl-imidazol-1-ylmethyl)-1H-imidazole and 2-(4-chloro-3-methyl-phenyl)-4,4,5,5-tetramethyl-[1,3,2]-dioxaborolane. MS: m/e=300.1 (M$^+$).

EXAMPLE 233
2-[5-(2-Methyl-imidazol-1-ylmethyl)-pyridin-3-yl]-1,2,3,4-tetrahydro-isoquinoline Hydrochloride (1:2)

This compound was prepared according to a procedure described in the following reference:
S. Wagaw; S. L. Buchwald; J. Org. Chem. 1996, 61, 7240–7241

3-Bromo-5-(2-methyl-imidazol-1-ylmethyl)-pyridine (0.1 g, 0.397 mmol) was dissolved in toluene (1 ml) and treated successively with 1,2,3,4-tetrahydroisoquinoline (61 μl, 0.476 mmol), sodium tert.-butoxide (53 mg, 0.556 mmol), Pd2(dba)3 chloroform complex (8.2 mg, 0.0079 mmol) and R(+)-BINAP (10 mg, 0.0159 mmol). The reaction mixture was heated at 70° C. under argon for 6 h, cooled to room temperature and quenched with water. The aqueous layer was extracted 3 times with ethyl acetate. The combined extracts were dried over Na$_2$SO$_4$, filtered and the solvent was removed in vacuo. The residue was chromatographed (silica, elution with CH$_2$Cl$_2$/MeOH=95:05) The product was dissolved in MeOH, cooled to 0° C. and treated with HCl/ether. Evaporation of the solvent and drying under high vacum afforded the title compound (0.09 g, 60%) as a yellow foam. MS: m/e=305.3 (M+H$^+$).

Processes for Preparation of Intermediates

EXAMPLE 234
1-(3,4-Dichloro-phenyl)-1H-imidazole-4-carboxylic Acid

A mixture of 3,4-dichloroaniline (24.3 g, 150 mmol), triethyl orthoformate (24.0 g, 162 mmol), ethyl nitroacetate (20.0 g, 150 mmol) and acetic acid (1 ml) was refluxed for 1 h. After addition of additional triethyl orthoformate (300 ml, 1.8 mol), iron powder (25.1 g, 450 mmol) and acetic acid (300 ml, 5.2 mol) the mixture was refluxed for 5 h. During this time, additional iron powder (25.1 g, 450 mmol) was added in 3 portions. The mixture was cooled to 60° C. and AcOEt (1 l) was added. After refluxing for 10 min, the precipitate was filtered and the filtrate was concentrated. Residual acetic acid was azeotropically removed by co-evaporation with toluene (500 ml). The crystalline residue was dissolved in dioxane (300 ml), 2N NaOH solution (300 ml) and charcoal (ca. 10 g) was added. The mixture was refluxed for 2 h, filtered and cooled to 5° C. HCl solution (37%) was added until precipitation was complete. Filtration and drying afforded the title compound (25.8 g, 67%) as light brown crystalline material. Mp.>235° C. dec. (H$_2$O), MS: m/e=255 [(M−H)$^-$]

Examples 235 to 262 were prepared according to the general procedure described in example 234.

EXAMPLE 235
1-(4-Chloro-3-methyl-phenyl)-1H-imidazole-4-carboxylic Acid

The title compound, MS: m/e=236 (M$^+$), Mp. 231–236° C. (H$_2$O/dioxane), was obtained as an off-white crystalline material by reaction of 4-chloro-3-methylaniline with triethyl orthoformate, ethyl nitroacetate and acetic acid followed by treatment with triethyl orthoformate, iron and acetic acid and subsequent alkaline hydrolysis.

EXAMPLE 236
1-Indan-5-yl-1H-imidazole-4-carboxylic Acid

The title compound, MS: m/e=227 [(M−H)$^-$], Mp. 243–251° C. (H$_2$O/dioxane), was obtained as an off-white crystalline material by reaction of 5-aminoindan with triethyl orthoformate, ethyl nitroacetate and acetic acid followed by treatment with triethyl orthoformate, iron and acetic acid and subsequent alkaline hydrolysis.

EXAMPLE 237
1-(3,4-Dimethyl-phenyl)-1H-imidazole-4-carboxylic Acid

The title compound, MS: m/e=216 (M$^+$), Mp.>250° C. (H$_2$O/dioxane), was obtained as an off-white crystalline material by reaction of 3,4-dimethylaniline with triethyl orthoformate, ethyl nitroacetate and acetic acid followed by treatment with triethyl orthoformate, iron and acetic acid and subsequent alkaline hydrolysis.

EXAMPLE 238
1-p-Tolyl-1H-imidazole-4-carboxylic Acid

The title compound, MS: m/e=202 (M$^+$), Mp.>250° C. (DMF), was obtained as a rose crystalline material by reaction of p-toluidine with triethyl orthoformate, ethyl nitroacetate and acetic acid followed by treatment with triethyl orthoformate, iron and acetic acid and subsequent alkaline hydrolysis.

EXAMPLE 239
1-(4-Fluoro-3-methyl-phenyl)-1H-imidazole-4-carboxylic Acid

The title compound, MS: m/e=219 [(M−H)$^-$], Mp. 192–198° C. (H$_2$O/dioxane), was obtained as an off-white crystalline material by reaction of 4-fluoro-3-methylaniline with triethyl orthoformate, ethyl nitroacetate and acetic acid followed by treatment with triethyl orthoformate, iron and acetic acid and subsequent alkaline hydrolysis.

EXAMPLE 240
1-(4-Methylsulfanyl-phenyl)-1H-imidazole-4-carboxylic Acid

The title compound, MS: m/e=233 [(M−H)$^-$], Mp. 233–245° C. (H$_2$O/dioxane), was obtained as a red crystalline material by reaction of 4-(methylthio)aniline with triethyl orthoformate, ethyl nitroacetate and acetic acid followed by treatment with triethyl orthoformate, iron and acetic acid and subsequent alkaline hydrolysis.

EXAMPLE 241
1-(3-Trifluoromethyl-phenyl)-1H-imidazole-4-carboxylic Acid

The title compound, MS: m/e=256 M$^+$, Mp. 233–245° C. (H$_2$O/DMF), was obtained as a light orange crystalline material by reaction of 3-(trifluoromethyl)aniline with triethyl orthoformate, ethyl nitroacetate and acetic acid followed by treatment with triethyl orthoformate, iron and acetic acid and subsequent alkaline hydrolysis.

EXAMPLE 242
1-(4-Fluoro-3-trifluoromethyl-phenyl)-1H-imidazole-4-carboxylic Acid The title compound, MS: m/e=274 M$^+$, Mp. 188–193° C. (H$_2$O/dioxane), was obtained as an off-white crystalline material by reaction of 4-fluoro-3(trifluoromethyl)aniline with triethyl orthoformate, ethyl nitroacetate and acetic acid followed by treatment with triethyl orthoformate, iron and acetic acid and subsequent alkaline hydrolysis.

EXAMPLE 243
1-(3-Fluoro-4-trifluoromethyl-phenyl)-1H-imidazole-4-carboxylic Acid The title compound, MS: m/e=274 M$^+$, Mp.>250° C. (H$_2$O/dioxane), was obtained as an off-white crystalline material by reaction of 3-fluoro-4(trifluoromethyl)aniline with triethyl orthoformate, ethyl nitroacetate and acetic acid followed by treatment with triethyl orthoformate, iron and acetic acid and subsequent alkaline hydrolysis.

EXAMPLE 244
1-(4-Methyl-3-trifluoromethyl-phenyl)-1H-imidazole-4-carboxylic Acid The title compound, MS: m/e=269 [(M−H) $^-$] Mp.>233° C. dec. (H$_2$O/dioxane), was obtained as an off-white crystalline material by reaction of 4-methyl-3(trifluoromethyl)aniline with triethyl orthoformate, ethyl nitroacetate and acetic acid followed by treatment with triethyl orthoformate, iron and acetic acid and subsequent alkaline hydrolysis.

EXAMPLE 245
1-(4-Chloro-3-methoxy-phenyl)-1H-imidazole-4-carboxylic Acid

The title compound, MS: m/e=252 (M$^+$), Mp. 232–236° C. (H$_2$O/dioxane), was obtained as a light red crystalline material by reaction of 4-chloro-3-methoxy aniline with triethyl orthoformate, ethyl nitroacetate and acetic acid followed by treatment with triethyl orthoformate, iron and acetic acid and subsequent alkaline hydrolysis.

EXAMPLE 246
1-(4-Fluoro-3-methoxy-phenyl)-1H-imidazole-4-carboxylic Acid

The title compound, MS: m/e=236 (M$^+$), Mp.>182° C. dec. (H$_2$O/dioxane), was obtained as a light brown crystalline material by reaction of 4-fluoro-3-methoxy aniline with triethyl orthoformate, ethyl nitroacetate and acetic acid followed by treatment with triethyl orthoformate, iron and acetic acid and subsequent alkaline hydrolysis.

EXAMPLE 247
1-(4-Chloro-phenyl)-1H-imidazole-4-carboxylic Acid

The title compound, MS: m/e=222 (M$^+$), Mp.>250° C. (DMF/H$_2$O) was obtained as a rose crystalline material by reaction of 4-chloroaniline with triethyl orthoformate, ethyl nitroacetate and acetic acid followed by treatment with triethyl orthoformate, iron and acetic acid and subsequent alkaline hydrolysis.

EXAMPLE 248
1-Benzo 1,3 dioxol-5-yl-1H-imidazole-4-carboxylic Acid

The title compound, MS: m/e=232 (M$^+$), Mp.>250° C. (H$_2$O/dioxane) was obtained as a grey crystalline material by reaction of 3,4-methylenedioxyaniline with triethyl orthoformate, ethyl nitroacetate and acetic acid followed by treatment with triethyl orthoformate, iron and acetic acid and subsequent alkaline hydrolysis.

EXAMPLE 249
1-(3-Fluoro-4-methyl-phenyl)-1H-imidazole-4-carboxylic Acid

The title compound, MS: m/e=220 (M$^+$), Mp.>250° C. (H$_2$O/dioxane) was obtained as an off-white crystalline material by reaction of 3-fluoro-4-methylaniline with triethyl orthoformate, ethyl nitroacetate and acetic acid followed by treatment with triethyl orthoformate, iron and acetic acid and subsequent alkaline hydrolysis.

EXAMPLE 250
1-(3-Chloro-4-methoxy-phenyl)-1H-imidazole-4-carboxylic Acid

The title compound, MS: m/e=252 (M$^+$), Mp. 224–226° C. (H$_2$O/dioxane) was obtained as a white crystalline material by reaction of 3-chloro-4-methoxyaniline with triethyl orthoformate, ethyl nitroacetate and acetic acid followed by treatment with triethyl orthoformate, iron and acetic acid and subsequent alkaline hydrolysis.

EXAMPLE 251

1-(4-Chloro-2-fluoro-phenyl)-1H-imidazole-4-carboxylic Acid

The title compound, MS: m/e=239 [(M−H)⁻], Mp. 234–238° C. (H$_2$O/dioxane) was obtained as a light yellow crystalline material by reaction of 4-chloro-2-fluoroaniline with triethyl orthoformate, ethyl nitroacetate and acetic acid followed by treatment with triethyl orthoformate, iron and acetic acid and subsequent alkaline hydrolysis.

EXAMPLE 252

1-(4-Bromo-phenyl)-1H-imidazole-4-carboxylic Acid

The title compound, MS: m/e=266 (M⁺), Mp.>250° C. (H$_2$O/dioxane) was obtained as a light yellow crystalline material by reaction of 4-bromoaniline with triethyl orthoformate, ethyl nitroacetate and acetic acid followed by treatment with triethyl orthoformate, iron and acetic acid and subsequent alkaline hydrolysis.

EXAMPLE 253

1-(4-Difluoromethoxy-phenyl)-1H-imidazole-4-carboxylic Acid

The title compound, MS: m/e=253 [(M−H) 1, Mp. 218–225° C. (H$_2$O/dioxane) was obtained as a white crystalline material by reaction of 4-difluoromethoxyaniline with triethyl orthoformate, ethyl nitroacetate and acetic acid followed by treatment with triethyl orthoformate, iron and acetic acid and subsequent alkaline hydrolysis.

EXAMPLE 254

1-(4-Benzyloxy-phenyl)-1H-imidazole-4-carboxylic Acid

The title compound, MS: m/e=293 [(M−H)⁻], Mp. 238–243° C. dec. (H$_2$O/dioxane) was obtained as an off-white crystalline material by reaction of 4-benzyloxyaniline with triethyl orthoformate, ethyl nitroacetate and acetic acid followed by treatment with triethyl orthoformate, iron and acetic acid and subsequent alkaline hydrolysis.

EXAMPLE 255

1-(3-Methoxy-4-methyl-phenyl)-1H-imidazole-4-carboxylic Acid

The title compound, MS: m/e=232 (M⁺), Mp. 226–230° C. (H$_2$O/dioxane) was obtained as a rose crystalline material by reaction of 3-methoxy-4-methylaniline with triethyl orthoformate, ethyl nitroacetate and acetic acid followed by treatment with triethyl orthoformate, iron and acetic acid and subsequent alkaline hydrolysis.

EXAMPLE 256

1-(4-Trifluoromethyl-phenyl)-1H-imidazole-4-carboxylic Acid

The title compound, MS: m/e=256 (M⁺), Mp.>250° C. (H$_2$O/dioxane) was obtained as a light yellow crystalline material by reaction of 4-(trifluoromethyl)aniline with triethyl orthoformate, ethyl nitroacetate and acetic acid followed by treatment with triethyl orthoformate, iron and acetic acid and subsequent alkaline hydrolysis.

EXAMPLE 257

1-(1,3-Dihydro-isobenzofuran-5-yl)-1H-imidazole-4-carboxylic Acid

The title compound, MS: m/e=230 (M⁺), Mp. 245–247° C. (DMF/H$_2$O) was obtained as a light brown crystalline material by reaction of 1,3-dihydro-5-isobenzofuranamine (prepared according to T. Y. Shen et al., *J. Med. Chem.,* 1978, 21, 965) with triethyl orthoformate, ethyl nitroacetate and acetic acid followed by treatment with triethyl orthoformate, iron and acetic acid and subsequent alkaline hydrolysis.

EXAMPLE 258

1-(4-Fluoro-3-methoxy-phenyl)-1H-imidazole-4-carboxylic Acid

The title compound, MS: m/e=236 (M⁺), Mp.>182° C. dec. (H$_2$O/dioxane) was obtained as a light brown crystalline material by reaction of 4-fluoro-3-methoxyaniline with triethyl orthoformate, ethyl nitroacetate and acetic acid followed by treatment with triethyl orthoformate, iron and acetic acid and subsequent alkaline hydrolysis.

EXAMPLE 259

1-Phenyl-1H-imidazole-4-carboxylic Acid

The title compound, MS: m/e=188 (M⁺), Mp. 220–221° C. (DMF/H$_2$O) was obtained as a white crystalline material by reaction of aniline with triethyl orthoformate, ethyl nitroacetate and acetic acid followed by treatment with triethyl orthoformate, iron and acetic acid and subsequent alkaline hydrolysis.

EXAMPLE 260

1-(4-Methoxy-phenyl)-1H-imidazole-4-carboxylic Acid

The title compound, MS: m/e=218 (M⁺), Mp.>240° C. dec.(H$_2$O/dioxane) was obtained as a light brown crystalline material by reaction of p-anisidine with triethyl orthoformate, ethyl nitroacetate and acetic acid followed by treatment with triethyl orthoformate, iron and acetic acid and subsequent alkaline hydrolysis.

EXAMPLE 261

1-(3-Methoxy-phenyl)-1H-imidazole-4-carboxylic Acid

The title compound, MS: m/e=218 (M⁺), Mp. 196–201° C. (H$_2$O/dioxane) was obtained as a light red crystalline material by reaction of m-anisidine with triethyl orthoformate, ethyl nitroacetate and acetic acid followed by treatment with triethyl orthoformate, iron and acetic acid and subsequent alkaline hydrolysis.

EXAMPLE 262

1-(4-Methoxy-3-trifluoromethyl-phenyl)-1H-imidazole-4-carboxylic Acid

The title compound, MS: m/e=286 (M⁺), Mp.>141° C. dec. (H$_2$O/dioxane) was obtained as a light brown crystalline material by reaction of 4-methoxy-3-(trifluoromethyl) aniline with triethyl orthoformate, ethyl nitroacetate and acetic acid followed by treatment with triethyl orthoformate, iron and acetic acid and subsequent alkaline hydrolysis.

EXAMPLE 263

1-(3,4-Dichloro-phenyl)-5-methyl-1H-imidazole-4-carboxylic Acid Ethyl Ester and 3-(3,4-Dichloro-phenyl)-5-methyl-3H-imidazole-4-carboxylic Acid Ethyl Ester A suspension of 3,4-dichlorophenylboronic acid (8.22 g, 43.1 mmol), ethyl 4-methyl-5-imidazolecarboxylate (6.64 g, 43.1 mmol) and copper(II) acetate (7.83 g, 43.1 mmol) in CH$_2$Cl$_2$ (86 ml) was stirred at 20° C. for 48 h. All solids were filtered, the organic phase diluted with AcOEt (500 ml) and stirred with saturated aqueous Seignette salt solution. After filtration and evaporation the residue was chromatographed (silica, eluation with gradient hexane to AcOEt) to obtain 2.8 g (22%) of 3-(3,4-dichloro-phenyl)-5-methyl-3H-imidazole-4-carboxylic acid ethyl ester [Mp. 135–136° C.

(AcOEt/hexane), MS: m/e=298 (M⁺)] and 1.0 g (8%) of 1-(3,4-dichloro-phenyl)-5-methyl-1H-imidazole-4-carboxylic acid ethyl ester [Mp. 163–164° C. (AcOEt/hexane), MS: m/e=298 (M⁺)].

EXAMPLE 264

[1-(3,4-Dichloro-phenyl)-1H-imidazol-4-yl]-methanol 1-(3,4-Dichloro-phenyl)-1H-imidazole-4-carboxylic acid (20.0 g, 77.8 mmol) was treated with 1M BH$_3$ THF complex (100 ml) and refluxed for 2 h. The mixture was cooled to 5° C. and MeOH (20 ml) was added slowly. After evaporation of all volatiles the residue was taken up in 2N HCl solution (100 ml) and refluxed for 2 h. After filtration the hot aqueous phase was slowly treated with 2N NaOH solution until pH 10. On cooling the title compound crystallizes as a white material (12.2 g, 65%). Mp. 146–147° C. (H$_2$O), MS: m/e=242 (M⁺).

Examples 265 to 292 were prepared according to the general procedure described in example 264.

EXAMPLE 265

[1-(4-Chloro-3-methyl-phenyl)-1H-imidazol-4-yl]-methanol

The title compound, MS: m/e=222 (M⁺), Mp. 126–133° C. (H$_2$O) was obtained as a light brown crystalline material by reaction of 1-(4-chloro-3-methyl-phenyl)-1H-imidazole-4-carboxylic acid with BH$_3$ THF complex followed by hydrolytic workup.

EXAMPLE 266

(1-Indan-5-yl-1H-imidazol-4-yl)-methanol

The title compound, MS: m/e=214 (M⁺), Mp. 128–133° C. (H$_2$O) was obtained as a light brown crystalline material by reaction of 1-indan-5-yl-1H-imidazole-4-carboxylic acid with BH$_3$ THF complex followed by hydrolytic workup.

EXAMPLE 267

[1-(3,4-Dimethyl-phenyl)-1H-imidazol-4-yl]-methanol

The title compound, MS: m/e=202 (M⁺), Mp. 110–116° C. (H$_2$O) was obtained as an off-white crystalline material by reaction of 1-(3,4-dimethyl-phenyl)-1H-imidazole-4-carboxylic acid with BH$_3$ THF complex followed by hydrolytic workup.

EXAMPLE 268

(1-p-Tolyl-1H-imidazol-4-yl)-methanol

The title compound, MS: m/e=188 (M⁺), Mp. 101–102° C. (H$_2$O) was obtained as an off-white crystalline material by reaction of 1-p-tolyl-1H-imidazole-4-carboxylic acid with BH$_3$ THF complex followed by hydrolytic workup.

EXAMPLE 269

1-(4-Fluoro-3-methyl-phenyl)-1H-imidazol-4-yl]-methanol

The title compound, MS: m/e=206 (M⁺), Mp. 138–144° C. (H$_2$O) was obtained as an off-white crystalline material by reaction of 1-(4-fluoro-3-methyl-phenyl)-1H-imidazole-4-carboxylic acid with BH$_3$ THF complex followed by hydrolytic workup.

EXAMPLE 270

[1-(4-Methylsulfanyl-phenyl)-1H-imidazol-4-yl]-methanol

The title compound, MS: m/e=220 (M⁺), Mp. 108–114° C. (H$_2$O) was obtained as a light brown crystalline material by reaction of 1-(4-methylsulfanyl-phenyl)-1H-imidazole-4-carboxylic acid with BH$_3$ THF complex followed by hydrolytic workup.

EXAMPLE 271

[1-(3-Trifluoromethyl-phenyl)-1H-imidazol-4-yl]-methanol

The title compound, MS: m/e=242 (M⁺), Mp. 96–100° C. (H$_2$O) was obtained as a white crystalline material by reaction of 1-(3-trifluoromethyl-phenyl)-1H-imidazole-4-carboxylic acid with BH$_3$ THF complex followed by hydrolytic workup.

EXAMPLE 272

[1-(4-Fluoro-3-trifluoromethyl-phenyl)-1H-imidazol-4-yl]-methanol

The title compound, MS: m/e=260 (M+'), Mp. 142–146° C. (H$_2$O) was obtained as a white crystalline material by reaction of 1-(4-fluoro-3-trifluoromethyl-phenyl) 1H-imidazole-4-carboxylic acid with BH$_3$ THF complex followed by hydrolytic workup.

EXAMPLE 273

[1-(3-Fluoro-4-trifluoromethyl-phenyl)-1H-imidazol-4-yl]-methanol

The title compound, MS: m/e=260 (M⁺), Mp. 142–144° C. (H$_2$O) was obtained as a white crystalline material by reaction of 1-(3-fluoro-4-trifluoromethyl-phenyl)-1H-imidazole-4-carboxylic acid with BH$_3$ THF complex followed by hydrolytic workup.

EXAMPLE 274

[1-(4-Methyl-3-trifluoromethyl-phenyl)-1H-imidazol-4-yl]-methanol

The title compound, MS: m/e=257 (M+H⁺), Mp. 116–119° C. (H$_2$O) was obtained as a white crystalline material by reaction of 1-(4-methyl-3-trifluoromethyl-phenyl)-1H-imidazole-4-carboxylic acid with BH$_3$ THF complex followed by hydrolytic workup.

EXAMPLE 275

[1-(4-Chloro-3-methoxy-phenyl)-1H-imidazol-4-yl]-methanol

The title compound, MS: m/e=238 (M⁺), Mp. 116–119° C. (H$_2$O) was obtained as a white crystalline material by reaction of 1-(4-chloro-3-methoxy-phenyl)-1H-imidazole-4-carboxylic acid with BH$_3$ THF complex followed by hydrolytic workup.

EXAMPLE 276

[1-(4-Fluoro-3-methoxy-phenyl)-1H-imidazol-4-yl]-methanol

The title compound, MS: m/e=222 (M⁺), Mp. 174–177° C. (H$_2$O) was obtained as an off-white crystalline material by reaction of 1-(4-fluoro-3-methoxy-phenyl)-1H-imidazole-4-carboxylic acid with BH$_3$ THF complex followed by hydrolytic workup.

EXAMPLE 277

[1-(4-Chloro-phenyl)-1H-imidazol-4-yl]-methanol

The title compound, MS: m/e=208 (M⁺), Mp. 115–116° C. (AcOEt) was obtained as a white crystalline material by reaction of 1-(4-chloro-phenyl)-1H-imidazole-4-carboxylic acid with BH$_3$ THF complex followed by hydrolytic workup.

EXAMPLE 278

(1-Benzo[1,3]dioxol-5-yl-1H-imidazol-4-yl)-methanol

The title compound, MS: m/e=218 (M⁺), Mp. 150–157° C. (H$_2$O) was obtained as a white crystalline material by reaction of 1-benzo[1,3] dioxol-5-yl-1H-imidazole-4-carboxylic acid with BH$_3$ THF complex followed by hydrolytic workup.

EXAMPLE 279
[1-(3-Fluoro-4-methyl-phenyl)-1H-imidazol-4-yl]-methanol

The title compound, MS: m/e=206 (M$^+$), Mp. 115–122° C. (H$_2$O) was obtained as a light yellow crystalline material by reaction of 1-(3-fluoro-4-methyl-phenyl)-1H-imidazole-4-carboxylic acid with BH$_3$ THF complex followed by hydrolytic workup.

EXAMPLE 280
[1-(3-Chloro-4-methoxy-phenyl)-1H-imidazol-4-yl]-methanol

The title compound, MS: m/e=238 (M$^+$), Mp. 133–138° C. (H$_2$O) was obtained as an off-white crystalline material by reaction of 1-(3-chloro-4-methoxy-phenyl)-1H-imidazole-4-carboxylic acid with BH$_3$ THF complex followed by hydrolytic workup.

EXAMPLE 281
[1-(4-Chloro-2-fluoro-phenyl)-1H-imidazol-4-yl]-methanol

The title compound, MS: m/e=226 (M$^+$), Mp. 120–130° C. (H$_2$O) was obtained as an off-white crystalline material by reaction of 1-(4-chloro-2-fluoro-phenyl)-1H-imidazole-4-carboxylic acid with BH$_3$ THF complex followed by hydrolytic workup.

EXAMPLE 282
[1-(4-Bromo-phenyl)-1H-imidazol-4-yl]-methanol

The title compound, MS: m/e=252 (M$^+$), Mp. 132–139° C. (H$_2$O) was obtained as a light yellow crystalline material by reaction of 1-(4-bromo-phenyl)-1H-imidazole-4-carboxylic acid with BH$_3$ THF complex followed by hydrolytic workup.

EXAMPLE 283
[[1-(4-Difluoromethoxy-phenyl)-1H-imidazol-4-yl]-methanol

The title compound, MS: m/e=240 (M$^+$), Mp. 66–72° C. (H$_2$O) was obtained as a light brown crystalline material by reaction of 1-(4-difluoromethoxy-phenyl)-1H-imidazole-4-carboxylic acid with BH$_3$ THF complex followed by hydrolytic workup.

EXAMPLE 284
[1-(4-Benzyloxy-phenyl)-1H-imidazol-4-yl]-methanol

The title compound, MS: m/e=280 (M$^+$), Mp. 151–152° C. (AcOEt) was obtained as a white crystalline material by reaction of 1-(4-benzyloxy-phenyl)-1H-imidazole-4-carboxylic acid with BH$_3$ THF complex followed by hydrolytic workup.

EXAMPLE 285
[1-(3-Methoxy-4-methyl-phenyl)-1H-imidazol-4-yl]-methanol

The title compound, MS: m/e=218 (M$^+$), Mp. 141–147° C. (H$_2$O) was obtained as a white crystalline material by reaction of 1-(3-methoxy-4-methyl-phenyl)-1H-imidazole-4-carboxylic acid with BH$_3$ THF complex followed by hydrolytic workup.

EXAMPLE 286
[1-(4-Trifluoromethyl-phenyl)-1H-imidazol-4-yl]-methanol

The title compound, MS: m/e=242 (M$^+$), Mp. 153–156° C. (H$_2$O) was obtained as an off-white crystalline material by reaction of 1-(4-trifluoromethyl-phenyl)-1H-imidazole-4-carboxylic acid with BH$_3$ THF complex followed by hydrolytic workup.

EXAMPLE 287
[1-(1,3-Dihydro-isobenzofuran-5-yl)-1H-imidazol-4-yl]-methanol

The title compound, MS: m/e=216 (M$^+$), Mp. 161–165° C. (AcOEt) was obtained as an off-white crystalline material by reaction of 1-(1,3-dihydro-isobenzofuran-5-yl)-1H-imidazole-4-carboxylic acid with BH$_3$ THF complex followed by hydrolytic workup.

EXAMPLE 288
[1-(3-Fluoro-4-methoxy-phenyl)-1H-imidazol-4-yl]-methanol

The title compound, MS: m/e=222 (M$^+$), Mp. 112–120° C. (CH$_2$Cl$_2$/iPr$_2$O) was obtained as a white crystalline material by reaction of 1-(4-fluoro-3-methoxy-phenyl)-1H-imidazole-4-carboxylic acid with BH$_3$ THF complex followed by hydrolytic workup.

EXAMPLE 289
[(1-Phenyl-1H-imidazol-4-yl)-methanol

The title compound, MS: m/e=174(M$^+$), Mp. 116–118° C. (H$_2$O) was obtained as a white crystalline material by reaction of 1-phenyl-1H-imidazole-4-carboxylic acid with BH$_3$ THF complex followed by hydrolytic workup.

EXAMPLE 290
[1 (4-Methoxy-phenyl)-1H-imidazol-4-yl]-methanol

The title compound, MS: m/e=204(M$^+$), Mp. 107–109° C. (AcOEt) was obtained as a white crystalline material by reaction of 1-(4-methoxy-phenyl)-1H-imidazole-4-carboxylic acid with BH$_3$ THF complex followed by hydrolytic workup.

EXAMPLE 291
[1-(3-Methoxy-phenyl)-1H-imidazol-4-yl]-methanol

The title compound, MS: m/e=204(M$^+$), Mp. 80–85° C. (AcOEt/hexane) was obtained as a white crystalline material by reaction of 1-(3-methoxy-phenyl)-1H-imidazole-4-carboxylic acid with BH$_3$ THF complex followed by hydrolytic workup.

EXAMPLE 292
[1-(4-Methoxy-3-trifluoromethyl-phenyl)-1H-imidazol-4-yl]-methanol The title compound, MS: m/e=272 (M$^+$), Mp. 147–150° C. (H$_2$O) was obtained as an off-white crystalline material by reaction of 1-(4-methoxy-3-trifluoromethyl-phenyl)-1H-imidazole-4-carboxylic acid with BH$_3$ THF complex followed by hydrolytic workup.

EXAMPLE 293
[1-(3-Chloro-4-methyl-phenyl)-1H-imidazol-4-yl]-methanol

According to example 234, 3-chloro-4-methylaniline (21.5 g, 150 mmol) was reacted with triethyl orthoformate, ethyl nitroacetate and acetic acid followed by treatment with triethyl orthoformate, iron and acetic acid and subsequent alkaline hydrolysis. The isolated acid (10.0 g) was directly reduced according to example 264, by reaction with BH$_3$ THF complex followed by hydrolytic workup and the title compound was obtained as a white crystalline solid (5.2 g, 16%). Mp. 126–133° C. (AcOEt/hexane), MS: m/e=222 (M$^+$)

Examples 294 to 297 were prepared according to the general procedure described in example 293.

EXAMPLE 294
[1-(4-Chloro-3-trifluoromethyl-phenyl)-1H-imidazol-4-yl]-methanol 3-Trifluoromethyl-4-chloroaniline was reacted with triethyl orthoformate, ethyl nitroacetate and acetic acid followed by treatment with triethyl orthoformate, iron and acetic acid and subsequent alkaline hydrolysis. The isolated acid was directly reduced with $BH_3$ THF complex followed by hydrolytic workup and the title compound, Mp. 148–153° C. (AcOEt/iPr$_2$O), MS: m/e=276 (M$^+$), was obtained as a white crystalline solid.

EXAMPLE 295
[1-(3-Chloro-4-fluoro-phenyl)-1H-imidazol-4-yl]-methanol

3-Chloro-4-fluoroaniline was reacted with triethyl orthoformate, ethyl nitroacetate and acetic acid followed by treatment with triethyl orthoformate, iron and acetic acid and subsequent alkaline hydrolysis. The isolated acid was directly reduced with $BH_3$ THF complex followed by hydrolytic workup and the title compound, Mp. 130–135° C. (H$_2$O), MS: m/e=226 (M$^+$), was obtained as an off-white crystalline solid.

EXAMPLE 296
(1-Biphenyl-4-yl-1H-imidazol-4-yl)-methanol

4-Phenylaniline was reacted with triethyl orthoformate, ethyl nitroacetate and acetic acid followed by treatment with triethyl orthoformate, iron and acetic acid and subsequent alkaline hydrolysis. The isolated acid was directly reduced with $BH_3$ THF complex followed by hydrolytic workup and the title compound, Mp. 173–177° C. (CH$_2$Cl$_2$/iPr$_2$O), MS: m/e=250 (M$^+$), was obtained as a yellow crystalline solid.

EXAMPLE 297
[1-(4-Isopropyl-3-methyl-phenyl)-1H-imidazol-4-yl]-methanol

4-Isopropyl-3-methylaniline was reacted with triethyl orthoformate, ethyl nitroacetate and acetic acid followed by treatment with triethyl orthoformate, iron and acetic acid and subsequent alkaline hydrolysis. The isolated acid was directly reduced with $BH_3$ THF complex followed by hydrolytic workup and the title compound, Mp. 98–102° C. (CH$_2$Cl$_2$/iPr$_2$O), MS: m/e=230 (M$^+$), was obtained as a yellow crystalline solid.

EXAMPLE 298
[1-(3,4-Dichloro-phenyl)-5-methyl-1H-imidazol-4-yl]-methanol

To a solution of 1-(3,4-dichloro-phenyl)-5-methyl-1H-imidazole-4-carboxylic acid ethyl ester (0.82 g, 2.7 mmol) in THF (27 ml) lithium aluminum hydride (0.21 g, 5.4 mmol) was added portionwise keeping T<10° C. The mixture was stirred in an ice-bath for 2 h, then 1 ml saturated aqueous Seignette salt solution was slowly added. After dilution with AcOEt (100 ml) the mixture was filtered, concentrated and chromatographed [silica, elution with gradient CH$_2$Cl$_2$ to 80% (CH$_2$Cl$_2$/MeOH=9:1)]. The title compound was obtained as a white crystalline solid (0.46 g, 66%). Mp. 174–175° C. (CH$_2$Cl$_2$/iPr$_2$O), MS: m/e=256 (M$^+$)

EXAMPLE 299
4-Chloromethyl-1-(3,4-dichloro-phenyl)-1H-imidazole

In an ice-bath thionyl chloride (39.5 ml, excess) was slowly added to [1-(3,4-dichloro-phenyl)-1H-imidazol-4-yl]-methanol (9.6 g, 39.5 mmol). The resulting mixture was stirred for 24 h. After evaporation, the oily residue was triturated with ether and 10.12 g (86%) of the hydrochloride salt of the title compound was obtained as an off-white solid. To obtain the free base, the salt was carefully neutralized with aqueous NaOH (2N) and extracted with AcOEt. The organic phase was dried (Na$_2$SO$_4$) and concentrated to obtain 8.43 g (95%) of the title compound as an off-white solid. Mp. 146–147° C. dec. (AcOEt/hexane), MS: m/e=260 (M$^+$)

EXAMPLE 300
1H-Imidazole, 1-[[1-(3,4-dichlorophenyl)-1H-imidazol-4-yl]methyl]-2-nitro- 4-Chloromethyl-1-(3,4-dichloro-phenyl)-1H-imidazole (2.0 g, 7.5 mmol) was dissolved in DMF (25 ml), 2-nitroimidazole (1.0 g, 8.8 mmol) and cesium carbonate (1.43 g, 4.4 mmol) was added and the resulting mixture was stirred at 70° C. for 3 h. After evaporation of the solvent, the residue was dissolved in AcOEt and washed with H$_2$O. The organic phase was dried (Na$_2$SO$_4$), concentrated and chromatographed [silica, elution with gradient CH$_2$Cl$_2$ to 50% (CH$_2$Cl$_2$/MeOH=9:1)] to obtain 2.48 g (98%) of the title compound as an off-white solid. Mp. 130–131° C. (CH$_2$Cl$_2$/iPr$_2$O), MS: m/e=291 [(M—NO$_2$)$^+$].

EXAMPLE 301
1H-Imidazole, 1-[[1-(4-chloro-3-methylphenyl)-1H-imidazol-4-yl]methyl]-2-nitro- According to example 299 [1-(4-chloro-3-methylphenyl)-1H-imidazol-4-yl]-methanol was reacted with thionylchloride and the obtained 4-chloromethyl-1-(4-chloro-3-methyl-phenyl)-1H-imidazole directly reacted further as its hydrochloric salt. Thus, as described for example 300, reaction of 4-chloromethyl-1-(4-chloro-3-methyl-phenyl)-1H-imidazole HCl salt with 2-nitroimidazole (1.2 eq.) and cesium carbonate (1.2 eq.) led, after evaporation and extractive workup, to the crude product, which was purified by chromatography. Mp. 147–148° C. (CH$_2$Cl$_2$/hexane), MS: m/e=271 [(M—NO$_2$)$^+$].

Examples 302 and 303 were prepared according to the general procedure described in example 301.

EXAMPLE 302
1H-Imidazole, 1-[[1-(4-methylphenyl)-1H-imidazol-4-yl]methyl]-2-nitro- (1-p-Tolyl-1H-imidazol-4-yl)-methanol was treated first with thionylchloride, then with 2-nitroimidazole and cesium carbonate. After evaporation, extractive workup and chromatography the title compound was obtained as a white solid. Mp. 147–148° C. (CH$_2$Cl$_2$/iPr$_2$O), MS: m/e=237 [(M—NO$_2$)$^+$].

EXAMPLE 303
1H-Imidazole, 2-nitro-1-[(1-phenyl-1H-imidazol-4-yl)methyl]-

[(1-Phenyl-1H-imidazol-4-yl)-methanol was treated first with thionylchloride, then with 2-nitroimidazole and cesium carbonate. After evaporation, extractive workup and chromatography the title compound was obtained as a white solid. Mp. 126–127° C. (CH$_2$Cl$_2$/iPr$_2$O), MS: m/e=223 [(M—NO$_2$)$^+$].

EXAMPLE 304
1-(3,4-Dichloro-phenyl)-1H-imidazole-4-carboxylic Acid Amide

Carbonyldiimidazole (0.49 g, 3 mmol) was added to a stirred suspension of 1-(3,4-dichloro-phenyl)-1H-imidazole-4-carboxylic acid (0.64 g, 2.5 mmol) in DMF (10 ml). After 1 h at 60° C., the reaction mixture was cooled to rt, aqueous ammonia (25%, 20 ml) was added and stirring was continued for 12 h. Then H₂O (100 ml) was added and the precipitated product was filtered. Recrystallisation from EtOH afforded the title compound as off-white crystals. Mp. 244–245° C. (EtOH), MS: m/e=255 (M⁺).

EXAMPLE 305
1-(3,4-Dichlorophenyl)-1H-imidazole-4-methanamine Fumarate (1:1)

1-(3,4-Dichloro-phenyl)-1H-imidazole-4-carboxylic acid amide (4.32 g, 16.9 mmol) was treated with 1M BH₃ THF complex (100 ml) and refluxed for 6 h. The mixture was cooled to 5° C. and MeOH (50 ml) was added slowly. After evaporation of all volatiles, the residue was taken up in 6N HCl solution (30 ml) and refluxed for 15 min. The reaction mixture was filtered, slowly treated with 6N NaOH (30 ml) and extracted with AcOEt (3×200 ml). The organic phase was dried (Na₂SO₄), concentrated and the crude product obtained was chromatographed [silica, elution with (CH₂Cl₂/MeOH/aq. NH₄OH=90:10:1)] to obtain the free base of the title compound as a light brown semi-solid mass (2.62 g, 64%). After treatment with an equimolar amount of fumaric acid, the title compound was isolated as a white crystalline material. Mp. 176–177° C. (MeOH/Et₂O), MS: m/e=241 (M⁺).

EXAMPLE 306
N-1-(3,4-Dichloro-phenyl)-1H-imidazol-4-yl-methyl]-acetamide

To a solution of 1-(3,4-dichlorophenyl)-1H-imidazole-4-methanamine (0.20 g, 0.83 mmol) in THF (30 ml) was added triethylamine (0.079 g, 0.78 mmol) and acetyl chloride (0.082 mg, 1.0 mmol). The reaction mixture was stirred at rt for 12 h. After evaporation of the solvent, the residue was dissolved in AcOEt and washed with H₂O. The organic phase was dried (Na₂SO₄), concentrated and the obtained crude product was chromatographed [silica, elution with gradient CH₂Cl₂ to 100% (CH₂Cl₂/MeOH=9:1)]. The title compound was obtained as an off-white crystalline material (0.17 g, 74%). Mp. 177–180° C. (MeOH/CH₂Cl₂), MS: m/e=284 (M+H⁺).

EXAMPLE 307
N-[1-(3,4-Dichloro-phenyl)-1H-imidazol-4-yl-methyl]-thioacetamide To a suspension of N-[i-(3,4-dichloro-phenyl)-1H-imidazol-4-ylmethyl]-acetamide (1.1 g, 3.7 mmol) in 1,2 dimethoxyethane (11 ml) was added Lawesson's reagent (0.82 g, 2.0 mmol) and the mixture refluxed for 90 min. After addition of saturated NaHCO₃ solution (50 ml) and extraction with CH₂Cl₂ (3×100 ml) the combined organic phases were dried (Na₂SO₄), concentrated and the obtained crude product was chromatographed [silica, elution with gradient CH₂Cl₂ to 100% (CH₂Cl₂/MeOH=9:1)]. The title compound was obtained as a brown crystalline material (0.75 g, 68%). Mp. 166–170° C. (MeOH/CH₂Cl₂), MS: m/e=299 (M⁺).

EXAMPLE 308
1-[1-(3,4-Dichloro-phenyl)-1H-imidazol-4-yl-methyl]-1H-imidazole-2-carbaldehyde 4-Chloromethyl-1-(3,4-dichloro-phenyl)-1H-imidazole (1.31 g, 5.0 mmol) was dissolved in DMF (10 ml), 2-imidazolecarboxaldehyde (0.48 g, 5.0 mmol) and cesium carbonate (0.82 g, 2.5 mmol) was added and the resulting mixture was stirred at 60° C. for 12 h. After evaporation of the solvent the residue was dissolved in AcOEt and washed with H₂O. The organic phase was dried (Na₂SO₄), concentrated and chromatographed [silica, elution with gradient CH₂Cl₂ to 100% (CH₂Cl₂/MeOH=9:1)] to obtain 0.98 g (61%) of the title compound as an off-white solid. Mp. 130–131° C. (CH₂Cl₂/iPr₂O), MS: m/e=320 (M⁺).

EXAMPLE 309
1-(3,4-Dichloro-phenyl)-3-methyl-1H-pyrazole and 1-(3,4-Dichloro-phenyl)-5-methyl-1H-pyrazole A solution of of 3,4-dichlorophenylhydrazine (4.27 g, 20.0 mmol) in EtOH (50 ml) and H₂O (50 ml) was treated with 3-oxobutyraldehyde dimethyl acetal (2.64 g, 20.0 mmol) and refluxed for 1 h. The alcohol was removed in vacuo and the aqueous residue was extracted with AcOEt (2×150 ml). The organic phase was dried (Na₂SO₄), filtered and evaporated. The remaining oil was chromatographed [silica, elution with gradient hexane to 10% (hexane/AcOEt=1:1)] to obtain 3.01 g (66%) of 1-(3,4-dichloro-phenyl)-3-methyl-1H-pyrazole [Mp. 57–58° C. (AcOEt/hexane), MS: m/e=226 (M⁺)] as off-white crystals and 1.32 g (29%) of 1-(3,4-dichloro-phenyl)-5-methyl-1H-pyrazole [Mp. 46–47° C. (hexane), MS: m/e=226 (M⁺)] as white crystals.

EXAMPLE 310
4-Chloromethyl-1-(3,4-dichloro-phenyl)-1H-pyrazole 1-(3,4-Dichloro-phenyl)-1H-pyrazole-4-carboxylic acid (3.0 g, 12 mmol) (U.S. Pat. No. 5,064,851) as treated with IM BH₃ THF complex (50 ml) and refluxed for 90 min. The mixture was cooled to 5° C. and MeOH (50 ml) was added slowly. After evaporation of an volatiles the residue was taken up in 25% HCl solution (50 ml) and refluxed for 15 min. After filtration the aqueous phase was cooled in an ice-bath and slowly treated with 28% NaOH solution (50 ml). The title compound crystallizes as a light yellow material (2.6 g, 86%). Mp. 66–67° C. (H₂O), MS: m/e=260 (M⁺).

EXAMPLE 311
1-(3,4-Dichloro-phenyl)-1H-imidazole-4-carbaldehyde

A solution of [1-(3,4-dichloro-phenyl)-1H-imidazol-4-yl]-methanol (10.8 g, 44.3 mmol) in a mixture of THF (270 ml) and H₂O (30 ml) was treated with manganese(IV) oxide (5 g, 57.5 mmol) and the mixture was refluxed for 4 h. A second portion of manganese(IV) oxide (1.5 g) was added and reflux continued for 1.5 h. The mixture was filtered over Celite, and the residue was washed with MeOH. Toluene was added to the filtrate, and the H₂O was removed azeotropically. The brown residue was taken up in CH₂Cl₂ and upon standing white crystals formed. Filtration afforded 1-(3,4-dichloro-phenyl)-1H-imidazole-4-carbaldehyde (2.5 g, 25%). MS: m/e=240.0 (M⁺).

EXAMPLE 312
1-[1-(3,4-Dichloro-phenyl)-1H-imidazol-4-yl]-ethanol

To a solution of methylmagnesium iodide in ether (3 M, 13.7 ml, 41.1 mmol) and ether (40 ml), 1-(3,4-dichloro-phenyl)-1H-imidazole-4-carbaldehyde (2.58 g, 10.7 mmol) was added in portions. THF (50 ml) was then added slowly and stirring was continued for 1 h at reflux. After the addition of aqueous ammonium chloride (saturated, 30 ml), the mixture was extracted with AcOEt. The organic phase was dried (Na₂SO₄) and evaporated to give 1-[1-(3,4-dichloro-phenyl)-1H-imidazol-4-yl]-ethanol (2.56 g, 93%) as a light brown solid. MS: m/e=257.0 (M+H⁺).

EXAMPLE 313
1-(3,4-Dichloro-phenyl)-1H-imidazole-4-carboxylic Acid Methyl Ester A mixture of 1-(3,4-dichloro-phenyl)-1H-imidazole-4-carboxylic acid (7.0 g, 27 mmol), methanol (150 ml) and conc. sulfuric acid (25 ml) was refluxed for 3 h. The solution was then concentrated to 80 ml and a solution of sodium carbonate (60 g) in H$_2$O at 0° C. (500 ml) was added. Extraction with CH$_2$Cl$_2$, drying of the organic phase and evaporation of the solvent gave a brown residue, which upon triturating with ether gave the title compound (6.0 g, 81%) as a light brown solid. MS: m/e=269.9 (M$^+$).

EXAMPLE 314

2-[1-(3,4-Dichloro-phenyl)-1H-imidazol-4-yl]-propan-2-ol

In analogy to example 312, 1-(3,4-dichloro-phenyl)-1H-imidazole-4-carboxylic acid methyl ester (1.5 g, 5.53 mmol) was treated with excess methyl magnesium iodide. After extractive workup the title compound (1.3 g, 86%) was obtained. MS: m/e=270.1 (M$^+$).

EXAMPLE 315

1H-Imidazole, 2-[(2-methyl-1H-imidazol-1-yl)methyl]-4-[3-(trifluoromethyl)phenyl]-1-[[2-(trimethylsilyl)ethoxy]methyl]-

1H-Imidazole, 4-iodo-2-[(2-methyl-1H-imidazol-1-yl)methyl]-1-[[2-(trimethylsilyl)ethoxy]methyl]-(0.080 g, 0.191 mmol) was dissolved in toluene (4 ml) and MeOH (0.8 ml), treated with 2N Na$_2$CO$_3$ (0.2 ml), 3-(trifluoromethyl) phenylboronic acid (0.049 g, 0.248 mmol) and tetrakis (triphenylphosphine)palladium (0.0114 g, 0.0095 mmole). The reaction mixture was refluxed under argon for 150 h then cooled to rt and dried (Na$_2$SO$_4$). After filtration and evaporation of the solvent, the residue was chromatographed (silica, elution with CH$_2$Cl$_2$/MeOH=95:5) to provide the title compound (0.036 g, 43%) as a brown oil. MS: m/e=437.4 (M+H$^+$).

Examples 316 to 319 were prepared according to the general procedure described in example 315.

EXAMPLE 316

1H-Imidazole, 4-(4-fluoro-3-methylphenyl)-2-[(2-methyl-1H-imidazol-1-yl)methyl]-1-[[2-(trimethylsilyl)ethoxy]methyl]-

The title compound, MS: m/e=400.2 (M$^+$) was prepared from 1H-imidazole, 4-iodo-2-[(2-methyl-1H-imidazol-1-yl)methyl]-1-[[2-(trimethylsilyl)ethoxy]methyl]- and 4-fluoro-3-methylphenylboronic acid.

EXAMPLE 317

1H-Imidazole, 4-(3,4-difluorophenyl)-2-[(2-methyl-1H-imidazol-1-yl)methyl]-1-[[2-(trimethylsilyl)ethoxy]methyl]-

The title compound, MS: m/e=404.2 (Ma) was prepared from 1H-imidazole, 4-iodo-2-[(2-methyl-1H-imidazol-1-yl)methyl]-1-[[2-(trimethylsilyl)ethoxy]methyl]- and 3,4-difluorophenylboronic acid.

EXAMPLE 318

1H-Imidazole, 2-[(2-methyl-1H-imidazol-1-yl)methyl)-4-[4-(methylthio)phenyl]-1-[[2-(trimethylsilyl) ethoxy] methyl]-

The title compound, MS: m/e=414.2 (M$^+$) was prepared from from 1H-imidazole, 4-iodo-2-[(2-methyl-1H-imidazol-1-yl)methyl]-1-[[2-(trimethylsilyl)ethoxy] methyl]- and 4-methylthiophenylboronic acid.

EXAMPLE 319

1H-Imidazole, 4-(4-fluoro-3-methylphenyl)-2-(1H-imidazol-1-ylmethyl)-1-[[2-(trimethylsilyl) ethoxy]methyl]-

The title compound, MS: m/e=387.3 (M+H$^+$) was prepared from from 1H-imidazole, 2-(1H-imidazol-1-ylmethyl)-4-iodo-1-[[2-(trimethylsilyl)ethoxy]methyl]- and 4-fluoro-3-methylphenylboronic acid.

EXAMPLE 320

1H-Imidazole, 4-iodo-2-(2-methyl-1H-imidazol-1-yl) methyl]-1-[[2-(trimethylsilyl)ethoxy]methyl]-

[4-Iodo-1-(2-trimethylsilanyl-ethoxymethyl)-1H-imidazol-2-yl]-methanol (1.0 g, 2.8 mmol) and tetrabromomethane (1.3 g, 4.0 mmole) were dissolved in THF (10.0 ml) and cooled to 0° C. Triphenylphosphine (1.07 g, 3.95 mmol) was added portionwise over a period of 30 min. The reaction mixture was stirred at 0° C. for 1 h to provide a white suspension. In a second flask, sodium hydride (0.615 g, 14.1 mmol, 55% in mineral oil) was suspended in DMF (20 ml) and cooled to 0° C. 2-Methylimidazole (1.16 g, 14.1 mmol) was added portionwise. The reaction mixture was stirred at 60° C. for 30 min, cooled to 0° C. and treated with the above suspension. After 2 h stirring at rt, the reaction mixture was quenched with saturated NaHCO$_3$ (50 ml). The aqueous layer was extracted 3 times with AcOEt. The combined extracts were dried over Na$_2$SO$_4$, filtered and the solvent was removed in vacuo. The residue was chromatographed (silica, elution with CH$_2$Cl$_2$/MeOH=97:3) to provide the title compound (0.835 g, 71%) as a brown oil. MS: m/e=419.0 (M+H$^+$).

Example 321 was prepared according to the general procedure described in example 320.

EXAMPLE 321

1H-Imidazole, 2-(1H-imidazol-1-ylmethyl)-4-iodo-1-[[2-(trimethylsilyl)ethoxy]methyl]-

The title compound, MS: m/e=405.3 (M+H$^+$) was prepared from [4-iodo-1-(2-trimethylsilanyl-ethoxymethyl)-1H-imidazol-2-yl]-methanol and imidazole.

EXAMPLE 322

[4-Iodo-1-(2-trimethylsilanyl-ethoxymethyl)-1H-imidazol-2-yl]-methanol

4-Iodo-1-(2-trimethylsilanyl-ethoxymethyl)-1H-imidazole-2-carbaldehyde (4.6 g, 13.1 mmol) was dissolved in ethanol (50 ml) under argon. Sodium borohydride (0.514 g, 13.1 mmol) was added and the mixture was stirred at room temperature for 45 min. H$_2$O (200 ml) was added. The aqueous layer was extracted 3 times with AcOEt. The combined extracts were dried over Na$_2$SO$_4$, filtered and the solvent was removed in vacuo. The crude residue was taken up in hexane and stirred at rt. Filtration provided [4-iodo-1-(2-trimethylsilanyl-ethoxymethyl)-1H-imidazol-2-yl]-methanol (4.0 g, 87%) as a white solid. MS: m/e=354.0 (M$^+$).

EXAMPLE 323

4-Iodo-1-(2-trimethylsilanyl-ethoxymethyl)-1H-imidazole-2-carbaldehyde

A solution of 4,5-diiodo-1-(2-trimethylsilanyl-ethoxymethyl)-1H-imidazole (8.86 g, 19.68 mmol) in anhydrous THF (110 ml) under argon was cooled to −78° C. and was treated dropwise with n-butyllithium (13.5 ml, 21.65 mmol, 1.6M in hexane). After 10 minutes stirring at −78° C. and 30 minutes at −45° C., the reaction mixture was cooled to −78° C. and treated at once with DMF (10 ml). The mixture was allowed to warm to room temperature and saturated NH$_4$Cl (150 ml) was added. The aqueous layer was extracted 2 times with AcOEt. The combined extracts were dried over Na$_2$SO$_4$, filtered and the solvent was removed in vacuo. The residue was chromatographed (silica, elution with hexane/AcOEt=98:2) to provide the title compound (5.18 g, 75%) as a light yellow oil. MS: m/e 352.1 (M$^+$).

EXAMPLE 324
4,5-Diiodo-1-(2-trimethylsilanyl-ethoxymethyl)-1H-imidazole 4,5-Diiodoimidazole (prepared according to D. S. Carver, S. D. Lindell, and E. A. Saville-Stones, *Tetrahedron*, 1997, 53, 42, 14481–14496) (10.1 g, 31.6 mmol) was added portionwise to a room temperature suspension of sodium hydride (1.38 g, 31.6 mmol, 55% *in mineral oil) in dry DMF (45 ml). The reaction mixture was stirred at room temperature for 90 min, then cooled to 0° C. and treated slowly with a solution of 2-(trimethylsilyl)-ethoxymethylchloride (6.81 ml, 34.7 mmol) in DMF (10 ml). After 2 h stirring at 0° C., the reaction mixture was poured onto a mixture of $H_2O$ (200 ml) and AcOEt (50 ml). The mixture was filtered and the mother liquor was extracted 3 times with AcOEt. The combined extracts were dried over $Na_2SO_4$, filtered and the solvent was removed in vacuo. The residue was chromatographed (silica, elution with hexane/AcOEt=9:1) to provide the title compound (9.44 g, 66.4%) as a pale yellow oil. MS: m/e=450.0 ($M^+$).

EXAMPLE 325
3-Chloromethyl-5-(3,4-dichloro-phenyl)-pyridine Hydrochloride (1:1)

A solution of [5-(3,4-dichloro-phenyl)-pyridine-3-yl]-methanol (470 mg, 1.9 mmol) in thionyl chloride (4.9 ml) was stirred at 20° C. for 15 h. Evaporation of the thionyl chloride and drying under high vacuum at 50° C. for 2 h afforded the title compound (558 mg, 98%) as a light yellow solid. MS: m/e=271.0 ($M^+$).

Examples 326–328 were prepared according to the general procedure described in example 325.

EXAMPLE 326
2-Chloromethyl-3-(3,4-dichloro-phenyl)-pyridine Hydrochloride (1:1)

The title compound, MS: m/e=271.0 ($M^+$) was obtained as a light brown foam (99% yield) by the reaction of [4-(3,4-dichloro-phenyl)-pyridine 2-yl]-methanol with thionyl chloride at 20° C. for 15 h.

EXAMPLE 327
4-Chloromethyl-2-(3,4-dichloro-phenyl)-pyridine Hydrochloride (1:1)

The title compound, MS: m/e=271.0 ($M^+$) was obtained as a light brown foam (100% yield) by the reaction of [2-(3,4-dichloro-phenyl)-pyridine-4-yl]-methanol with thionyl chloride at 20° C. for 1 h.

EXAMPLE 328
3-Chloromethyl-5-(3,4-dimethyl-phenyl)-2-methyl-pyridine Hydrochloride (1:1)

The title compound, MS: m/e=245.1 ($M^+$) was obtained as a yellow solid (98% yield) by the reaction of [5-(3,4-dimethyl-phenyl)-2-methyl-pyridin-3-yl]-methanol hydrochloride (1:1) with thionyl chloride at 20° C. for 1 h then 2 h at reflux.

EXAMPLE 329
[5-(3,4-Dichloro-phenyl)-pyridine-3-yl]-methanol

To a suspension of $LiAlH_4$ (161 mg, 4.2 mmol) in THF (20 ml) at 0° C. was added dropwise 5-(3,4-dichloro-phenyl)-nicotinic acid methyl ester (2.0 g, 7.0 mmol) in THF (20 ml) and stirred for a further 2 h at this temperature. The reaction was quenched by careful addition of $THF/H_2O$ (9:1) and then dried directly with $Na_2SO_4$, filtered and the solvent was evaporated. The residue was chromatographed [silica, elution with $CH_2Cl_2/(2M\ NH_3\ MeOH)$=97:3] to afford the title compound (480 mg, 27%) as an orange solid. MS: m/e=254.0 ($M+H^+$).

Examples 330–332 were prepared according to the general procedure described in example 329.

EXAMPLE 330
[2-(3,4-Dichloro-phenyl)-pyridine-4-yl]-methanol

The title compound, MS: m/e=252.0 ([M-H]) was obtained as a light yellow solid (53% yield) by the reaction of 2-(3,4-dichloro-phenyl)-isonicotinic acid methyl ester with lithium aluminum hydride in THF at 20° C. for 1 h followed by chromatography [silica, elution with $CH_2Cl_2/$ (2M $NH_3$ MeOH) 19:1]

EXAMPLE 331
[4-(3,4-Dichloro-phenyl)-pyridine 2-yl]-methanol

The title compound, MS: m/e=252.0 ([M-H]-) was obtained as a light brown oil (94% yield) by the reaction of 4-(3,4-dichloro-phenyl)-pyridine-2-carboxylic acid methyl ester with 1M lithium aluminum hydride/THF solution in THF at 20° C. for 1 h followed by chromatographic purification.

EXAMPLE 332
[5-(3,4-Dimethyl-phenyl)-2-methyl-pyridin-3-yl]-methanol Hydrochloride (1:1)

The title compound, MS: m/e=227.2 ($M^+$) was obtained as a beige solid (58% yield) by the reaction of 5-(3,4-dimethyl-phenyl)-2-methyl-nicotinic acid ethyl ester with sodium borohydride (5 eq.) in EtOH (5 ml) stirred for 23 h at 20° C. followed by chromatographic purification.

EXAMPLE 333
5-(3,4-Dichloro-phenyl)-nicotinic Acid Methyl Ester

To a solution of 5-bromopyidine-3-carboxylic acid methyl ester (2 g, 9.3 mmol) in toluene (50 ml) was added tetrakis-(triphenylphosphine)-palladium (0) (320 mg, 0.28 mmol) followed by LiCl (785 mg, 18.5 mmol) and the mixture was stirred 30 min at 20° C. Then 3,4-dichlorophenyl boronic acid (50 wt % in $THF/H_2O$ 9:1) (3.7 g, 3.3 ml, 9.7 mmol) and 2N aq. $K_2CO_3$ (11.3 ml, 2.5 eq.) were added and the stirred mixture heated under an argon atmosphere at 100° C. for 23 h. After cooling, $H_2O$ was added (25 ml) and the aqueous phase separated and extracted with AcOEt. The combined organic extracts were washed with saturated NaCl solution, dried with $Na_2SO_4$, filtered and the solvent evaporated and the product dried under high vacuum at 50° C. for 2 h to afford the title compound (2.48 g, 95%) as a beige solid. MS: m/e=281.0 ($M+H^+$).

Examples 334–336 were prepared according to the general procedure described in example 333.

EXAMPLE 334
4-(3,4-Dichloro-phenyl)-pyridine-2-carboxylic Acid Methyl Ester

The title compound, MS: m/e=281.0 (Me) was obtained as a light yellow solid (10% yield) by the reaction of 4-bromo-pyridine-2-carboxylic acid methyl ester with 3,4-dichlorophenyl boronic acid.

EXAMPLE 335
[2-(3,4-Dichloro-phenyl)-isonicotinic Acid Methyl Ester

The title compound, MS: m/e=281.0 ($M^+$) was obtained as a light brown solid (59% yield) by the reaction of 2-iodo-isonicotinic acid methyl ester with 3,4-dichlorophenyl boronic acid.

EXAMPLE 336
6-(3,4-Dichloro-phenyl)-pyridine 2-carboxylic Acid Methyl Ester

The title compound, MS: m/e=282.0 (M$^+$) was obtained as a light yellow solid (7% yield) by the reaction of 6-bromo-pyridine-2-carboxylic acid methyl ester with 3,4-dichlorophenyl boronic acid.

EXAMPLE 337
2-Iodo-isonicotinic Acid Methyl Ester

A solution of 2-chloro-pyridine-4-carboxylic acid (5 g, 31.7 mmol) in butan-2-one (150 ml) was heated under reflux with sodium iodide for 6 h to afford the 2-iodo-isonicotinic acid (7.3 g, 92.4% yield) following extractive aqueous workup. This material was dissolved in THF (50 ml) and esterified with fresh etheral diazomethane solution (44 ml, 0.55 mol/l). After evaporation of the solvent and filtration through a pad of silica gel, [elution with CH$_2$Cl$_2$/(2M NH$_3$ MeOH)=19:1] the title compound (2.3 g, 44%) was obtained as a dark yellow oil. MS: m/e=263.0 (M$^1$).

EXAMPLE 338
3-Bromo-5-(2-methyl-imidazol-1-ylmethyl)-pyridine

To a stirred suspension of sodium hydride (0.54 g, 12.3 mmol) in THF (40 ml) at 20° C. was added 2-methylimidazole in portions over 45 min. 3-Bromo-5-(chloromethyl)-pyridine (1 g, 4.1 mmol) in ethanol (8 ml) was then added and this mixture was heated under reflux for 1 h under an argon atmosphere. After cooling and evaporation of solvents the residue was suspended in MeOH, filtered and adsorbed onto silica gel. Chromatographic elution with CH$_2$Cl$_2$/(2M NH$_3$ MeOH)=98:2 afforded the title compound (0.56 g, 53%) as a yellow oil. MS: m/e=251.0 (M$^+$).

EXAMPLE 339
3-Bromo-5-(chloromethyl)-pyridine

To a cooled solution of thionylchloride (41 ml, 344 mmol) at 0° C. was added cautiously (highly exothermic) portionwise (5-bromo-pyridin-3-yl)-methanol (10 g, 44.5 mmol). After complete addition the mixture was heated to reflux for 1 h to complete the reaction. After cooling, ether (50 ml) was added and the mixture cooled to 4° C. The precipitated solid was filtered off and washed with cold ether then dried at 50° C. under vacuum for 2 h to afford the title compound (9.1 g, 84%) as a light yellow solid. MS: m/e=206.9 (M$^+$).

EXAMPLE 340
(5-Bromo-pyridin-3-yl)-methanol Hydrochloride (1:1)

5-Bromo nicotinic acid ethyl ester (25 g, 108 mmol) was dissolved in ethanol (500 ml) and treated with fresh sodium borohydride (25 g, 660 mmol) added portionwise over 30 min. at 20° C. Stirring was continued overnight under an argon atmosphere. Following this 1N HCl (50 ml) was added slowly (over 20 min) followed by 2N NaOH (25 ml) and H$_2$O (75 ml) and this mixture was stirred for 2 h at ambient temperature. After evaporation of the alcohol the aqueous phase was extracted with dichloromethane (4×150 ml) and the combined extracts were washed with brine then dried with Na$_2$SO$_4$, filtered and evaporated. The resulting yellow oil was dissolved in a small volume of ethanol and treated with 0.93 M HCl/EtOH (62 ml, 1.2 eq.) at 4° C. over 1 h to afford, after removal of solvent and drying under high vacuum at 50° C. for 16 h, the title compound (10.9 g, 44%) as a light yellow solid. MS: m/e=186.9 (M-').

EXAMPLE 341
5-(3,4-Dimethyl-phenyl)-2-methyl-nicotinic Acid Ethyl Ester

Obtained from [3-dimethylamino-2-(3,4-dimethyl-phenyl) allylidine]-dimethyl-ammonium tetrafluoroborate (1:1) in turn prepared from 3,4-dimethyl-phenyl acetic acid (prepared according to A. J. Liepa; *Aust. J. Chem.*, 1981, 34(12), 2647–55).

EXAMPLE 342
2-(4-chloro-3-trifluoromethyl-phenyl)-4,4,5,5-tetramethyl-[1,3,2]dioxaborolane This compound was prepared in a modification of the literature known method (Y. Masuda, M. Murata, S. Watanabe, *J. Org. Chem.*, 1997, 62, 6458–9). To a flask containing KOAc (3.4 g, 34.7 mmol), PdCl$_2$(PPh$_3$)$_2$ (234 mg, 0.34 mmol) and bis(pinacolato)diboron (3.2 g, 12.7 mmol) was added a solution of 5-bromo-2-chloro-benzotrifluoride (3 g, 11.5 mmol) in dioxane. This mixture was heated to 100° C. under an argon atmosphere for 3 h. After cooling, AcOEt was added then the organic mixture was washed with saturated NaCl solution then dried with Na$_2$SO$_4$ and the solvent evaporated. The residue was chromatographed (silica, elution with hexane/AcOEt=9:1) to afford the title compound (2.35 g, 66%) as a light brown solid. MS: m/e=306.1 (M$^+$).

Examples 343 to 347 were prepared according to the general procedure described in example 342.

EXAMPLE 343
2-(3-Chloro-4-methyl-phenyl)-4,4,5,5-tetramethyl[1,3,2]-dioxaborolane The title compound, MS: m/e=252.1 (M$^+$) was obtained as a light yellow semi-solid (30% yield) using 2-chloro-4-iodo-toluene as the starting material.

EXAMPLE 344
2-(4-Chloro-3-methyl-phenyl)-4,4,5,5-tetramethyl[1,3,2]-dioxaborolane The title compound, MS: m/e=252.1 (M$^+$) was obtained as a colorless liquid (16% yield) using 5-bromo-2-chloro-toluene.

EXAMPLE 345
5-(4,4,5,5-Tetramethyl[1,3,2]-dioxaborolan-2-yl)-2,3-dihydro-benzofuran The title compound, MS: m/e=246.1 (M') was obtained as a light yellow oil (51% yield) using 2,3-dihydro-5-iodobenzo[b]furan.

EXAMPLE 346
2-Indan-5-yl-4,4,5,5-tetramethyl[1,3,2]-dioxaborolane

The title compound, MS: m/e=244.1 (M$^+$) was obtained as a light yellow oil (96% yield) using trifluoro-methanesulfonic acid indan-5-yl ester obtained in turn from indan-5-ol by treatment with trifluoro-methanesulfonic anhydride, DMAP and triethylamine in CH$_2$Cl$_2$ at −70° C. to 20° C.

EXAMPLE 347
2-(4-Fluoro-3-trifluoromethyl-phenyl)-4,4,5,5-tetramethyl-[1,3,2]dioxaborolane The title compound, MS: m/e=290.1 (Me) was obtained as a colourless oil (76% yield) using 5-bromo-2-fluoro-benzotrifluoride.

EXAMPLE 348
[1-(3-Trifluoromethylsulfanyl-phenyl)-1H-imidazol-4-yl]-methanol Following the general method described in example 293, 3-(trifluoromethylthio)aniline was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with $BH_3$ THF complex followed by hydrolytic workup and the title compound was obtained as a light brown crystalline solid. Mp. 73–75° C. ($H_2O$), MS: m/e=274 ($M^+$).

EXAMPLE 349
{1[3-(1,1-Difluoro-ethyl)-phenyl]-1H-imidazol-4-yl}-methanol

Following the general method described in example 293, 3-(1,1-difluoro-ethyl)-aniline [R. O. Neri, J. G. Topliss, Ger. Offen. (1972), DE 2130452 19721221 CAN 78:124310] was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with $BH_3$ THF complex followed by hydrolytic workup and the title compound was obtained as a white crystalline solid. Mp. 104–108° C. ($H_2O$), MS: m/e=238 ($M^+$).

EXAMPLE 350
{1-[3-(1,1-Difluoro-ethyl)-4-fluoro-phenyl]-1H-imidazol-4-yl}-methanol Following the general method described in example 293, 3-(1,1-difluoro-ethyl)-4-fluorophenylamine was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with $BH_3$ THF complex followed by hydrolytic workup and the title compound was obtained as a white crystalline solid. MS: m/e=257 (M+$H^+$).

EXAMPLE 351
3-(1,1-Difluoro-ethyl)-4-fluoro-phenylamine

To a solution of 2-(1,1-difluoro-ethyl)-1-fluoro-4-nitro-benzene (10.4 g, 50.6 mmol) in methanol (200 ml) palladium on carbon (10%, $^4$ g) was added and the resulting mixture was hydrogenated for 2 h at 20° C. After filtration of the catalyst the solvent was evaporated to yield the title compound as a yellow semi solid mass. (8.5 g, 96%). MS: m/e=175 ($M^+$).

EXAMPLE 352
2-(1,1-Difluoro-ethyl)-1-fluoro-4-nitro-benzene

A solution of 1-(2-fluoro-5-nitro-phenyl)-ethanone (10.8 g, 59.0 mmol) in diethylaminosulfur trifluoride (15.5 ml, 118 mmol) was stirred at 50° C. for 6 h. The mixture was cooled in an ice bath and slowly added to ice cooled aqueous 2N NaOH solution (100 ml). After extraction with $CH_2Cl_2$ the organic phase was dried ($Na_2SO_4$), and concentrated. After chromatography (silica, elution with AcOEt/hexane=1:4) the title compound was obtained as a dark brown oil (9.8 g, 81%). MS: m/e=205 ($M^+$).

EXAMPLE 353
1-(3-Isopropyl-phenyl)-1H-imidazole-4-carboxylic Acid

Following the general method described in example 234, 3-isopropylaniline was reacted with triethyl orthoformate, ethyl nitroacetate and acetic acid followed by treatment with triethyl orthoformate, iron and acetic acid and subsequent alkaline hydrolysis. The title compound was obtained as a light brown crystalline solid. Mp.>122° C. dec. ($H_2O$/dioxane), MS: m/e=231 (M+$H^+$).

EXAMPLE 354
[1-(3-Isopropyl-phenyl)-1H-imidazol-4-yl]-methanol

Following the general method described in example 264, 1-(3-isopropyl-phenyl)-1H-imidazole-4-carboxylic acid was reacted with $BH_3$ THF complex followed by hydrolytic workup. The title compound was obtained as a light brown crystalline solid. Mp. 76–77° C. ($H_2O$), MS: m/e=216 ($M^+$).

EXAMPLE 355
1-Naphthalen-2-yl-1H-imidazole-4-carboxylic Acid Methyl Ester

A suspension of 2-naphtylboronic acid (1.4 g, 8 mmol), 1H-imidazole-4-carboxylic acid methyl ester (1.0 g, 8 mmol) and cupric acetate (1.4 g, 8 mmol) in $CH_2Cl_2$ (20 ml) was stirred at 20° C. for 24 h. AcOEt (100 ml) and saturated aqueous Seignette salt solution (50 ml) was added and the resulting mixture was stirred for another 2 h. After separation the organic phase was dried ($Na_2SO_4$), concentrated and chromatographed (silica, elution with $CH_2Cl_2$/MeOH 99:1) to yield the title compound (0.49 g, 24%) of the title compound as a white crystalline material. Mp. 143–144° C. (AcOEt), MS: m/e=252 ($M^+$).

EXAMPLE 356
(1-Naphthalen-2-yl-1H-imidazol-4-yl)-methanol

Following the general method described in example 298) 1-naphthalen-2-yl-1H-imidazole-4-carboxylic acid methyl ester was reacted with lithium aluminum hydride followed by hydrolytic workup and chromatography. The title compound was obtained as a light brown gum. MS: m/e=225 ($M^+$).

EXAMPLE 357
[1-(3-Bromo-4-fluoro-phenyl)-1H-imidazol-4-yl]-methanol

Following the general method described in example 293, 3-bromo-4-fluoroaniline (K. S. Y. Lau et al., *J. Org. Chem.*, 1981, 46, 2280–6) was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with $BH_3$ THF complex followed by hydrolytic workup and the title compound was obtained as a white crystalline solid. Mp. 151–152° C. ($H_2O$), MS: m/e=270 ($M^+$).

EXAMPLE 358
1-(3-Bromo-phenyl)-1H-imidazole-4-carboxylic Acid

Following the general method described in example 234, 3-bromoaniline was reacted with triethyl orthoformate, ethyl nitroacetate and acetic acid followed by treatment with triethyl orthoformate, iron and acetic acid and subsequent alkaline hydrolysis. The title compound was obtained as a light brown crystalline solid. Mp. 205–207° C. ($H_2O$/dioxane), MS: m/e=267 (M−$H^-$).

EXAMPLE 359
[1-(3-Bromo-phenyl)-1H-imidazol-4-yl]-methanol

Following the general method described in example 264, 1-(3-bromo-phenyl)-1H-imidazole-4-carboxylic acid was reacted with $BH_3$ THF complex followed by hydrolytic workup. The title compound was obtained as an off-white solid. MS: m/e=253 (M+$H^+$).

EXAMPLE 360
[1-(3-Vinyl-phenyl)-1H-imidazol-4-yl]-methanol

Under an Ar atmosphere, a solution of [1-(3-bromo-phenyl)-1H-imidazol-4-yl]-methanol (3.0 g, 12 mmol) in DMF (90 ml) was successively treated with $PdCl_2(PPh_3)_2$ (0.87 g, 0.1 mmol) and vinyltributylstannane (4.1 g, 13 mmol). The resulting mixture was heated to 60° C. for 8 h. After evaporation of the solvent the residue was stirred for 30 min with AcOEt (60 ml) and aqueous 10% KF solution. The organic phase was separated and the aqueous phase was extracted 3 times with AcOEt. The combined organic phases were dried ($Na_2SO_4$), concentrated and chromatographed [silica, elution with gradient $CH_2Cl_2$ to 40% ($CH_2Cl_2$/MeOH=9:1)] to yield the title compound as a colorless oil (1.2 g, 51%). MS: m/e=201 ($M+H^+$).

EXAMPLE 361
[1-(3-Cyclopropyl-phenyl)-1H-imidazol-4-yl]-methanol

Under an Ar atmosphere, a mixture of [1-(3-vinyl-phenyl)-1H-imidazol-4-yl]-methanol (0.10 g, 0.5 mmol) in toluene (20 ml) was successively treated with diethylzinc (3.8 ml of a 1.1 M solution in hexane, 4.2 mmol) and diiodomethane (6.6 g, 25 mmol). The resulting mixture was stirred at 20° C. for 12 h. The preciptate was filtered and stirred for 30 min with AcOEt and saturated aqueous $NH_4Cl$ solution. The organic phase was separated, dried ($Na_2SO_4$) and concentrated to yield the title compound as a yellow oil (0.10 g, 93%). MS: m/e=215 ($M+H^+$).

EXAMPLE 362
2-Difluoromethyl-1-fluoro-4-nitro-benzene

A solution of 2-fluoro-5-nitrobenzaldehyde (1.7 g, 10 mmol) in $CH_2Cl_2$ (50 ml) was treated with diethylaminosulfur trifluoride (1.8 ml, 14 mmol) and stirred at 20° C. for 72 h. Then saturated aqueous $NaHCO_3$ solution (200 ml) was added and the mixture was stirred for 1 h. The organic phase was separated, dried ($Na_2SO_4$) and chromatographed [silica, elution with gradient hexane to 100% (hexane/AcOEt=3:1)] to yield the title compound as a colorless oil (1.4 g, 74%). MS: m/e=191 ($M^+$).

EXAMPLE 363
3-Difluoromethyl-4-fluoroaniline Hydrochloride (1:1)

To a mixture of powdered iron (88.0 g, 1.58 mol) in acetic acid (500 ml) at 120° C. 2-difluoromethyl-1-fluoro-4-nitro-benzene (25.0 g, 131 mmol) was slowly added. After completed addition stirring was continued for 15 min, the reaction mixture was cooled to 20° C., filtered and evaporated. The residue was stirred with AcOEt (1l), filtered, evaporated and chromatographed [silica, elution with gradient hexane to 100% (hexane/AcOEt=2:1)] to yield the free base of the title compound as a dark brown oil (15.11 g, 72%). An analytical sample was treated with HCl and crystallized as the white hydrochloride salt. Mp.>240° C. dec. (MeOH/$Et_2O$), MS: m/e=161 ($M^+$).

EXAMPLE 364
1-(3-Difluoromethyl-4-fluoro-phenyl)-1H-imidazole-4-carboxylic Acid Following the general method described in example 234, 3-difluoromethyl-4-fluoroaniline was reacted with triethyl orthoformate, ethyl nitroacetate and acetic acid followed by treatment with triethyl orthoformate, iron and acetic acid and subsequent alkaline hydrolysis. The title compound was obtained as a light brown crystalline solid. Mp.>247° C. dec. ($H_2O$/dioxane), MS: m/e=255 ($M-H^-$).

EXAMPLE 365
[1-(3-Difluoromethyl-4-fluoro-phenyl)-1H-imidazol-4-yl]-methanol Following the general method described in example 264, 1-(3-difluoromethyl-4-fluoro-phenyl)-1H-imidazole-4-carboxylic acid was reacted with $BH_3$ THF complex followed by hydrolytic workup. The title compound was obtained as an off-white solid. Mp. 133–134° C. ($H_2O$), MS: m/e=242 ($M^+$).

EXAMPLE 366
1-(3-Methylsulfanyl-phenyl)-1H-imidazole-4-carboxylic Acid

Following the general method described in example 234, 3-(methylthio)aniline was reacted with triethyl orthoformate, ethyl nitroacetate and acetic acid followed by treatment with triethyl orthoformate, iron and acetic acid and subsequent alkaline hydrolysis. The title compound was obtained as a grey crystalline solid. Mp. 190–192° C. ($H_2O$/dioxane), MS: m/e=234 ($M^+$).

EXAMPLE 367
[1-(3-Methylsulfanyl-phenyl)-1H-imidazol-4-yl]-methanol

Following the general method described in example 264, 1-(3-methylsulfanyl-phenyl)-1H-imidazole-4-carboxylic acid was reacted with $BH_3$ THF complex followed by hydrolytic workup. The title compound was obtained as an off-white solid. Mp.>120° C. dec. ($H_2O$), MS: m/e=221 ($M+H^+$).

EXAMPLE 368
1-(3-Trifluoromethoxy-phenyl)-1H-imidazole-4-carboxylic Acid

Following the general method described in example 234, 3-(trifluoromethoxy)aniline was reacted with triethyl orthoformate, ethyl nitroacetate and acetic acid followed by treatment with triethyl orthoformate, iron and acetic acid and subsequent alkaline hydrolysis. The title compound was obtained as a grey crystalline solid. Mp. 173–175° C. (1($H_2O$ dioxane), MS: m/e=273 ($M+H^+$).

EXAMPLE 369
[1-(3-Trifluoromethoxy-phenyl)-1H-imidazol-4-yl]-methanol

Following the general method described in example 264, 1-(3-trifluoromethoxy-phenyl)-1H-imidazole-4-carboxylic acid was reacted with $BH_3$ THF complex followed by hydrolytic workup. The title compound was obtained as an off-white solid. MS: m/e=258 ($M^+$).

EXAMPLE 370
[1-(3-Chloro-phenyl)-1H-imidazol-4-yl]-methanol

Following the general method described in example 293, 3-chloroaniline was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with $BH_3$ THF complex followed by hydrolytic workup and the title compound was obtained as an off-white crystalline solid. Mp. 78–79° C. ($H_2O$), MS: m/e=209 ($M+H^+$).

EXAMPLE 371
1-(3-Iodo-phenyl)-1H-imidazole-4-carboxylic Acid

Following the general method described in example 234, 3-iodoaniline was reacted with triethyl orthoformate, ethyl nitroacetate and acetic acid followed by treatment with triethyl orthoformate, iron and acetic acid and subsequent alkaline hydrolysis. The title compound was obtained as an off-white crystalline solid. Mp. 229–230 C (H$_2$O/dioxane), MS: m/e=313(M–H).

EXAMPLE 372
[1-(3-Iodo-phenyl)-1H-imidazol-4-yl]-methanol

Following the general method described in example 264, 1-(3-iodo-phenyl)-1H-imidazole-4-carboxylic acid was reacted with BH$_3$ THF complex followed by hydrolytic workup. The title compound was obtained as a yellow oil. MS: m/e=301 (M+H$^+$).

EXAMPLE 373
1-(3-Fluoro-5-trifluoromethyl-phenyl)-1H-imidazole-4-carboxylic Acid Following the general method described in example 234, 3-fluoro-5-trifluoromethylaniline was reacted with triethyl orthoformate, ethyl nitroacetate and acetic acid followed by treatment with triethyl orthoformate, iron and acetic acid and subsequent alkaline hydrolysis. The title compound was obtained as a white crystalline solid. Mp.>250° C. (H$_2$O/dioxane), MS: m/e=273 (M–H$^-$).

EXAMPLE 374
[1-(3-Fluoro-5-trifluoromethyl-phenyl)-1H-imidazol-4-yl]-methanol Following the general method described in example 264, 1-(3-fluoro-5-trifluoromethyl-phenyl)-1H-imidazole-4-carboxylic acid was reacted with BH$_3$ THF complex followed by hydrolytic workup. The title compound was obtained as a white crystalline solid. Mp. 144–145° C. (H$_2$O), MS: m/e=261 (M+H$^+$).

EXAMPLE 375
[1-(3-Methoxy-5-trifluoromethyl-phenyl)-1H-imidazol-4-yl]-methanol Following the general method described in example 293, 3-methoxy-5-trifluoromethylaniline was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with BH$_3$ THF complex followed by hydrolytic workup and the title compound was obtained as a light brown crystalline solid. Mp. 133–134° C. (H$_2$O), MS: m/e=272 (M$^+$)

EXAMPLE 376
[1-(3-tert-Butyl-phenyl)-1H-imidazol-4-yl]-methanol

Following the general method described in example 293, 3-tert-butylaniline was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with BH$_3$ THF complex followed by hydrolytic workup and the title compound was obtained as a colorless oil. MS: m/e=230 (M$^+$).

EXAMPLE 377
1-(3-Chloro-4-trifluoromethoxy-phenyl)-1H-imidazole-4-carboxylic Acid Following the general method described in example 234, 3-chloro-5-(trifluoromethoxy)aniline was reacted with triethyl orthoformate, ethyl nitroacetate and acetic acid followed by treatment with triethyl orthoformate, iron and acetic acid and subsequent alkaline hydrolysis. The title compound was obtained as a light brown crystalline solid. Mp. 230–231° C. (H$_2$O/dioxane), MS: m/e=305 (M–H).

EXAMPLE 378
[1-(3-Chloro-4-trifluoromethoxy-phenyl)-1H-imidazol-4-yl]-methanol Following the general method described in example 264, 1-(3-chloro-4-trifluoromethoxy-phenyl)-1H-imidazole-4-carboxylic acid was reacted with BH$_3$ THF complex followed by hydrolytic workup. The title compound was obtained as a white crystalline solid. Mp. 115–116° C. (H$_2$O), MS: m/e=292 (M$^+$).

EXAMPLE 379
1-(3-Difluoromethoxy-phenyl)-1H-imidazole-4-carboxylic Acid

Following the general method described in example 234, 3-(difluoromethoxy)aniline was reacted with triethyl orthoformate, ethyl nitroacetate and acetic acid followed by treatment with triethyl orthoformate, iron and acetic acid and subsequent alkaline hydrolysis. The title compound was obtained as a light brown crystalline solid. Mp. 190–191° C. (H$_2$O/dioxane), MS: m/e=253 (M–H$^-$).

EXAMPLE 380
[1-(3-Difluoromethoxy-phenyl)-1H-imidazol-4-yl]-methanol

Following the general method described in example 264, 1-(3-difluoromethoxy-phenyl)-1H-imidazole-4-carboxylic acid was reacted with BH$_3$ THF complex followed by hydrolytic workup. The title compound was obtained as a white crystalline solid. MS: m/e=240 (M$^+$).

EXAMPLE 381
[1-(3-Difluoromethyl-phenyl)-1H-imidazol-4-yl]-methanol

Following the general method described in example 293, 3-difluoromethylaniline (G. E. Wright et al., *J. Med. Chem.*, 1995, 38, 49–57) was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with BH$_3$ THF complex followed by hydrolytic workup and the title compound was obtained as a light brown solid. MS: m/e=225 (M+H$^+$).

EXAMPLE 382
[1-(3-Bromo-5-fluoro-phenyl)-1H-imidazol-4-yl]-methanol

Following the general method described in example 293, 3-bromo-5-fluoroaniline (K. Yoshiizumi et al., *Bioorg. Med. Chem. Lett.*, 1998, 8, 3397–3402) was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with BH$_3$ THF complex followed by hydrolytic workup and the title compound was obtained as a light brown solid. Mp. 134–138° C. (AcOEt/hexane), MS: m/e=271 (M+H$^+$).

EXAMPLE 383
[1-(2,2-Difluoro-benzo[1,3]dioxol-5-yl)-1H-imidazol-4-yl]-methanol Following the general method described in example 293, 2,2-difluoro-benzo[1,3]dioxol-5-ylamine was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with BH$_3$ THF complex followed by hydrolytic workup and the title compound was obtained as a light brown solid. Mp. 163–164° C. (H$_2$O), MS: m/e=254 (M$^+$).

EXAMPLE 384

1-Quinolin-2-yl-1H-imidazole-4-carboxylic Acid Ethyl Ester

A mixture of 2-aminoquinoline (10.0 g, 69 mmol), triethyl orthoformate (140 ml, excess), ethyl nitroacetate (9.2 g, 69 mmol) and acetic acid (1 ml) was refluxed for 3 h. Acetic acid (140 ml) and iron powder (11.6 g, 208 mmol) was added and the mixture was refluxed for 5 h. During this time 3 additional portions of iron powder (each 11.6 g, 208 mmol) were added. The mixture was cooled to 60° C. and AcOEt (500 ml) was added. After refluxing for 10 min the precipitate was filtered and the filtrate was concentrated. Residual acetic acid was azeotropically removed by coevaporation with toluene (500 ml). After chromatography (silica, elution with gradient hexane to AcOEt) the title compound was obtained as an off-white crystalline material (12.2 g, 66%). Mp. 129–130° C. (AcOEt/hexane), MS: m/e=268 (M+H$^+$).

EXAMPLE 385

(1-Quinolin-2-yl-1H-imidazol-4-yl)-methanol

Following the general method described in example 298, 1-quinolin-2-yl-1H-imidazole-4-carboxylic acid ethyl ester was reacted with lithium aluminum hydride followed by hydrolytic workup and chromatography. The title compound was obtained as an off-white crystalline material. Mp. 136–137° C. (EtOH), MS: m/e=225 (M$^+$).

EXAMPLE 386

[1-(3-Chloro-4-trifluoromethylsulfanyl-phenyl)-1H-imidazol-4-yl]-methanol

Following the general method described in example 293, 3-chloro-4-(trifluoromethylthio)aniline was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with BH$_3$ THF complex followed by hydrolytic workup and the title compound was obtained as a light brown crystalline solid. Mp. 105–106° C. (H$_2$O), MS: m/e=308 (M$^+$).

EXAMPLE 387

1-Quinolin-3-yl-1H-imidazole-4-carboxylic Acid Ethyl Ester

Following the general method described in example 384, 2-aminoquinoline was reacted with triethyl orthoformate, ethyl nitroacetate and acetic acid followed by treatment with triethyl orthoformate, iron and acetic acid. After workup and chromatography the title compound was obtained as a beige crystalline solid. Mp. 170–171° C. (AcOEt/hexane), MS: m/e=267 (M$^+$).

EXAMPLE 388

(1-Quinolin-3-yl-1H-imidazol-4-yl)-methanol

A suspension of 1-quinolin-3-yl-1H-imidazole-4-carboxylic acid ethyl ester (5.0 g, 18.7 mmol) in toluene (100 ml) was cooled to −78° C. Diisobutylaluminum hydride (19 ml of a IM solution in THF, 19 mmol) was added dropwise keeping T <−70° C. The mixture was stirred at this temperature for 2 h, then the reaction mixture was allowed to slowly reach 0° C. After addition of saturated aqueous Seignette salt solution (10 ml) stirring was continued for 1 h. The mixture was diluted with AcOEt (100 ml), filtered, concentrated and chromatographed [silica, elution with gradient CH$_2$Cl$_2$ to 80% (CH$_2$Cl$_2$/MeOH/aq. NH$_4$OH=90:10:1)]. The title compound was obtained as a light brown crystalline solid (1.20 g, 28%). Mp. 142–145° C. (AcOEt), MS: m/e=226 (M+H$^+$).

EXAMPLE 389

1-(5-Chloro-pyridin-2-yl)-1H-imidazole-4-carboxylic Acid Ethyl Ester

Following the general method described in example 384, 2-amino-5-chloropyridine was reacted with triethyl orthoformate, ethyl nitroacetate and acetic acid followed by treatment with triethyl orthoformate, iron and acetic acid. After workup and chromatography the title compound was obtained as a beige crystalline solid. Mp. 163–164° C. (AcOEt), MS: m/e=252 (M+H$^+$).

EXAMPLE 390

[1-(5-Chloro-pyridin-2-yl)-1H-imidazol-4-yl]-methanol

Following the general method described in example 388, 1-(5-chloro-pyridin-2-yl)-1H-imidazole-4-carboxylic acid ethyl ester was reacted with diisobutylaluminum hydride.

After hydrolytic workup and chromatography the title compound was obtained as a light brown crystalline solid. Mp. 82–87° C. (AcOEt/Et$_2$O), MS: m/e=210 (M+H$^+$).

EXAMPLE 391

1-Isoquinolin-3-yl-1H-imidazole-4-carboxylic Acid Ethyl Ester

Following the general method described in example 384, 3-aminoquinoline was reacted with triethyl orthoformate, ethyl nitroacetate and acetic acid followed by treatment with triethyl orthoformate, iron and acetic acid. After workup and chromatography the title compound was obtained as a beige crystalline solid. Mp. 161–162° C. (AcOEt), MS: m/e=268 (M+H$^+$).

EXAMPLE 392

(1-Isoquinolin-3-yl-1H-imidazol-4-yl)-methanol

Following the general method described in example 298, 1-isoquinolin-3-yl-1H-imidazole-4-carboxylic acid ethyl ester was reacted with lithium aluminum hydride followed by hydrolytic workup and chromatography. The title compound was obtained as an off-white waxy solid. MS: m/e=226 (M+H$^+$).

EXAMPLE 393

[1-(4-Trifluoromethoxy-phenyl)-1H-imidazol-4-yl]-methanol

Following the general method described in example 293, 4-(trifluoromethoxy)aniline was reacted with triethyl orthoformate, ethyl nitroacetate and acetic acid followed by treatment with triethyl orthoformate, iron and acetic acid and subsequent alkaline hydrolysis. The isolated acid was directly reduced according to example 264, by reaction with BH$_3$ THF complex followed by hydrolytic workup and the title compound was obtained as a white crystalline material. Mp. 105–106° C. (Et$_2$O), MS: m/e=258 (M$^+$).

EXAMPLE 394

1-(4-Trifluoromethylsulfanyl-phenyl)-1H-imidazole-4-carboxylic Acid

Following the general method described in example 234, 4-(trifluoromethylthio)aniline was reacted with triethyl orthoformate, ethyl nitroacetate and acetic acid followed by treatment with triethyl orthoformate, iron and acetic acid and subsequent alkaline hydrolysis. The title compound was obtained as a light brown crystalline solid. Mp. 247–248° C. (H$_2$O/dioxane), MS: m/e=288 (M$^+$).

EXAMPLE 395

[1-(4-Trifluoromethylsulfanyl-phenyl)-1H-imidazol-4-yl]-methanol

Following the general method described in example 264, 1-(4-trifluoromethylsulfanyl-phenyl)-1H-imidazole-4- carboxylic acid was reacted with BH₃ THF complex followed by hydrolytic workup. The title compound was obtained as an off-white crystalline solid. Mp. 145–147° C. (H₂O), MS: m/e=275 (M+H⁺).

EXAMPLE 396
1-Quinolin-6-6-yl-1H-imidazole-4-carboxylic Acid Ethyl Ester

Following the general method described in example 384, 6-aminoquinoline was reacted with triethyl orthoformate, ethyl nitroacetate and acetic acid followed by treatment with triethyl orthoformate, iron and acetic acid. After workup and chromatography the title compound was obtained as a brown crystalline solid. Mp. 90–94° C. (AcOEt/hexane), MS: m/e= 268 (M+H⁺).

EXAMPLE 397
(1-Quinolin-6-yl-1H-imidazol-4-yl)-methanol

Following the general method described in example 388, 1-quinolin-6-yl-1H-imidazole-4-carboxylic acid ethyl ester was reacted with diisobutylaluminum hydride. After hydrolytic workup and chromatography the title compound was obtained as a light brown crystalline solid. Mp. 183–187° C. (AcOEt/hexane), MS: m/e=226 (M+H⁺).

EXAMPLE 398
1-Quinolin-8-yl-1H-imidazole-4-carboxylic Acid Ethyl Ester

Following the general method described in example 384, 8-aminoquinoline was reacted with triethyl orthoformate, ethyl nitroacetate and acetic acid followed by treatment with triethyl orthoformate, iron and acetic acid. After workup and chromatography the title compound was obtained as a light brown crystalline solid. Mp.>92° C. dec. (AcOEt/hexane), MS: m/e=267 (M⁺).

EXAMPLE 399
(1-Quinolin-8-yl-1H-imidazol-4-yl)-methanol

Following the general method described in example 388, 1-quinolin-8-yl-1H-imidazole-4-carboxylic acid ethyl ester was reacted with diisobutylaluminum hydride. After hydrolytic workup and chromatography the title compound was obtained as a light brown crystalline solid. Mp. 168–170° C. (Et₂O), MS: m/e=225 (M⁺).

EXAMPLE 400
1H-Imidazole, 1-1-(1,3-benzodioxol-5-yl)-1H-imidazol-4-yl]methyl]-2-nitro- Following the general method described in example 301 (1-benzo[1,3]dioxol-5-yl-1H-imidazol-4-yl)-methanol was treated first with thionylchloride, then with 2-nitroimidazole and cesium carbonate. After evaporation, extractive workup and chromatography the title compound was obtained as a light brown solid. Mp.>156° C. dec. (CH₂Cl₂/iPr₂O), MS: m/e=314 (M+H⁺).

EXAMPLE 401
2-(3-Difluoromethyl-4-fluoro-phenyl)-4,4,5,5-tetramethyl-[1,3,2]dioxaborolane The title compound was obtained according to example 342 as a colorless oil (54% yield) using 4-bromo-2-difluoromethyl-1-fluoro-benzene and bis(pinacolato) diboron as the starting materials. MS: m/e=272 (M⁺).

EXAMPLE 402
2-[3-(1,1-Difluoro-ethyl)-phenyl]-4,4,5,5-tetramethyl-[1,3,2]dioxaborolane The title compound was obtained according to example 342 as a colorless oil (60% yield) using 1-bromo-3-(1,1-difluoro-ethyl)-benzene and bis(pinacolato)diboron as the starting materials. MS: m/e=268 (M').

EXAMPLE 403
2-(3-Fluoro-5-trifluoromethyl-phenyl)-4,4,5,5-tetramethyl-[1,3,2]dioxaborolane The title compound was obtained according to example 342 as a colorless oil (48% yield) using 3-bromo-5-fluorobenzotrifluoride and bis(pinacolato)diboron as the starting materials MS: m/e=290 (M⁺).

EXAMPLE 404
2-[3-(1,1-Difluoro-ethyl)-4-fluoro-phenyl]-4,4,5,5-tetramethyl-[1,3,2]dioxaborolane The title compound was obtained according to example 342 as an orange oil (28% yield) using 4-bromo-2-(1,1-difluoro-ethyl)-1-fluoro-benzene and bis(pinacolato)diboron as the starting materials. MS: m/e=286.2 (M⁺).

EXAMPLE 405
4-Bromo-2-difluoromethyl-1-fluoro-benzene

5-Bromo-2-fluorobenzaldehyde (2 g, 9.85 mmol) was dissolved in CH₂Cl₂ (50 ml). The reaction mixture was put under an argon atmosphere and cooled to 0° C. Diethylaminosulfur trifluoride (2.04 ml, 14.78 mmol) was added dropwise. The mixture was allowed to warm up to room temperature and stirred overnight. It was then quenched with a saturated aqueous NaHCO₃ solution. The layers were separated and the aqueous one was extracted with CH₂Cl₂. The combined organic phases were dried with Na₂SO₄ and the solvent evaporated. The brown oil was chromatographed (silica, elution hexane/AcOEt) to afford the title compound (1.55 g, 70%) as a colorless oil. MS: m/e=226.0 (M+H⁺).

EXAMPLE 406
1-Bromo-3-(1,1-difluoro-ethyl)-benzene

The title compound was obtained according to example 405 (neat diethylaminosulfur trifluoride) as a colorless oil (15% yield) using 3-bromoacetophenone as the starting material. MS: m/e=220.0 (M⁺).

EXAMPLE 407
1-(2-Fluoro-5-nitro-phenyl)-ethanone

The title compound was prepared following the literature method M. Q. Zhang, A. Haemers, D. Vanden Berghe, S. R. Pattyn, W. Bollaert, *J. Heterocyclic Chem.*, 1991, 28, 673–683, using 2'-fluoroacetophenone as the starting material. The reaction afforded a light yellow solid (85%). MS: m/e=205.0 (M⁺).

EXAMPLE 408
4-Bromo-2-(1,1-difluoro-ethyl)-1-fluoro-benzene

The title compound was prepared following the literature method (A. Takahashi, T. Agatsuma, M. Matsuda, T. Ohta, T. Nunozawa, T. Endo, S. Nozoe, *Chem. Pharm. Bull.,* 1992, 40, 3185–3188), using 3-(1)1-difluoro-ethyl)-4-fluorophenylamine as the starting material. The reaction afforded a dark red liquid (yield 46%). ¹H-NMR (400 MHz)δ=1.99 (t, J=11.75 Hz, 3H), 7.02 (t, J=6.0 Hz, 1H), 7.50–7.55 (m, 1H), 7.65–7.69 (m, 1H).

EXAMPLE 409

2-Cyclopropyl-1H-imidazole

To a solution of cyclopropanecarboximidic acid ethyl ester (32.9 g, 291 mmol) in MeOH (40 ml) was added aminoacetaldehyddimethylacetal (34.5 ml, 320 mmol) and the reaction mixture was stirred for 2 days. The reaction mixture was concentrated, conc HCl and water was added and the mixture was concentrated again. The residue was dissolved in water and the pH was adjusted to 8 by additon of $Na_2CO_3$ and the mixture was concentrated. The brown residue was suspended in EtOH and filtered. The filtrate was concentrated to give 30.6 g (283 mmol, 97%) of the title compound. MS: m/e=107.1 (M–H).

EXAMPLE 410

Cyclopropanecarboximidic Acid Ethyl Ester Hydrochloride

A steady stream of HCl gas was slowly passed through a solution of cyclopropancarbonitril (25 g, 373 mmol) in EtOH (17.2 ml). After 15 h the reaction mixture was cooled to 0° C. and diethylether was added dropwise. The precipitated title compound was filtered and obtained as a colourless crystalline material (32.9 g, 220 mmol, 59%). MS: m/e=112.2 (M–H).

EXAMPLE 411

5-Bromo-1-methyl-2-(2-methyl-imidazol-1-ylmethyl)-1H-imidazole (5-Bromo-1-methyl-1H-imidazol-2-yl)-methanol (1.0 g, 5.24 mmol) and tetrabromomethane (2.48 g, 7.33 mmol) were dissolved in THF (10.0 ml) and cooled to 0° C. Triphenylphosphine (1.98 g, 7.33 mmol) was added portionwise over a period of 30 min. The reaction mixture was stirred at 0° C. for 1 h to provide a white suspension. In a second flask, NaH (1.05 g, 26.18 mmol, 60% in mineral oil) was suspended in DMF (20 ml) and cooled to 0° C. 2-Methylimidazole (2.15 g, 26.2 mmol) was added portionwise. The reaction mixture was stirred at 60° C. for 30 min, cooled to 0° C. and treated with the above suspension. After 2 h stirring at room temperature, the reaction mixture was quenched with aqueous saturated $NaHCO_3$ solution (50 ml). The aqueous layer was extracted 3 times with AcOEt. The combined extracts were dried over $Na_2SO_4$, filtered and the solvent was removed in vacuo. The residue was chromatographed (silica, elution with $CH_2Cl_2$/MeOH=95:5) to provide the title compound (0.7 g, 52%) as a brown solid. MS: m/e=255.0 (M+).

EXAMPLE 412

(5-Bromo-1-methyl-1H-imidazol-2-yl)-methanol

1-Methylimidazole-2-methanol (3.15 g, 28 mmol) (R. J. Sundberg; P. V. Nguyen; Med. Chem. Res. 7, 2, 1997, 123–136) was suspensed in THF (75 ml) at –20° C. and treated slowly (within 30 min) with N-bromosuccinimide (4.9 g, 27 mmol). The reaction mixture was allowed to warm up slowly to room temperature and quenched with saturated aqueous $NaHCO_3$ solution (50 ml). The aqueous layer was extracted 3 times with AcOEt. The combined extracts were washed with saturated aqueous $NaHCO_3$ solution, dried over $Na_2SO_4$, filtered and the solvent was removed in vacuo. The residue was chromatographed (silica, elution first with AcOEt/hexane 1:1, then with $CH_2Cl_2$/MeOH 95:05) to provide the title compound (2.11 g, 67%) as a white solid. MS: m/e=191.2 (M+).

EXAMPLE A

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

EXAMPLE B

Capsule Formulation

| | | mg/capsule | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

What is claimed is:
1. A compound of formula

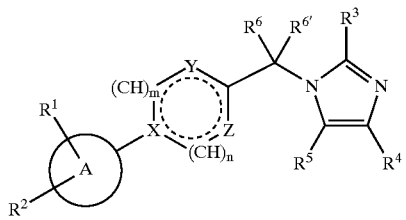

I wherein
A is phenyl, pyridin-2-yl, pyridin-3-yl, or piperidin-1-yl;
$R^1$ and $R^2$ are each independently selected from the group consisting of hydrogen, halogen, lower alkyl, cycloalkyl, lower alkenyl, trifluoromethyl, —O-trifluoromethyl, —S-trifluoromethyl, S-lower alkyl, lower alkoxy, —$CHF_2$, —C(lower alkyl)$F_2$, —$OCHF_2$, phenyl, nitro, benzyloxy, hydroxy and amino, or alternatively, $R^1$ and $R^2$
together with the carbon atoms to which they are attached in any adjacent positions from a group selected from —CH=CH—CH=CH—, —CH=CH—CH=N—, —(CH$_2$)$_3$—, —O—CH$_2$—O—, —O—CF$_2$—O—, —CH$_2$—O—CH$_2$— and —CH$_2$CH$_2$—O—;

R$^3$ is selected from the group consisting of hydrogen, lower alkyl, cycloalkyl, phenyl, S-lower alkyl, amino, lower alkyl-amino, —NHC(O)-lower alkyl and hydroxy-lower alkyl;

R$^4$ and R$^5$ are each independently selected from hydrogen and lower alkyl, or alternatively, R$^4$ and R$^5$ together with the carbon atoms to which they are attached form the group —(CH$_2$)$_4$—;

R$^6$ and R$^{6'}$ are each independently selected from hydrogen and lower alkyl;

X is —N< or

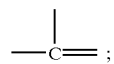

Y is =N—, —NH—, —N=CH— or —CH=;

Z is —CR$^7$=, —N=, —NR$^7$—, —N=CR$^7$—, =CH—N=C(R$^7$)— or =N—CH=CH—;

R$^7$ is hydrogen, —CH$_2$OH or lower alkyl;

n is 0, 1 or 2;

m is 0 or 1; and the dotted line may be 1, 2 or 3 bonds;

and pharmaceutically acceptable acid addition salts thereof.

2. The compound of claim 1 having the formula

I-1

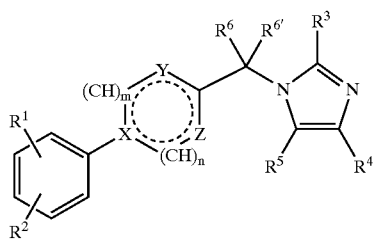

wherein

R$^1$ and R$^2$ are each independently selected from the group consisting of hydrogen, halogen, lower alkyl, trifluoromethyl, S-lower alkyl, lower alkoxy, —OCHF$_2$, phenyl, nitro, benzyloxy, hydroxy and amino, or alternatively, R$^1$ and R$^2$ together with the carbon atoms to which they are attached from a group selected from —(CH$_2$)$_3$—, —O—CH$_2$—O—, —CH$_2$—O—CH$_2$— and —CH$_2$CH$_2$—O—;

R$^3$ is selected from the group consisting of hydrogen, lower alkyl, phenyl, S-lower alkyl, amino, lower alkyl-amino, —NHC(O)-lower alkyl and hydroxy-lower alkyl;

R$^4$ and R$^5$ are each independently selected from hydrogen and lower alkyl, or alternatively, R$^4$ and R$^5$ together with the carbon atoms to which they are attached form the group —(CH$_2$)$_4$—;

R$^6$ and R$^{6'}$ are each independently selected from hydrogen and lower alkyl;

X is —N< or

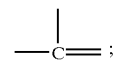

Y is =N—, —NH—, —N=CH— or —CH=;

Z is —CR$^7$=, —N=, —NH—, —N=CR$^7$—, =CH—N=C(R$^7$)— or =N—CH=CH—;

R$^7$ is hydrogen or lower alkyl;

n is 0, 1 or 2;

m is 0 or 1; and the dotted line may be 1, 2 or 3 bonds;

and pharmaceutically acceptable acid addition salts thereof.

3. The compound of claim 1 having the formula

Ia

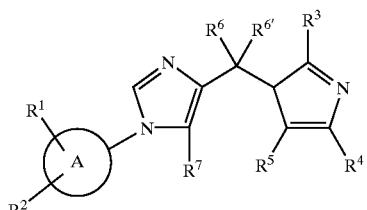

wherein A is phenyl.

4. The compound of claim 3, wherein R$^1$ and R$^2$ are each independently selected from the group consisting of lower alkyl —CHF$_2$, —C(lower alkyl)F$_2$, CF$_3$ and halogen, or alternatively, R$^1$ and R$^2$ together with the carbon atoms to which they are attached form the group —(CH$_2$)$_3$—; R$^3$ is lower alkyl or amino; and R$^4$, R$^5$, R$^6$, and R$^{6'}$ are hydrogen.

5. The compound according to claim 4, which is selected from the group consisting of 1H-imidazole, 1-[[1-(4-chloro-3-methylphenyl)-1H-imidazol-4-yl]methyl]-2-ethyl-;

1H-imidazole, 1-[[1-(4-chloro-3-methylphenyl)-1H-imidazol-4-yl]methyl]-2-methyl-;

1H-imidazole, 1-[[1-(2,3-dihydro-1H-inden-5-yl)-1H-imidazol-4-yl]methyl]-2-methyl-;

1H-imidazole, 1-[[1-[4-fluoro-3-(trifluoromethyl)phenyl]-1H-imidazol-4-yl]methyl]-2-methyl;

1-[1-(4-chloro-3-methyl-phenyl)-1H-imidazol-4-yl-methyl]-1H-imidazol-2-yl-amine;

1H-imidazole, 1-[[1-[3-(1,1-difluoroethyl)phenyl]-1H-imidazol-4-yl]methyl]-2-methyl-;

1H-imidazole, 1-[[1-(3-difluoromethyl-4-fluorophenyl)-1H-imidazol-4-yl]methyl]-2-methyl-; and 1H-imidazole, 1-[[1-[3-(1,1-difluoroethyl)-4-fluorophenyl]-1H-imidazol-4-yl]methyl]-2-methyl-.

6. The compound of claim 1 having the formula

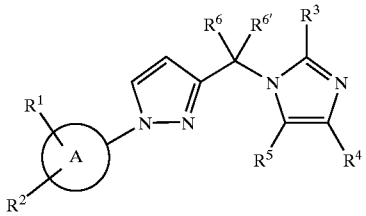

Ib wherein A is phenyl.

7. The compound of formula Ib in accordance with claim 6, wherein $R^1$ and $R^2$ are each independently selected from halogen; $R^3$ is lower alkyl or hydrogen; and $R^4$, $R^5$, $R^6$, and $R^{6'}$ are hydrogen.

8. The compound of formula Ib in accordance with claim 7, which is 1-(3,4-dichloro-phenyl)-3-(2-methyl-imidazol-1-yl-methyl)-1H-pyrazole.

9. The compound of claim 1 having the formula

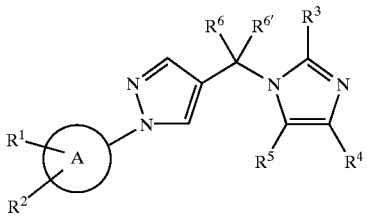

Ic wherein A is phenyl.

10. The compound of formula Ic in accordance with claim 9, wherein $R^1$ and $R^2$ are each independently selected from halogen; $R^3$ is lower alkyl or hydrogen; and $R^4$, $R^5$, $R^6$, and $R^{6'}$ are hydrogen.

11. The compound of formula Ic in accordance with claim 10, which is selected from the group consisting of 1-(3,4-dichloro-phenyl)-4-imidazol-1-yl-methyl-1H-pyrazole; and 1-(3,4-dichloro-phenyl)-4-(2-methyl-imidazol-1-yl-methyl)-1H-pyrazole.

12. The compound of claim 1 having the formula

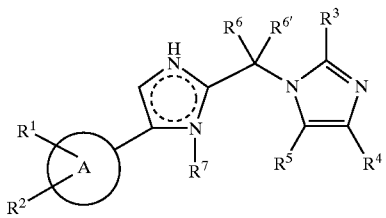

Id wherein A is phenyl.

13. The compound of formula Id in accordance with claim 12, wherein $R^1$ and $R^2$ are each independently selected from halogen, hydrogen, $CF_3$ and lower alkyl; $R^3$ is lower alkyl or hydrogen; and $R^4$, $R^5$, $R^6$, and $R^{6'}$ are hydrogen.

14. The compound of formula Id in accordance with claim 13, which is selected from the group consisting of 1H-imidazole, 2-methyl-1-[[4-[3-(trifluoromethyl)phenyl]-1H-imidazol-2-yl]methyl]-;

1H-imidazole, 1-[[4-(4-fluoro-3-methylphenyl)-1H-imidazol-2-yl]methyl]-2-methyl-;

1H-imidazole, 1-[[4-(3,4-difluorophenyl)-1H-imidazol-2-yl]methyl]-2-methyl-; and 1H-imidazole, 4-(4-fluoro-3-methylphenyl)-2-(1H-imidazol-1-yl-methyl)-.

15. The compound of claim 1 wherein A is pyridin-2-yl, pyridin-3-yl, or pyridin-1-yl.

16. A compound of formula

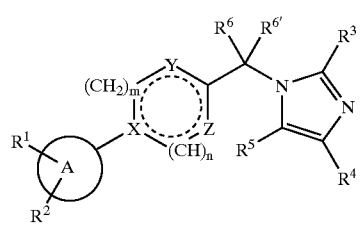

I wherein

A is phenyl, pyridin-2-yl, pyridin-3-yl, or piperidin-1-yl;

$R^1$ and $R^2$ are each independently selected from the group consisting of hydrogen, halogen, lower alkyl, cycloalkyl, lower alkenyl, trifluoromethyl, —O-trifluoromethyl, —S-trifluoromethyl, S-lower alkyl, lower alkoxy, —$CHF_2$, —C(lower alkyl)$F_2$, —$OCHF_2$, phenyl, nitro, benzyloxy, hydroxy and amino, or alternatively, $R^1$ and $R^2$ together with the carbon atoms to which they are attached in any adjacent positions from a group selected from —CH=CH—CH=CH—, —CH=CH—CH=N—, —$(CH_2)_3$—, —O—$CH_2$—O—, —O—$CF_2$—O—, —$CH_2$—O—$CH_2$— and —$CH_2CH_2$—O—;

the heterocyclic aromatic group

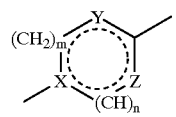

in formula I is selected from the group consisting of

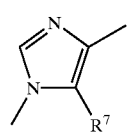

a)

b)

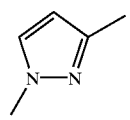

c)

-continued d) 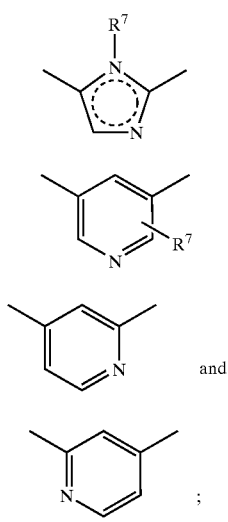

R³ is selected from the group consisting of hydrogen, lower alkyl, cycloalkyl, phenyl, S-lower alkyl, amino, lower alkyl-amino, —NHC(O)-lower alkyl and hydroxy-lower alkyl;

R⁴ and R⁵ are each independently selected from hydrogen and lower alkyl, or alternatively, R⁴ and R⁵ together with the carbon atom to which they are attached form the group —(CH₂)₄—;

R⁶ and R⁶' are each independently selected from hydrogen and lower alkyl; and

R⁷ is hydrogen, —CH₂OH or lower alkyl;

and pharmaceutically acceptable acid addition salts thereof.

17. A pharmaceutical composition comprising one or more compounds of formula I or a pharmaceutically acceptable salt thereof, and an inert carrier.

18. A process for preparing a compound of formula I comprising:

reacting a compound of formula

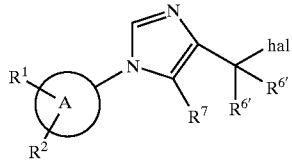

II with a compound of formula

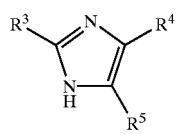

V to give a compound of formula

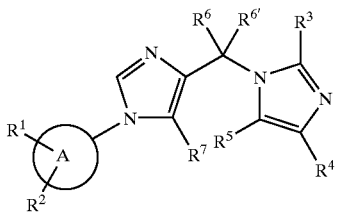

Ia wherein

A is phenyl or pyridin-2 or 3-yl;

R¹ and R² are each independently selected from the group consisting of hydrogen, halogen, lower alkyl, trifluoromethyl, S-lower alkyl, lower alkoxy, —OCHF₂, phenyl, nitro, benzyloxy, hydroxy and amino, or alternatively, R¹ and R² together with the carbon atoms to which they are attached from a group selected from —(CH₂)₃—, —O—CH₂—O—, —CH₂—O—CH₂— and —CH₂CH₂—O—;

R³ is selected from the group consisting of hydrogen, lower alkyl, phenyl, S-lower alkyl, amino, lower alkyl-amino, —NHC(O)-lower alkyl and hydroxy-lower alkyl;

R⁴ and R⁵ are each independently selected from hydrogen and lower alkyl, or alternatively, R⁴ and R⁵ together with the carbon atom to which they are attached form the group —(CH₂)₄—;

R⁶ and R⁶' are each independently selected from hydrogen and lower alkyl;

R⁷ is hydrogen, —CH₂OH or lower alkyl; and hal is Br or Cl.

19. A process for preparing a compound of formula I comprising:

reacting a compound of formula

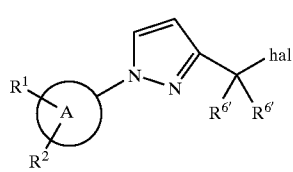

III with a compound of formula

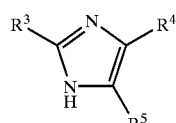

V to give a compound of formula

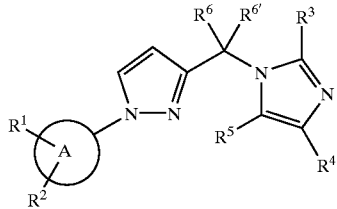

Ib wherein

A is phenyl or pyridin-2 or 3-yl;

R$^1$ and R$^2$ are each independently selected from the group consisting of hydrogen, halogen, lower alkyl, trifluoromethyl, S-lower alkyl, lower alkoxy, —OCHF$_2$, phenyl, nitro, benzyloxy, hydroxy and amino, or alternatively, R$^1$ and R$^2$ together with the carbon atoms to which they are attached from a group selected from —(CH$_2$)$_3$—, O—CH$_2$—O—, —CH$_2$—O—CH$_2$— and —CH$_2$CH$_2$—O—;

R$^3$ is selected from the group consisting of hydrogen, lower alkyl, phenyl, S-lower alkyl, amino, lower alkyl-amino, —NHC(O)-lower alkyl and hydroxy-lower alkyl;

R$^4$ and R$^5$ are each independently selected from hydrogen and lower alkyl, or alternatively, R$^4$ and R$^5$ together with the carbon atom to which they are attached form the group —(CH$_2$)$_4$—;

R$^6$ and R$^{6'}$ are each independently selected from hydrogen and lower alkyl; and hal is Br or Cl.

20. A process for preparing a compound of formula I comprising:

reacting a compound of formula

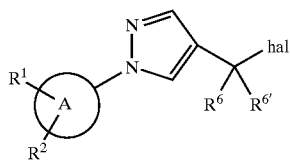

IV with a compound of formula

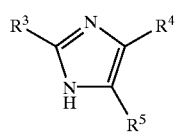

V to give a compound of formula

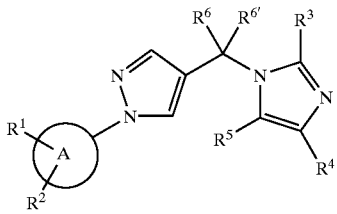

Ic wherein

A is phenyl or pyridin-2 or 3-yl;

R$^1$ and R$^2$ are each independently selected from the group consisting of hydrogen, halogen, lower alkyl, trifluoromethyl, S-lower alkyl, lower alkoxy, —OCHF$_2$, phenyl, nitro, benzyloxy, hydroxy and amino, or alternatively, R$^1$ and R$^2$ together with the carbon atoms to which they are attached from a group selected from —(CH$_2$)$_3$—, —O—CH$_2$—O—, —CH$_2$—O—CH$_2$— and —CH$_2$CH$_2$—O—;

R$^3$ is selected from the group consisting of hydrogen, lower alkyl, phenyl, S-lower alkyl, amino, lower alkyl-amino, —NHC(O)-lower alkyl and hydroxy-lower alkyl;

R$^4$ and R$^5$ are each independently selected from hydrogen and lower alkyl, or alternatively, R$^4$ and R$^5$ together with the carbon atom to which they are attached form the group —(CH$_2$)$_4$—;

R$^6$ and R$^{6'}$ are each independently selected from hydrogen and lower alkyl; and hal is Br or Cl.

21. A process for preparing a compound of formula I comprising:

cleaving off an N-protecting group from a compound of formula

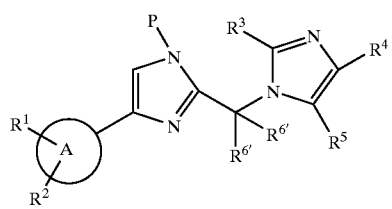

VI to give a compound of formula

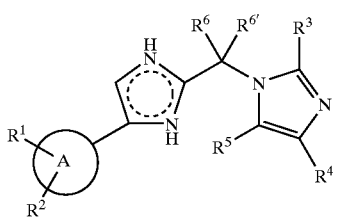

Id wherein

R$^1$ and R$^2$ are each independently selected from the group consisting of hydrogen, halogen, lower alkyl, cycloalkyl, lower alkenyl, trifluoromethyl, —O-trifluoromethyl, —S-trifluoromethyl, S-lower alkyl, lower alkoxy, —CHF$_2$, —C(lower alkyl)F$_2$, —OCHF$_2$, phenyl, nitro, benzyloxy, hydroxy and amino, or alternatively, R$^1$ and R$^2$ together with the carbon atoms to which they are attached in any adjacent positions from a group selected from —CH=CH—CH=CH—, —CH=CH—CH=N—, —(CH$_2$)$_3$—, —O—CH$_2$—O—, —O—CF$_2$—O—, —CH$_2$—O—CH$_2$— and —CH$_2$CH$_2$—O—;

R$^3$ is selected from the group consisting of hydrogen, lower alkyl, cycloalkyl, phenyl, S-lower alkyl, amino, lower alkyl-amino, —NHC(O)-lower alkyl and hydroxy-lower alkyl;

R$^4$ and R$^5$ are each independently selected from hydrogen and lower alkyl, or alternatively, R$^4$ and R$^5$ together with the carbon atom to which they are attached form the group —(CH$_2$)$_4$—;

R$^6$ and R$^{6'}$ are each independently selected from hydrogen and lower alkyl; and P is an N-protecting group.

22. The method of claim 21 wherein the N-protecting group is 2-(trimethylsilyl)-ethoxymethyl group.

23. A method of treating an NMDA-receptor-mediated disease comprising administering to a patient in need of such treatment an effective amount of a compound of claim 1.

24. The method of claim 23 wherein the NMDA-receptor disease is acute neurodegeneration caused by stroke or brain trauma.

25. The method of claim 23 wherein the NMDA-receptor disease is chronic neurodegeneration caused by Alzheimer's disease, Parkinson's disease, Huntington's disease, or ALS (amyotrophic lateral sclerosis).

* * * * *